United States Patent
Lipovsek

(10) Patent No.: US 10,450,363 B2
(45) Date of Patent: Oct. 22, 2019

(54) STABILIZED FIBRONECTIN BASED SCAFFOLD MOLECULES

(71) Applicant: BRISTOL-MYERS SQUIBB COMPANY, Princeton, NJ (US)

(72) Inventor: Dasa Lipovsek, Cambridge, MA (US)

(73) Assignee: BRISTOL-MYERS SQUIBB COMPANY, Princeton, NJ (US)

( * ) Notice: Subject to any disclaimer, the term of this patent is extended or adjusted under 35 U.S.C. 154(b) by 351 days.

(21) Appl. No.: 15/127,183

(22) PCT Filed: Mar. 19, 2015

(86) PCT No.: PCT/US2015/021466
§ 371 (c)(1),
(2) Date: Sep. 19, 2016

(87) PCT Pub. No.: WO2015/143156
PCT Pub. Date: Sep. 24, 2015

(65) Prior Publication Data
US 2017/0183393 A1    Jun. 29, 2017

Related U.S. Application Data

(60) Provisional application No. 62/084,270, filed on Nov. 25, 2014, provisional application No. 61/955,975, filed on Mar. 20, 2014.

(51) Int. Cl.
| | | |
|---|---|---|
| C40B 40/10 | (2006.01) | |
| C07K 14/78 | (2006.01) | |
| A61K 47/64 | (2017.01) | |

(52) U.S. Cl.
CPC .......... *C07K 14/78* (2013.01); *A61K 47/6435* (2017.08); *C07K 2318/20* (2013.01); *C40B 40/10* (2013.01)

(58) Field of Classification Search
None
See application file for complete search history.

(56) References Cited

U.S. PATENT DOCUMENTS

| 6,207,446 B1 | 3/2001 | Szostak et al. |
|---|---|---|
| 6,214,553 B1 | 4/2001 | Szostak et al. |

(Continued)

FOREIGN PATENT DOCUMENTS

| EP | 1074563 A1 | 2/2001 |
|---|---|---|
| FR | 2 819 809 A1 | 7/2002 |

(Continued)

OTHER PUBLICATIONS

Bork, P. et al., "Proposed acquisition of an animal protein domain by bacteria.," Proc. Natl. Acad. Sci. USA, vol. 89 (19):8990-8994 (1992).

(Continued)

*Primary Examiner* — Christian C Boesen
(74) *Attorney, Agent, or Firm* — Nelson Mullins Riley & Scarborough LLP; Jane E. Remillard, Esq.; Cynthia L. Kanik

(57) ABSTRACT

Provided herein are proteins comprising a fibronectin based scaffold (FBS) domain, e.g., $^{10}$Fn3 molecules, that bind specifically to a target, and wherein the FBS domain is linked at its C-terminus to a region consisting of PmXn, wherein P is proline, X is any amino acid and wherein n is 0 or an integer that is at least 1 and m is an integer that is at least 1, and wherein the PmXn moiety provides an enhanced property to the FBS domain, e.g., enhanced stability, relative to the protein that is not linked to the PmXn moiety.

20 Claims, 1 Drawing Sheet
Specification includes a Sequence Listing.

RDLEVVAATPTSLLISWDAPAVTVRYYRITYGETGGNSPVQEFTVPGSKSTATISGLK
PGVDYTITVYAVTGRGDSPASSKPISINYRTEI

(56) References Cited

U.S. PATENT DOCUMENTS

| | | | |
|---|---|---|---|
| 6,258,558 | B1 | 7/2001 | Szostak et al. |
| 6,261,804 | B1 | 7/2001 | Szostak et al. |
| 6,281,344 | B1 | 8/2001 | Szostak et al. |
| 6,518,018 | B1 | 2/2003 | Szostak et al. |
| 6,989,452 | B2 | 1/2006 | Ng et al. |
| 7,087,600 | B2 | 8/2006 | Ng et al. |
| 7,115,396 | B2 | 10/2006 | Lipovsek et al. |
| 7,129,261 | B2 | 10/2006 | Ng et al. |
| 7,858,739 | B2 | 12/2010 | Chen et al. |
| 8,420,098 | B2 | 4/2013 | Camphausen et al. |
| 9,234,027 | B2 | 1/2016 | Camphausen et al. |
| 9,562,089 | B2 | 2/2017 | Camphausen et al. |
| 9,856,309 | B2 | 1/2018 | Camphausen et al. |
| 2003/0190740 | A1 | 10/2003 | Altman |
| 2005/0095604 | A1 | 5/2005 | Kim et al. |
| 2006/0004081 | A1 | 1/2006 | Chen et al. |
| 2006/0024317 | A1 | 2/2006 | Boyd et al. |
| 2006/0121538 | A1 | 6/2006 | Vita et al. |
| 2006/0247295 | A1 | 11/2006 | Gangwar et al. |
| 2010/0040646 | A1 | 2/2010 | Nassal et al. |
| 2012/0094909 | A1* | 4/2012 | Camphausen ......... A61K 38/39 514/9.3 |
| 2013/0184212 | A1 | 7/2013 | Camphausen et al. |
| 2017/0166627 | A1 | 6/2017 | Camphausen et al. |
| 2017/0258948 | A1 | 9/2017 | Morin et al. |
| 2018/0258158 | A1 | 9/2018 | Krystek, Jr. et al. |

FOREIGN PATENT DOCUMENTS

| | | |
|---|---|---|
| WO | 00/34784 | 6/2000 |
| WO | 01/64942 | 9/2001 |
| WO | 02/04523 A2 | 1/2002 |
| WO | 02/032925 A2 | 4/2002 |
| WO | 02059146 A2 | 8/2002 |
| WO | 02/096910 A1 | 12/2002 |
| WO | 07/038658 A2 | 4/2007 |
| WO | 07/059404 A2 | 5/2007 |
| WO | 2007/051081 A1 | 5/2007 |
| WO | 2007/062064 A2 | 5/2007 |
| WO | 08/083312 A2 | 7/2008 |
| WO | 08/103693 A2 | 8/2008 |
| WO | 2009/023184 A2 | 2/2009 |
| WO | 2009/058379 A2 | 5/2009 |
| WO | 2009/083804 A2 | 7/2009 |
| WO | 2009/086116 A2 | 7/2009 |
| WO | 2009/133208 A1 | 11/2009 |
| WO | 2010/051274 A2 | 5/2010 |
| WO | 2010/051310 A2 | 5/2010 |
| WO | 2010/093627 A2 | 8/2010 |
| WO | 2011/020033 A2 | 2/2011 |
| WO | 2011/051466 A1 | 5/2011 |
| WO | 2011/092233 A1 | 8/2011 |
| WO | 2011/100700 A2 | 8/2011 |
| WO | 2011/130324 A1 | 10/2011 |
| WO | 2011/130328 A1 | 10/2011 |
| WO | 2011/130354 A1 | 10/2011 |
| WO | 2011/137319 A2 | 11/2011 |
| WO | 2011/150133 A2 | 12/2011 |
| WO | 2012/016245 A2 | 2/2012 |
| WO | 2013/067029 A2 | 5/2013 |
| WO | 2014/043344 A1 | 3/2014 |
| WO | 2014120891 A2 | 8/2014 |
| WO | 2015143156 A1 | 9/2015 |
| WO | 2016/086021 A1 | 6/2016 |
| WO | 2017/053617 A1 | 3/2017 |
| WO | 2017/053619 A1 | 3/2017 |
| WO | 2017/210302 A1 | 12/2017 |
| WO | 2017/210335 A1 | 12/2017 |

OTHER PUBLICATIONS

Bork, P. et al., "The immunoglobulin fold. Structural classification, sequence patterns and common core.," J. Mol. Biol., vol. 242(4):309-320 (1994).

Campbell, I.D., et al., "Building proteins with fibronectin type III modules.," Structure, vol. 2(5):333-337 (1994).

Dickinson et al., "Crystal structure of the tenth type III cell adhesion module of human fibronectin", J. Mol. Biol., vol. 36:1079-1092 (1994).

Harpez, Y. et al., "Many of the immunoglobulin superfamily domains in cell adhesion molecules and surface receptors belong to a new structural set which is close to that containing variable domains," J. Mol. Biol., 238(4):528-539 (1994).

International Preliminary Report on Patentability, PCT/US2015/021466, dated Sep. 20, 2016, 8 pages.

International Search Report and Written Opinion, PCT/US2015/021466, dated Jul. 2, 2015, 13 pages.

Roberts, R.W., et al., "RNA-peptide fusions for the in vitro selection of peptides and proteins," Proc Natl. Acad. Sci., 94:12297-12302 (1997).

Jacobs. S. et al., "Design of novel FN3 domains with high stability by a consensus sequence approach," Protein Engineering, Design & Selection, vol. 25:107-117 (2012).

* cited by examiner

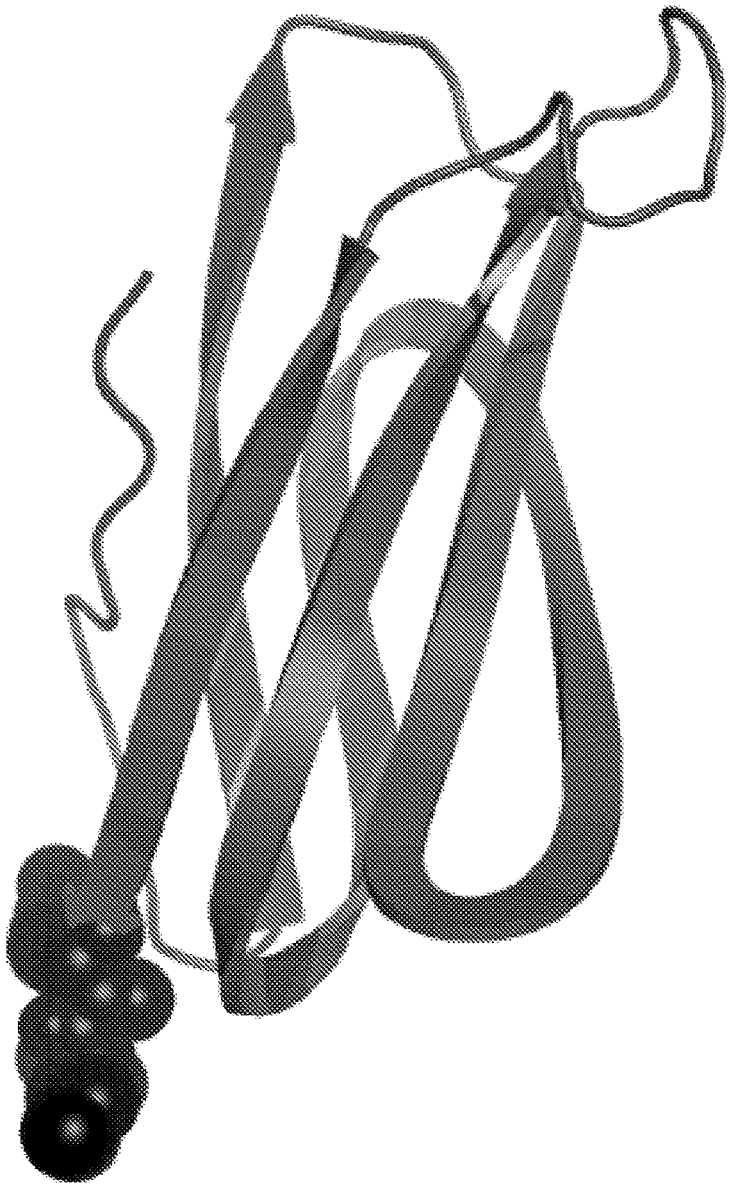
RDLEVVAATPTSLLISWDAPAVTVRYYRITYGETGGNSPVQEFTVPGSKSTATISGLK
PGVDYTITVYAVTGRGDSPASSKPISINY<u>RTEI</u>

STABILIZED FIBRONECTIN BASED SCAFFOLD MOLECULES

CROSS-REFERENCE TO RELATED APPLICATIONS

This application is a 35 U.S.C. 371 national stage filing of International Application No. PCT/US2015/021466, filed Mar. 19, 2015, which claims the benefit of U.S. Provisional Application No. 61/955,975, filed Mar. 20, 2014, and U.S. Provisional Application No. 62/084,270, filed Nov. 25, 2014. The contents of the aforementioned applications are hereby incorporated by reference.

SEQUENCE LISTING

The instant application contains a Sequence Listing which has been submitted via EFS-Web and is hereby incorporated by reference in its entirety. Said ASCII copy, created on Dec. 17, 2018, is named MXI_553US_Sequence_Listing.txt and is 74,552 bytes in size.

BACKGROUND

Adnectins are a class of therapeutic proteins with high-affinity and specific target-binding properties that are derived from the tenth human fibronectin type III domain ($^{10}$Fn3). Whereas wild-type $^{10}$Fn3 is extremely stable and soluble, target-binding variants of $^{10}$Fn3, which contain in the order of 4-31 mutations from the wild-type sequence, vary widely in stability and solubility. In other words, any mutations from the wild-type $^{10}$Fn3 sequence, even if required for target binding, carries a risk of reducing the stability of protein. As a consequence, it would be desirable to identify modifications that can be made to the wild-type $^{10}$Fn3 sequence that would stabilize it, preferably regardless of the identity of the residues that mediate Adnectin binding to their therapeutic targets.

SUMMARY

Provided herein are stabilized fibronectin based scaffold (FBS) proteins, e.g., Fn3, such as $^{10}$Fn3 molecules (e.g., human $^{10}$Fn3 molecules) that are linked at their C-terminus to a moiety consisting of the amino acid sequence PmXn, wherein P is proline, X is any amino acid, m is an integer that is at least 1 and n is 0 or an integer that is at least 1, and wherein the PmXn moiety enhances at least one characteristic, e.g., thermostability, of the FBS proteins.

BRIEF DESCRIPTION OF THE FIGURES

FIG. 1: Representation of a crystal structure of the human $^{10}$Fn3 domain (PDB ID: 1FNA), and the protein sequence of the polypeptide visible in the structure. The last two residues defined in the structure, the "EI" in the sequence of interest, are shown as black spheres, immediately downstream from the C-terminal beta strand, G.

DETAILED DESCRIPTION

Definitions

An "amino acid residue" is the remaining portion of an amino acid after a water molecule has been lost (an H+ from the nitrogenous side and an OH— from the carboxylic side) in the formation of a peptide bond.

As used herein, a "$^{10}$Fn3 domain" or "$^{10}$Fn3 moiety" or "$^{10}$Fn3 molecule" refers to wild-type $^{10}$Fn3 and biologically active variants thereof, e.g., biologically active variants that specifically bind to a target, such as a target protein. A wild-type human $^{10}$Fn3 domain may comprise one of the amino acid sequences set forth in SEQ ID NO: 1-8. Biologically active variants of a wild-type human $^{10}$Fn3 domain include $^{10}$Fn3 domains that comprise at least, at most or about 1, 2, 3, 4, 5, 6, 7, 8, 9, 10, 11, 12, 13, 14, 15, 16, 17, 18, 19, 20, 21, 22, 23, 24, 25, 30, 35, 40 or 45 amino acid changes, i.e., substitutions, additions or deletions, relative to a $^{10}$Fn3 domain comprising any one of SEQ ID NOs: 1-8. A biologically active variant of a wild-type $^{10}$Fn3 domain may also comprise, or comprise at most, 1-3, 1-5, 1-10, 1-15, 1-10, 1-25, 1-30, 1-35, 1-40 or 1-45 amino acid changes relative to a $^{10}$Fn3 domain comprising any one of SEQ ID NOs: 1-8. In certain embodiments, a biologically active variant of a wild-type $^{10}$Fn3 domain does not comprise more than 1, 2, 3, 4, 5, 6, 7, 8, 9, 10, 11, 12, 13, 14, 15, 16, 17, 18, 19, 20, 21, 22, 23, 24, 25, 30, 35, 40 or 45 amino acid changes, i.e., substitutions, additions or deletions, relative to an $^{10}$Fn3 domain comprising any one of SEQ ID NOs: 1-8. Amino acid changes may be in a loop region, in a strand or in the N-terminal or C-terminal region. Exemplary degenerate $^{10}$Fn3 amino acid sequences allowing for amino acid changes in the loop regions are provided herein as SEQ ID NOs: 9-16.

By "polypeptide" is meant any sequence of two or more amino acids, regardless of length, post-translation modification, or function. Polypeptides can include natural amino acids and non-natural amino acids such as those described in U.S. Pat. No. 6,559,126, incorporated herein by reference. Polypeptides can also be modified in any of a variety of standard chemical ways (e.g., an amino acid can be modified with a protecting group; the carboxy-terminal amino acid can be made into a terminal amide group; the amino-terminal residue can be modified with groups to, e.g., enhance lipophilicity; or the polypeptide can be chemically glycosylated or otherwise modified to increase stability or in vivo half-life). Polypeptide modifications can include the attachment of another structure such as a cyclic compound or other molecule to the polypeptide and can also include polypeptides that contain one or more amino acids in an altered configuration (i.e., R or S; or, L or D).

A "region" of a $^{10}$Fn3 domain (or moiety or molecule) as used herein refers to either a loop (AB, BC, CD, DE, EF and FG), a β-strand (A, B, C, D, E, F and G), the N-terminus (corresponding to amino acid residues 1-7 of SEQ ID NO: 1), or the C-terminus (corresponding to amino acid residues 93-94 of SEQ ID NO: 1).

A "north pole loop" of a $^{10}$Fn3 domain (or moiety) refers to any one of the BC, DE and FG loops of a $^{10}$Fn3 domain. A "south pole loop" of a $^{10}$Fn3 domain (or moiety) refers to any one of the AB, CD and EF loops of a $^{10}$Fn3 domain.

A "scaffold region" refers to any non-loop region of a human $^{10}$Fn3 domain. The scaffold region includes the A, B, C, D, E, F and G β-strands as well as the N-terminal region (amino acids corresponding to residues 1-7 of SEQ ID NO: 1) and the C-terminal region (amino acids corresponding to residues 93-94 of SEQ ID NO: 1).

"Percent (%) amino acid sequence identity" herein is defined as the percentage of amino acid residues in a candidate sequence that are identical with the amino acid residues in a selected sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST$^{SM}$, BLAST$^{SM}$-2, ALIGN, ALIGN-2 or Megalign (DNASTAR®) software. Those skilled in the art can determine appropriate parameters for measuring alignment, including any algorithms needed to achieve maximal alignment over the full-length of the sequences being compared.

For purposes herein, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y where X is the number of amino acid residues scored as identical matches by a sequence alignment program, such as BLAST$^{SM}$, BLAST$^{SM}$-2, ALIGN, ALIGN-2 or Megalign (DNASTAR®), in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

As used herein, an amino acid residue in a polypeptide is considered to "contribute to binding" a target if (1) any of the non-hydrogen atoms of the residue's side chain or main chain is found to be within five angstroms of any atom of the binding target based on an experimentally determined three-dimensional structure of the complex, and/or (2) mutation of the residue to its equivalent in wild-type $^{10}$Fn3 (e.g., SEQ ID NO: 1), to alanine, or to a residue having a similarly sized or smaller side chain than the residue in question, leads to a measured increase of the equilibrium dissociation constant to the target (e.g., an increase in the $k_{on}$).

The serum or plasma "half-life" of a polypeptide can generally be defined as the time taken for the serum concentration of the polypeptide to be reduced by 50%, in vivo, for example due to degradation of the polypeptide and/or clearance or sequestration of the polypeptide by natural mechanisms. The half-life can be determined in any manner known per se, such as by pharmacokinetic analysis. Suitable techniques will be clear to the person skilled in the art, and may, for example, generally involve the steps of administering a suitable dose of a polypeptide to a primate; collecting blood samples or other samples from said primate at regular intervals; determining the level or concentration of the polypeptide in said blood sample; and calculating, from (a plot of) the data thus obtained, the time until the level or concentration of the polypeptide has been reduced by 50% compared to the initial level upon dosing. Methods for determining half-life may be found, for example, in Kenneth et al., *Chemical Stability of Pharmaceuticals: A Handbook for Pharmacists* (1986); Peters et al., *Pharmacokinete Analysis: A Practical Approach* (1996); and Gibaldi, M. et al., *Pharmacokinetics*, Second Rev. Edition, Marcel Dekker (1982).

Serum half-life can be expressed using parameters such as the t1/2-alpha, t1/2-beta and the area under the curve (AUC). An "increase in half-life" refers to an increase in any one of these parameters, any two of these parameters, or in all three these parameters. In certain embodiments, an increase in half-life refers to an increase in the t1/2-beta, either with or without an increase in the t1/2-alpha and/or the AUC or both.

"Shelf-life" of a pharmaceutical product, e.g., a protein comprising an FBS moiety and an HSA moiety, is the length of time the product is stored before decomposition occurs. For example, shelf-life may be defined as the time for decomposition of 0.1%, 0.5%, 1%, 5%, or 10% of the product.

Overview

Provided herein are proteins comprising a fibronectin based scaffold (FBS) domain, e.g., Fn3, such as $^{10}$Fn3 molecules, that bind specifically to a target, and wherein the FBS domain is linked at its C-terminus to a region consisting of PmXn, wherein P is proline, X is any amino acid and wherein n is 0 or an integer that is at least 1 and m is an integer that is at least 1. The application is based at least in part on the discovery that adding a proline and optionally one or more amino acids at the C-terminus of a $^{10}$Fn3 molecule increases at least one characteristic of the $^{10}$Fn3 molecule, e.g., its thermostability or solubility, relative to the unmodified $^{10}$Fn3 molecule.

The $^{10}$Fn3 molecules described herein may be designed to bind to any target of interest. In exemplary embodiments, the target is an antigen, a polypeptide or a therapeutic protein target of interest. Exemplary therapeutically desirable targets, include, for example, tumor necrosis factor alpha (TNF-alpha), VEGFR2, PCSK9, IL-23, EGFR and IGF1R.

Fibronectin Based Scaffolds

As used herein, a "fibronectin based scaffold" or "FBS" protein or moiety refers to proteins or moieties that are based on a fibronectin type III ("Fn3") repeat. Fn3 is a small (about 10 kDa) domain that has the structure of an immunoglobulin (Ig) fold (i.e., an Ig-like β-sandwich structure, consisting of seven β-strands and six loops). Fibronectin has 18 Fn3 repeats, and while the sequence homology between the repeats is low, they all share a high similarity in tertiary structure. Fn3 domains are also present in many proteins other than fibronectin, such as adhesion molecules, cell surface molecules, e.g., cytokine receptors, and carbohydrate binding domains. For reviews see Bork et al., *Proc. Natl. Acad. Sci. USA*, 89(19):8990-8994 (1992); Bork et al., *J. Mol. Biol.*, 242(4):309-320 (1994); Campbell et al., *Structure*, 2(5):333-337 (1994); Harpez et al., *J. Mol. Biol.*, 238(4):528-539 (1994)). The term "FBS" protein or moiety is intended to include scaffolds based on Fn3 domains from these other proteins (i.e., non fibronectin molecules).

An Fn3 domain is small, monomeric, soluble, and stable. It lacks disulfide bonds and, therefore, is stable under reducing conditions. Fn3 domains comprise, in order from N-terminus to C-terminus, a beta or beta-like strand, A; a loop, AB; a beta or beta-like strand, B; a loop, BC; a beta or beta-like strand, C; a loop, CD; a beta or beta-like strand, D; a loop, DE; a beta or beta-like strand, E; a loop, EF; a beta or beta-like strand, F; a loop, FG; and a beta or beta-like strand, G. The seven antiparallel β-strands are arranged as two beta sheets that form a stable core, while creating two "faces" composed of the loops that connect the beta or beta-like strands. Loops AB, CD, and EF are located at one face ("the south pole") and loops BC, DE, and FG are located on the opposing face ("the north pole").

The loops in Fn3 molecules are structurally similar to complementary determining regions (CDRs) of antibodies, and when altered, may be involved in binding of the Fn3 molecule to a target, e.g., a target protein. Other regions of Fn3 molecules, such as the beta or beta-like strands and N-terminal or C-terminal regions, when altered, may also be involved in binding to a target. Any or all of loops AB, BC, CD, DE, EF and FG may participate in binding to a target. Any of the beta or beta-like strands may be involved in binding to a target. Fn3 domains may also bind to a target through one or more loops and one or more beta or beta-like strands. Binding may also require the N-terminal or C-terminal regions. An FBS domain for use in a protein may comprise all loops, all beta or beta-like strands, or only a portion of them, wherein certain loops and/or beta or beta-like strands and/or N- or C-terminal regions are modified (or altered), provided that the FBS domain preferably binds specifically to a target. For example, an FBS domain may comprise 1, 2, 3, 4, 5 or 6 loops, 1, 2, 3, 4, 5, 6, 7, or 8 beta the N-terminal region is shown in italics). The last two amino acid residues of SEQ ID NO: 1 are a portion of a C-terminal region.

Wild-type human [10]Fn3 molecules also include those lacking the N-terminal region or a portion thereof. For example, a wild-type [10]Fn3 molecule may comprise SEQ ID NO: 1, wherein amino acid residues 1, 1-2, 1-3, 1-4, 1-5, 1-6 or 1-7 are deleted (SEQ ID NOs: 2-8, respectively). Table 1 shows the amino acid sequence of these wild-type human [10]Fn3 moieties:

TABLE 1

Amino acid sequences of wild-type human [10]Fn3 molecules with various N-terminal regions

| Version | N-terminal region | Wild-type human [10]Fn3 core domain | Full length |
|---|---|---|---|
| 1 | VSDVPRD (SEQ ID NO: 19) | LEVVAATPTSLLISWDAPAVTVRYYRITY GETGGNSPVQEFTVPGSKSTATISGLKPG VDYTITVYAVTGRGDSPASSKPISINYRT (SEQ ID NO: 17) | SEQ ID NO: 1 |
| 2 | SDVPRD (SEQ ID NO: 20) | LEVVAATPTSLLISWDAPAVTVRYYRITY GETGGNSPVQEFTVPGSKSTATISGLKPG VDYTITVYAVTGRGDSPASSKPISINYRT (SEQ ID NO: 17) | SEQ ID NO: 2 |
| 3 | DVPRD (SEQ ID NO: 21) | LEVVAATPTSLLISWDAPAVTVRYYRITY GETGGNSPVQEFTVPGSKSTATISGLKPG VDYTITVYAVTGRGDSPASSKPISINYRT (SEQ ID NO: 17) | SEQ ID NO: 3 |
| 4 | VPRD (SEQ ID NO: 22) | LEVVAATPTSLLISWDAPAVTVRYYRITY GETGGNSPVQEFTVPGSKSTATISGLKPG VDYTITVYAVTGRGDSPASSKPISINYRT (SEQ ID NO: 17) | SEQ ID NO: 4 |
| 5 | PRD | LEVVAATPTSLLISWDAPAVTVRYYRITY GETGGNSPVQEFTVPGSKSTATISGLKPG VDYTITVYAVTGRGDSPASSKPISINYRT (SEQ ID NO: 17) | SEQ ID NO: 5 |
| 6 | RD | LEVVAATPTSLLISWDAPAVTVRYYRITY GETGGNSPVQEFTVPGSKSTATISGLKPG VDYTITVYAVTGRGDSPASSKPISINYRT (SEQ ID NO: 17) | SEQ ID NO: 6 |
| 7 | D | LEVVAATPTSLLISWDAPAVTVRYYRITY GETGGNSPVQEFTVPGSKSTATISGLKPG VDYTITVYAVTGRGDSPASSKPISINYRT (SEQ ID NO: 17) | SEQ ID NO: 7 |
| 8 | — | LEVVAATPTSLLISWDAPAVTVRYYRITY GETGGNSPVQEFTVPGSKSTATISGLKPG VDYTITVYAVTGRGDSPASSKPISINYRT (SEQ ID NO: 17) | SEQ ID NO: 8 | strands, and optionally an N-terminal and/or C-terminal region, wherein one or more loops, one or more beta strands, the N-terminal region and/or the C-terminal regions are modified relative to the wild-type FBS domain.

In exemplary embodiments, ligand (or target) binding FBS moieties described herein are based on the tenth fibronectin type III domain, i.e., the tenth module of Fn3 ([10]Fn3). The amino acid sequence of a wild-type human [10]Fn3 moiety is as follows: VSDVPRDLEVVAA TPTSLLISWDAPAVTVRYYRITY GETGGNSPVQEFTVPGSKS TATISGL KPGVDYTITVYAVTGRGDSPASSKPISINYRT (SEQ ID NO: 1) (the AB, CD and EF loops are underlined; the BC, FG, and DE loops are emphasized in bold; the β-strands are located between or adjacent to each of the loop regions; and In some embodiments, the AB loop corresponds to residues 14-17, the BC loop corresponds to residues 23-31, the CD loop corresponds to residues 37-47, the DE loop corresponds to residues 51-56, the EF loop corresponds to residues 63-67, and the FG loop corresponds to residues 75-87 of SEQ ID NO: 1. The BC, DE and FG loops align along one face of the molecule, i.e., the "north pole", and the AB, CD and EF loops align along the opposite face of the molecule, i.e., the "south pole". In SEQ ID NO: 1, β-strand A corresponds to residues 8-13, β-strand B corresponds to residues 18-22, β-strand C corresponds to residues 32-36, beta strand D corresponds to residues 48-50, β-strand E corresponds to residues 57-62, β-strand F corresponds to residues 68-74, and β-strand G corresponds to residues 88-92. The β-strands are connected to each other through the corresponding loop, e.g., strands A and B are connected via loop AB in the formation β-strand A, loop AB, β-strand B, etc.

An example of FBS proteins that are based on human $^{10}$Fn3 domains are adnectins (Adnexus, a wholly owned subsidiary of Bristol-Myers Squibb). Adnectins are $^{10}$Fn3 molecules in which CDR-like loop regions, β-strands, N-terminal and/or C-terminal regions of a $^{10}$Fn3 domain has been modified to evolve a protein capable of binding to a compound of interest. For example, U.S. Pat. No. 7,115,396 describes $^{10}$Fn3 domain proteins wherein alterations to the BC, DE, and FG loops result in high affinity TNFα binders. U.S. Pat. No. 7,858,739 describes Fn3 domain proteins wherein alterations to the BC, DE, and FG loops result in high affinity VEGFR2 binders.

In certain embodiments, the FBS moiety comprises a $^{10}$Fn3 domain that is defined generally by the following degenerate sequence:

(SEQ ID NO: 9)
VSDVPRD<u>LEVVAA</u>(X)$_u$<u>LLISW</u>(X)$_v$<u>YRITY</u>(X)$_w$<u>FTV</u>(X)$_x$<u>ATISGL</u>

(X)$_y$<u>YTITVYA</u>(X)$_z$<u>ISINYRT</u>, or by a sequence selected from the group of SEQ ID NO: 10-16, which sequences are identical to SEQ ID NO: 9, except that they are lacking 1, 2, 3, 4, 5, 6 or 7 N-terminal amino acids, respectively. Table 2 shows the amino acid sequences of these degenerate human $^{10}$Fn3 molecules.

independently be anywhere from 2-20, 2-15, 2-10, 2-8, 5-20, 5-15, 5-10, 5-8, 6-20, 6-15, 6-10, 6-8, 2-7, 5-7, or 6-7 amino acids. The sequences of the beta strands (underlined in SEQ ID NO: 9) may have anywhere from 0 to 10, from 0 to 8, from 0 to 6, from 0 to 5, from 0 to 4, from 0 to 3, from 0 to 2, or from 0 to 1 substitutions, deletions or additions across all 7 scaffold regions relative to the corresponding amino acids shown in SEQ ID NOs: 9-16. In some embodiments, the sequences of the beta strands may have anywhere from 0 to 10, from 0 to 8, from 0 to 6, from 0 to 5, from 0 to 4, from 0 to 3, from 0 to 2, or from 0 to 1 substitutions, e.g., conservative substitutions, across all 7 scaffold regions relative to the corresponding amino acids shown in SEQ ID NO: 9-16.

In certain embodiments, the hydrophobic core amino acid residues (bolded residues in SEQ ID NO: 9 above) are fixed, and any substitutions, conservative substitutions, deletions or additions occur at residues other than the hydrophobic core amino acid residues. Thus, in some embodiments, the hydrophobic core residues of the polypeptides provided herein have not been modified relative to the wild-type human $^{10}$Fn3 domain (e.g., SEQ ID NO: 1).

In some embodiments, an FBS moiety comprises a $^{10}$Fn3 domain, wherein the $^{10}$Fn3 domain comprises a loop, AB; a loop, BC; a loop, CD; a loop, DE; a loop, EF; and a loop,

TABLE 2

Amino acid sequences of degenerate wild-type human $^{10}$Fn3 molecules with various N-terminal regions

| Version | N-terminal region | Degenerate wild-type human $^{10}$Fn3 core domain | Full length |
|---|---|---|---|
| 1 | VSDVPRD (SEQ ID NO: 19) | LEVVAA(X)$_u$LLISW(X)$_v$YRITY(X)$_w$FTV (X)$_x$ATISGL(X)$_y$YTITVYA(X)$_z$ISINYRT (SEQ ID NO: 18) | SEQ ID NO: 9 |
| 2 | SDVPRD (SEQ ID NO: 20) | LEVVAA(X)$_u$LLISW(X)$_v$YRITY(X)$_w$FTV (X)$_x$ATISGL(X)$_y$YTITVYA(X)$_z$ISINYRT (SEQ ID NO: 18) | SEQ ID NO: 10 |
| 3 | DVPRD (SEQ ID NO: 21) | LEVVAA(X)$_u$LLISW(X)$_v$YRITY(X)$_w$FTV (X)$_x$ATISGL(X)$_y$YTITVYA(X)$_z$ISINYRT (SEQ ID NO: 18) | SEQ ID NO: 11 |
| 4 | VPRD (SEQ ID NO: 22) | LEVVAA(X)$_u$LLISW(X)$_v$YRITY(X)$_w$FTV (X)$_x$ATISGL(X)$_y$YTITVYA(X)$_z$ISINYRT (SEQ ID NO: 18) | SEQ ID NO: 12 |
| 5 | PRD | LEVVAA(X)$_u$LLISW(X)$_v$YRITY(X)$_w$FTV (X)$_x$ATISGL(X)$_y$YTITVYA(X)$_z$ISINYRT (SEQ ID NO: 18) | SEQ ID NO: 13 |
| 6 | RD | LEVVAA(X)$_u$LLISW(X)$_v$YRITY(X)$_w$FTV (X)$_x$ATISGL(X)$_y$YTITVYA(X)$_z$ISINYRT (SEQ ID NO: 18) | SEQ ID NO: 14 |
| 7 | D | LEVVAA(X)$_u$LLISW(X)$_v$YRITY(X)$_w$FTV (X)$_x$ATISGL(X)$_y$YTITVYA(X)$_z$ISINYRT (SEQ ID NO: 18) | SEQ ID NO: 15 |
| 8 | — | LEVVAA(X)$_u$LLISW(X)$_v$YRITY(X)$_w$FTV (X)$_x$ATISGL(X)$_y$YTITVYA(X)$_z$ISINYRT (SEQ ID NO: 18) | SEQ ID NO: 16 |

In SEQ ID NOs: 25-32 and 50, the AB loop is represented by (X)$_u$, the BC loop is represented by (X)$_v$, the CD loop is represented by (X)$_w$, the DE loop is represented by (X)$_x$, the EF loop is represented by (X)$_y$, and the FG loop is represented by X$_z$. X represents any amino acid and the subscript following the X represents an integer of the number of amino acids. In particular, u, v, w, x, y and z may each FG; and has at least one loop selected from loop AB, BC, CD, DE, EF and FG with an altered amino acid sequence relative to the sequence of the corresponding loop of the wild-type human $^{10}$Fn3 domain. In some embodiments, a single loop is altered. In some embodiments, at most 2 loops are altered. In some embodiments, at most 3 loops are altered. In some embodiments, the BC, DE and/or FG loops are altered. In certain embodiments, the AB, CD and EF loops are altered. In certain embodiments, the FG loop is the only loop that is altered. In certain embodiments, the CD loop is the only loop that is altered. In other embodiments, the CD and FG loops are both altered, and optionally, no other loops are altered. In certain embodiments, the CD and EF loops are both altered, and optionally, no other loops are altered. In some embodiments, one or more specific scaffold alterations are combined with one or more loop alterations. By "altered" is meant one or more amino acid sequence alterations relative to a template sequence (i.e., the corresponding wild-type human fibronectin domain) and includes amino acid additions, deletions, and substitutions. Exemplary $^{10}$Fn3 molecules comprising specific combinations of altered loops and/or scaffold regions (e.g., beta strands, N-terminal region and C-terminal region) are further disclosed herein.

It should be understood that not every residue within a loop region needs to be modified in order to achieve a $^{10}$Fn3 binding domain having strong affinity for a desired target. Additionally, insertions and deletions in the loop regions may also be made while still producing high affinity $^{10}$Fn3 binding domains.

In some embodiments, one or more loops selected from AB, BC, CD, DE, EF and FG may be extended or shortened in length relative to the corresponding loop in wild-type human $^{10}$Fn3. In any given polypeptide, one or more loops may be extended in length, one or more loops may be reduced in length, or combinations thereof. In some embodiments, the length of a given loop may be extended by 2-25, 2-20, 2-15, 2-10, 2-5, 5-25, 5-20, 5-15, 5-10, 10-25, 10-20, or 10-15 amino acids. In some embodiments, the length of a given loop may be reduced by 1-15, 1-11, 1-10, 1-5, 1-3, 1-2, 2-10, or 2-5 amino acids. In particular, the FG loop of $^{10}$Fn3 is 13 residues long, whereas the corresponding loop in antibody heavy chains ranges from 4-28 residues. To optimize antigen binding in polypeptides relying on the FG for target binding, therefore, the length of the FG loop of $^{10}$Fn3 may be altered in length as well as in sequence to obtain the greatest possible flexibility and affinity in target binding.

In some embodiments, the FBS moiety comprises a $^{10}$Fn3 domain wherein the non loop regions comprise an amino acid sequence that is at least 80, 85, 90, 95, 98, or 100% identical to the non-loop regions of SEQ ID NO: 1, wherein at least one loop selected from AB, BC, CD, DE, EF and FG is altered. For example, in certain embodiments, the AB loop may have up to 4 amino acid substitutions, up to 10 amino acid insertions, up to 3 amino acid deletions, or a combination thereof; the BC loop may have up to 10 amino acid substitutions, up to 4 amino acid deletions, up to 10 amino acid insertions, or a combination thereof; the CD loop may have up to 6 amino acid substitutions, up to 10 amino acid insertions, up to 4 amino acid deletions, or a combination thereof; the DE loop may have up to 6 amino acid substitutions, up to 4 amino acid deletions, up to 13 amino acid insertions, or a combination thereof; the EF loop may have up to 5 amino acid substitutions, up to 10 amino acid insertions, up to 3 amino acid deletions, or a combination thereof; and/or the FG loop may have up to 12 amino acid substitutions, up to 11 amino acid deletions, up to 25 amino acid insertions, or a combination thereof.

In some embodiments, an FBS moiety comprises a $^{10}$Fn3 domain having at least 40%, 50%, 55%, 60%, 65%, 70%, 75%, 80%, 85%, or 90% identity to a human $^{10}$Fn3 domain having an amino acid sequence selected from the group of sequence comprising SEQ ID NOs: 1-16. In certain embodiments, the FBS moiety provided herein has at least 50% identity to an amino acid sequence selected from the group of amino acid sequences comprising SEQ ID NO: 1-16. In other embodiments, the FBS moiety has at least 65% identity to an amino acid sequence selected from the group of amino acid sequences comprising SEQ ID NO: 1-16. In certain embodiments, one or more of the loops will not be modified relative to the sequence of the corresponding loop of the wild-type sequence and/or one or more of the β-strands will not be modified relative to the sequence of the corresponding β-strand of the wild-type sequence and/or the N-terminal or C-terminal regions will not be modified. In certain embodiments, each of the beta or beta-like strands of a $^{10}$Fn3 domain in an FBS moiety may comprise, consist essentially of, or consist of an amino acid sequence that is at least 80%, 85%, 90%, 95% or 100% identical to the sequence of a corresponding beta or beta-like strand of SEQ ID NO: 1. Preferably, variations in the β-strand regions will not disrupt the stability of the polypeptide in physiological conditions.

In some embodiments, the non-loop region of a $^{10}$Fn3 domain may be modified by one or more conservative substitutions. As many as 5%, 10%, 20% or even 30% or more of the amino acids in the $^{10}$Fn3, domain may be altered by a conservative substitution without substantially altering the affinity of the $^{10}$Fn3 for a ligand. In certain embodiments, the non-loop regions, e.g., the β-strands may comprise anywhere from 0-15, 0-10, 0-8, 0-6, 0-5, 0-4, 0-3, 1-15, 1-10, 1-8, 1-6, 1-5, 1-4, 1-3, 2-15, 2-10, 2-8, 2-6, 2-5, 2-4, 5-15, or 5-10 conservative amino acid substitutions. In exemplary embodiments, the scaffold modification may reduce the binding affinity of the $^{10}$Fn3 binder for a ligand by less than 100-fold, 50-fold, 25-fold, 10-fold, 5-fold, or 2-fold. It may be that such changes may alter the immunogenicity of the $^{10}$Fn3 in vivo, and where the immunogenicity is decreased, such changes may be desirable. As used herein, "conservative substitutions" are residues that are physically or functionally similar to the corresponding reference residues. That is, a conservative substitution and its reference residue have similar size, shape, electric charge, chemical properties including the ability to form covalent or hydrogen bonds, or the like. Exemplary conservative substitutions include those fulfilling the criteria defined for an accepted point mutation in Dayhoff et al., *Atlas of Protein Sequence and Structure,* 5:345-352 (1978 and Supp.). Examples of conservative substitutions include substitutions within the following groups: (a) valine, glycine; (b) glycine, alanine; (c) valine, isoleucine, leucine; (d) aspartic acid, glutamic acid; (e) asparagine, glutamine; (f) serine, threonine; (g) lysine, arginine, methionine; and (h) phenylalanine, tyrosine.

Also provided herein are $^{10}$Fn3 domains having combinations of loop and scaffold modifications. Conjugates may comprise a $^{10}$Fn3, domain comprising (i) a modification in the amino acid sequence of at least one of loops AB, BC, CD, DE, EF, or FG, and (ii) a modification in the amino acid sequence of at least one scaffold region (i.e., a modification in at least one β-strand, the N-terminal region, and/or the C-terminal region), wherein the modified loop(s) and modified scaffold region(s) both contribute to binding the same target. In exemplary embodiments, the scaffold region modifications are located adjacent to modifications in a loop region, e.g., if the AB loop is modified, scaffold mutations may tend to be located in β-strand A and/or β-strand B, which are adjacent to the AB loop in the linear sequence of the $^{10}$Fn3 domain. In other embodiments, a cluster of modifications may be found together in loop and scaffold regions that are adjacent to one another in the linear sequence of the Fn3 domain. For example, Fn3 binders having both loop and scaffold modifications, may have clusters of amino acid modifications in the following combinations of loop and scaffold regions that are adjacent to each other in the linear sequence of the Fn3 domain: β-strand/loop/β-strand, loop/β-strand/loop, loop/β-strand/loop/β-strand, terminal region/β-strand/loop, or loop/β-strand/terminal region, etc. For example, Fn3 domains having novel combinations of loop and scaffold modifications may have clusters of modifications such that over a stretch of 20 contiguous amino acids at least 15 of the amino acids are modified relative to wild-type. In other embodiments, at least 17 out of 20, 18 out of 20, 17 out of 25, 20 out of 25, or 25 out of 30 residues in a contiguous stretch are modified relative to the wild-type Fn3 domain sequence over the corresponding stretch of amino acids. In certain embodiments, a given Fn3 domain may have two or three clusters of modifications separated by stretches of unmodified (i.e., wild-type) sequence. For any given region (i.e., a loop, β-strand or terminal region) that is modified, all or only a portion of the region may be modified relative to the wild-type sequence. When a β-strand region is modified, preferably the hydrophobic core residues remain unmodified (i.e., wild-type) and one or more of the non-core residues in the β-strand are modified.

In some embodiments, $^{10}$Fn3 domains comprise a binding face along the "west-side" of the molecule ("West-side binders" or "WS binders"). WS binders may comprise a modified CD loop and a modified FG loop, as compared to the corresponding CD and FG loop sequences set forth in SEQ ID NO: 1. The CD loop and the FG loop both contribute to binding to the same target. In certain embodiments, the WS binders may comprise additional modifications at one or more regions within the Fn3 domain. For example, WS binders may comprise scaffold modifications in one or more of the β-strand regions adjacent to the CD and/or FG loops. In particular, WS binders may comprise sequence modifications in one or more of β-strand C, β-strand D, β-strand F, and/or βstrand G. Exemplary scaffold modifications include modifications at one or more scaffold region positions corresponding to the amino acid positions: 33, 35, 49, 69, 71, 73, 89 and/or 91 of SEQ ID NO: 1. The WS binders may also comprise modifications in the BC loop, particularly in the C-terminal portion of the BC loop. In one embodiment, the last two residues of the BC loop (i.e., corresponding to amino acids 30 and 31 in the wild-type $^{10}$Fn3 domain) are modified relative to the wild-type sequence. All or a portion of the additional loop and scaffold modifications may contribute to binding to the target in conjunction with the modified CD and FG loops. Preferably, the hydrophobic core residues are not modified relative to the wild-type sequence.

Exemplary WS binders include those having a wild-type or mutated amino acid at positions 30, 31, 33, 35, 37, 38, 46, 47, 49, 50, 67, 69, 71, 73, 75, 76, 84, 85, 86, 87, 89 or 91.

In some embodiments, a $^{10}$Fn3 domain comprises modifications in the CD, DE and, in some cases, EF loops, wherein the loop modifications all contribute to target binding. These polypeptides are referred to as "front binders". The front binders may additionally comprise modifications in one or more scaffold regions, particularly in scaffold regions that flank or are adjacent to a modified loop region. For example, the front binders may comprise a scaffold modification in one or more of β-strand C, β-strand D, and/or β-strand E relative to the sequences of the corresponding β-strands of the wild-type Fn3 domain, e.g., human $^{10}$Fn3 domain (SEQ ID NO: 1). Preferably the hydrophobic core residues are not modified relative to the wild-type sequence. Exemplary scaffold modifications that may be present in front binders, include modifications at one or more positions corresponding to amino acid positions 36, 49, 58 and/or 50 of SEQ ID NO: 1. Such scaffold modifications may contribute to binding to the target together with the modified loops. In certain embodiments, the front binders may comprise clusters of modifications spanning several loop and strand regions of the Fn3, e.g., $^{10}$Fn3, domain. In particular, the front binders may comprise modifications in at least 15, 20, 24, 25, or 27 of the 31 residues between the amino acids corresponding to residues 36 through 66 of the wild-type Fn3, e.g., human $^{10}$Fn3, domain (SEQ ID NO: 1). The loop and/or strand modifications may include amino acid substitutions, deletions and/or insertions, or combinations thereof. In exemplary embodiments, the CD loop is extended in length or reduced in length relative to the CD loop of the Fn3, e.g., wild-type human $^{10}$Fn3, domain (SEQ ID NO: 1).

In some embodiments, $^{10}$Fn3 domains comprise modifications in the EF and FG loops, wherein the loop modifications contribute to binding the same target. These polypeptides are referred to as "back binders" herein. The back binders may comprise additional modifications in other loop and/or scaffold regions. For example, a back binder may contain modifications in at least a portion of the AB loop, preferably the N-terminal portion of the AB loop. In an exemplary embodiment, the first two amino acids of the AB loop (i.e., corresponding to amino acid residues 14 and 15 of the wild-type $^{10}$Fn3 domain) are modified relative to the wild-type sequence. In certain embodiments, a back binder may also contain one or more scaffold modifications, particularly modifications in one or more scaffold regions that are adjacent to a modified loop region. For example, back binders may contain one or more modifications in one or more of β-strand A, β-strand G, the N-terminal region, and/or the C-terminal region. Preferably the hydrophobic core residues are not modified relative to the wild-type sequence. Exemplary scaffold modifications include modifications at one or more positions corresponding to amino acid positions 1-7, 9-13, 89, 91, 93 and/or 94 of SEQ ID NO: 1. One or more of the additional loop and/or scaffold modifications may contribute to binding to the target along with the modified EF and FG loops. Suitable loop and/or scaffold region modifications include amino acid substitutions, deletions and/or insertions, or combinations thereof. In certain embodiments, the amino acid sequence of the FG loop is extended in length or reduced in length relative to the FG loop of the wild-type human $^{10}$Fn3 domain (SEQ ID NO: 1).

In certain embodiments, a back binder may comprise a cluster of modified amino acid residues over a contiguous span of several regions in the $^{10}$Fn3 domain. For example, at least 14 of the first 15 amino acid residues of the Fn3, e.g., $^{10}$Fn3, domain may be modified relative to the corresponding residues in the wild-type Fn3, e.g., human $^{10}$Fn3, domain (SEQ ID NO: 1), and/or at least 15 of the 18 residues between the amino acids corresponding to residues 80 through 97 (or 94) of the wild-type Fn3, e.g., human $^{10}$Fn3, domain (SEQ ID NO: 1 or 23) may be modified relative to the corresponding residues in the wild-type sequence. When referring to amino acids at positions further C-terminal to 94 in a $^{10}$Fn3 molecule, it is in the context of a $^{10}$Fn3 molecule that comprises the flexible linker between the $10^{th}$ and $11^{th}$ repeat of the Fn3 domain, i.e., EIDKPSQ (SEQ ID NO: 113), thus forming a 101 amino acid long protein, Thus, SEQ ID NO: 1 linked to EIDKPSQ (SEQ ID NO: 113) at its C-terminus is represented by SEQ ID NO: 23.

```
                                              (SEQ ID NO: 23)
VSDVPRDLEVVAATPTSLLISWDAPAVTVRYYRITYGETGGNSPVQEFT

VPGSKSTATISGLKPGVDYTITVYAVTGRGDSPASSKPISINYRTEIDK

PSQ
```

In certain embodiments, a $^{10}$Fn3 domain comprises modifications in the amino acid sequences of β-strand A, loop AB, β-strand B, loop CD, β-strand E, loop EF, and β-strand F, relative to the sequences of the corresponding regions of the wild-type sequence. These polypeptides are referred to as "south pole binders" or "SP binders" herein. The modified loops and strands contribute to binding to the same target. The amino acid sequence of the CD loop may be extended in length or reduced in length relative to the CD loop of the wild-type Fn3, e.g., human $^{10}$Fn3, domain (SEQ ID NO: 1 or 23). The south pole binders may comprise additional modifications in β-strand G and/or the C-terminal region relative to the sequence of the corresponding region of the wild-type sequence. In exemplary embodiments, the south pole binders may comprise one or more modifications at amino acids corresponding to positions 11, 12, 19, 60, 61, 69, 91, 93 and 95-97 of the wild-type sequence.

In some embodiments, a $^{10}$Fn3 domain comprises modified BC, DE and FG loops, as compared to the corresponding BC, DE and FG loop sequences set forth in SEQ ID NO: 1 or 23, as well as additional modifications in one or more of β-strand C, β-strand D, β-strand F and β-strand G strand residues. The β-strand and loop region modifications together contribute to binding to the target. These proteins are referred to as "Northwest binders", or "NW binders", herein. In exemplary embodiments, the NW binders comprise one or more scaffold modifications at any one of, or combination of, amino acid positions corresponding to scaffold region positions R33, T49, Y73 and S89 of SEQ ID NO: 1 or 23. Suitable modifications in loop and scaffold regions include amino acid substitutions, deletions and/or insertions, or combinations thereof. In certain embodiments, one or more of the BC, DE and FG loops are extended in length or reduced in length, or combinations thereof, relative to the wild-type sequence. In one embodiment, each of the BC, DE and FG loops are extended in length or reduced in length, or combinations thereof, relative to the wild-type sequence (e.g., SEQ ID NO: 1 or 23). In certain embodiments, only a portion of the BC loop is modified, particularly the C-terminal portion, relative to the wild-type sequence. For example, the BC loop may be modified only at amino acid residues corresponding to amino acids 27-31 of the wild-type BC loop, whereas the rest of the BC loop (i.e., corresponding to residues 23-26 of the wild-type loop) are left unmodified.

In some embodiments, a $^{10}$Fn3 domain comprises a modified BC, DE and FG loop as well as one or more additional modifications in any one of, or combination of, the N-terminal region, β-strand A, β-strand B and/or β-strand E. These proteins are referred to as "Northeast binders", or "NE binders", herein. In exemplary embodiments, the NE binders are modified at any one of, or combination of, amino acids corresponding to scaffold region positions 1-7, E9, L19, S21 and/or T58 of the wild-type sequence (SEQ ID NO: 1 or 23). The combination of modified loop and scaffold regions contributes to binding to the target.

In some embodiments, a $^{10}$Fn3 domain comprises modifications in one or more of the AB, CD, DE and EF loops, as well as additional modifications in one or more of β-strand B, β-strand D and/or β-strand E. These proteins are referred to as "South Front binders" herein. The combination of modified loop and strand residues contributes to binding to the target. In exemplary embodiments, a South Front binder may be modified at one or more amino acid positions corresponding to scaffold region positions L19, T49, T58, S60, and/or G61 of SEQ ID NO: 1 or 23 and/or at one or more amino acid positions corresponding to loop region positions T14-S17, P51, T56, G40-E47, and/or K63-G65 of SEQ ID NO: 1 or 23. In exemplary embodiments, a South Front binder may be extended in length or reduced in length in the AB loop, between amino acids corresponding to residues 18 and 20 of the wild-type sequence, and/or in the CD loop.

In some embodiments, a $^{10}$Fn3 domain comprises a modified β-strand A and β-strand G, as compared to the corresponding strand of SEQ ID NO: 1 or 23. These proteins are referred to as "AG Binders" or "AG Strand" binders herein. In certain embodiments, the AG strand binders comprise clusters of modifications at the N-terminal and C-terminal portions of the Fn3, e.g., $^{10}$Fn3, domain, whereas the middle portion of the Fn3 remains unmodified. For example, an AG strand binder may comprise modifications at 16 out of 19 of the first 19 amino acids in the $^{10}$Fn3 domain (i.e., corresponding to amino acid positions 1-19 of SEQ ID NO: 1 or 23) and modifications at 13-17 out of 18 of the last 18 amino acids in the $^{10}$Fn3 domain (i.e., corresponding to amino acid positions 84-101 of SEQ ID NO: 9) or at 14-18 out of 22 of the last 22 amino acids in the $^{10}$Fn3 domain (i.e., corresponding to amino acid positions 80-101 of SEQ ID NO: 9). In exemplary embodiments, an AG binder may comprise modifications at one or more positions corresponding to positions 1-7, 9, 11-17, 19, 84-89 and 91-97 of SEQ ID NO: 9. Preferably the modified regions in an AG binder contribute to binding to the same target.

In some embodiments, a $^{10}$Fn3 domain comprises a modified CD and EF loop, as well as additional modifications in any one of, or combination of residues corresponding to positions 69 or 91-97 of SEQ ID NO: 1 or 23. These proteins are referred to as "Southwest binders", or "SW binders", herein. The modified loop and scaffold regions contribute to binding to the target.

In certain embodiments, proteins comprise a $^{10}$Fn3 domain having reduced immunogenicity, wherein a portion of the BC loop is left as wild-type. Preferably such polypeptides have lower immunogenicity relative to an equivalent polypeptide with modifications in a greater portion of the BC loop. In exemplary embodiments, the N-terminal portion of the BC loop is left as wild-type. For example, the first 1, 2, 3, 4, 5, or 5 residues of the BC loop may be left as wild-type, while the remaining C-terminal residues of the BC loop can be modified. In Fn3 designs having at least a portion of the N-terminal region of the BC loop as wild-type, it may be desirable to leave all or a portion of β-strand B and/or β-strand C unmodified relative to the wild-type sequence as well, particularly the portions of β-strand B and/or β-strand C that are adjacent to the BC loop (i.e., the C-terminal portion of β-strand B and/or the N-terminal portion of β-strand C). In exemplary embodiments, Fn3 domains having the wild-type sequence in an N-terminal portion of the BC loop and reduced immunogenicity may not have any modifications in the N-terminal region, β-strand A, AB loop, and β-strand B. In Fn3 designs with a portion of the BC loop as wild-type, the modified portion of the BC loop may contribute to target binding along with modifications in other regions of the $^{10}$Fn3 domain.

In certain embodiments, proteins comprise a $^{10}$Fn3 domain having reduced immunogenicity, wherein the strong HLA anchor in the region of β-strand B/BC loop/β-strand C (the "BC anchor") has been removed or destroyed (e.g., modified relative to the wild-type sequence in a manner that reduces binding affinity to one or more HLA receptors). For example, the BC anchor may be removed or destroyed by modifying the Fn3, e.g., $^{10}$Fn3, domain at one or more positions corresponding to positions L19, S21, R33 and/or T35 of SEQ ID NO:1. When the BC anchor has been removed or destroyed, it is possible to modify the sequence of the BC loop without significantly increasing the immunogenic potential of the BC region. Accordingly, many such Fn3 designs have modifications in the BC loop in addition to the modifications in β-strand B and/or β-strand C. The BC loop may contribute to target binding, optionally in combination with modifications in other regions of the Fn3 domain. The modifications in β-strand B and/or β-strand C may or may not contribute to target binding.

In exemplary embodiments, an FBS, e.g., a $^{10}$Fn3 domain, binds to a desired target with a $K_d$ of less than 500 nM, 100 nM, 50 nM, 10 nM, 5 nM, 1 nM, 500 pM, 100 pM or less. In some embodiments, the FBS, e.g., $^{10}$Fn3 domain, binds to a desired target with a $K_d$ between 1 pM and 1 μM, between 100 pM and 500 nM, between 1 nM and 500 nM, or between 1 nM and 100 nM. In exemplary embodiments, the $^{10}$Fn3 moiety binds specifically to a target that is not bound by a wild-type $^{10}$Fn3 domain, particularly the wild-type human $^{10}$Fn3 domain having, e.g., SEQ ID NO: 1-8.

In certain embodiments, an FBS moiety comprises an amino acid sequence that is at least 40%, 50%, 60%, 70%, 75%, 80%, 85%, 90%, 95%, 97%, 98%, or 99% identical to an amino acid sequence selected from the group of sequences consisting of SEQ ID NOs: 1-16, and the FBS binds specifically to a target, e.g., with a $K_d$ of less than 500 nM, 100 nM, 50 nM, 10 nM, 5 nM, 1 nM, 500 pM, 100 pM or less. The FBS moiety may comprise amino acid changes (or alterations) in one or more loops and one or more scaffold regions.

In some embodiments, one or more residues of the integrin-binding motif "arginine-glycine-aspartic acid" (RGD) (amino acids 78-80 of SEQ ID NO: 1) may be substituted so as to disrupt integrin binding. In some embodiments, the FG loop of the polypeptides provided herein does not contain an RGD integrin binding site. In one embodiment, the RGD sequence is replaced by a polar amino acid-neutral amino acid-acidic amino acid sequence (in the N-terminal to C-terminal direction). In certain embodiments, the RGD sequence is replaced with SGE or RGE.

In some embodiments, the amino acid sequences of the N-terminal and/or C-terminal regions of an FBS moiety are modified by deletion, substitution or insertion relative to the amino acid sequences of the corresponding regions of $^{10}$Fn3 domains comprising, e.g., SEQ ID NO: 1.

In certain embodiments, the amino acid sequence of the first 1, 2, 3, 4, 5, 6, 7, 8 or 9 residues of SEQ ID NO: 1 may be modified or deleted in the polypeptides provided herein relative to the sequence of the corresponding amino acids in the wild-type human $^{10}$Fn3 domain having SEQ ID NO: 1. In exemplary embodiments, the amino acids corresponding to amino acids 1-7, 8 or 9 of any one of SEQ ID NOs: 1-16 are replaced with an alternative N-terminal region having from 1-20, 1-15, 1-10, 1-8, 1-5, 1-4, 1-3, 1-2, or 1 amino acids in length. Exemplary alternative N-terminal regions include (represented by the single letter amino acid code) M, MG, G, MGVSDVPRDL (SEQ ID NO: 24) and GVSDVPRDL (SEQ ID NO: 25), or N-terminal truncations of any one of SEQ ID NOs: 24 or 25. Other suitable alternative N-terminal regions include, for example, $X_n$SDVPRDL (SEQ ID NO: 26), $X_n$DVPRDL (SEQ ID NO: 27), $X_n$VPRDL (SEQ ID NO: 28), $X_n$PRDL (SEQ ID NO: 29), $X_n$RDL (SEQ ID NO: 30), $X_n$DL (SEQ ID NO: 31), or $X_n$L, wherein n=0, 1 or 2 amino acids, wherein when n=1, X is Met or Gly, and when n=2, X is Met-Gly. When a Met-Gly sequence is added to the N-terminus of a $^{10}$Fn3 domain, the M will usually be cleaved off, leaving a G at the N-terminus. In other embodiments, the alternative N-terminal region comprises the amino acid sequence MASTSG (SEQ ID NO: 32).

As further described herein, in some embodiments, the first seven or eight residues (i.e., residues 1-7 or 1-8) of SEQ ID NO: 1 are deleted, generating a $^{10}$Fn3 domain having the amino acid sequence of, e.g., SEQ ID NO: 8. Additional sequences may also be added to the N- or C-terminus of a $^{10}$Fn3 domain having the amino acid sequence of any one of SEQ ID NOs: 1-16. For example, in some embodiments, the N-terminal extension consists of an amino acid sequence selected from the group consisting of: M, MG, and G. For example, any one of SEQ ID NO: 1-16 may be preceded by M, MG, or G.

In certain embodiments, an FBS moiety is based on an Fn3 repeat other than the 10$^{th}$ repeat of the type III domain of fibronectin, e.g., human fibronectin. For example, an FBS moiety may be similar to any of the other fibronectin type III repeats, e.g., the 1$^{st}$, 2$^{nd}$, 3$^{rd}$, 4$^{th}$, 5$^{th}$, 6$^{th}$, 7$^{th}$, 8$^{th}$, 9$^{th}$, 10$^{th}$, 11$^{th}$, 12$^{th}$, 13$^{th}$, 14$^{th}$, 15$^{th}$, 16$^{th}$, 17$^{th}$, and 18$^{th}$ Fn3 repeats. In yet other embodiments, an FBS moiety may be from a molecule other than fibronectin. Exemplary FBS moieties may be derived from tenascin, a protein that is composed of 15 Fn3 domains with similar sequence similarities to one another as found in fibronectin. These repeats are described, e.g., in Jacobs et al., *Protein Engineering, Design & Selection*, 25:107 (2012). Based on the homology of the repeats in the fibronectin molecule and those in the tenascin molecule, artificial molecules based on these homologies have been created. Proteins comprising a consensus amino acid sequence based on the homology of the domains in the fibronectin molecule are referred to as Fibcon and FibconB (WO 2010/093627 and Jacobs et al. (2012) supra.) and those based on the homology of the domains in the tenascin molecule are referred to as Tencon. An exemplary Fibcon amino acid sequence comprises the following amino acid sequence:

```
MPAPTDLRFTNETPSSLLISWTPPRVQITGYIIRYGPVGSDGRVKEFTV

PPSVSSATITGLKPGTEYTISVIALKDNQESEPLRGRVTTGG
(FibconB; SEQ ID NO: 33),
``` wherein loop AB consists of amino acids 13-16 (TPSS; SEQ ID NO: 34), loop BC consists of amino acids 22-28 (TPPRVQI; SEQ ID NO: 35), loop CD consists of amino acids 38-43 (VGSDGR; SEQ ID NO: 36), loop DE consists of amino acids 51-54 (PSVS; SEQ ID NO: 37), loop EF consists of amino acids 60-64 (GLKPG; SEQ ID NO: 38) and loop FG consist of amino acids 75-81 (KDNQESEP; SEQ ID NO:39). Another Fibcon amino acid sequence comprises the following amino acid sequence:

LDAPTDLQVTNVTDTSITVSWTPPSATITGYRITYTPSNGPGEPKELTVP

PSSTSVTITGITPGVEYVVSVYALKDNQESPPLVGTCTT
(SEQ ID NO: 40; Jacobs et al., supra).

Tenascin derived Fn3 proteins include Tencons (WO 2010/051274, WO 2010/051310 and WO 2011/137319, which are specifically incorporated by reference herein). An exemplary Tencon protein has the following amino acid sequence:

LPAPKNLVVSEVTEDSLRLSWTAPDAAFDSFLIQYQESEKVGEAINLTV

PGSERSYDLTGLKPGTEYTVSIYGVKGGHRSNPLSAEFTT (SEQ ID NO: 41; Jacobs et al., supra, and WO 2011/137319), wherein loop AB consists of amino acids 13-16 (TEDS; SEQ ID NO: 42, loop BC consists of amino acids 22-28 (TAPDAAF; SEQ ID NO: 43), loop CD consists of amino acids 38-43 (SEKVGE; SEQ ID NO: 44), loop DE consists of amino acids 51-54 (GSER; SEQ ID NO: 45), loop EF consists of amino acids 60-64 (GLKPG; SEQ ID NO: 46) and loop FG consists of amino acids 75-81 (KGGHRSN; SEQ ID NO: 47).

A Fibcon, FibconB or Tencon moiety, or target binding variants thereof, whether by themselves or linked to a heterologous moiety may be fused as described herein. Fn3 domains from other proteins, e.g., cell surface hormone and cytokine receptors, chaperonins, and carbohydrate-binding domains, may be conjugated as described herein.

FBS proteins or moieties are described, e.g., in WO 2010/093627, WO 2011/130324, WO 2009/083804, WO 2009/133208, WO 02/04523, WO 2012/016245, WO 2009/023184, WO 2010/051310, WO 2011/020033, WO 2011/051333, WO 2011/051466, WO 2011/092233, WO 2011/100700, WO 2011/130324, WO 2011/130328, WO 2011/137319, WO 2010/051274, WO 2009/086116, WO 09/058379, WO 2013/067029 WO 2012/016245, WO 2014/120891 and WO 2014/043344 (all of which are specifically incorporated by reference herein): any of the FBS proteins or moieties described in these publications may be used as described herein.

In certain embodiments, a protein comprises at least 2 FBS moieties, e.g., the protein comprises a multivalent FBS moiety. For example, a multivalent FBS may comprise 2, 3 or more FBS moieties, e.g., $^{10}$Fn3 domains, that are covalently associated. In exemplary embodiments, the FBS moiety is a bispecific or dimeric protein comprising two $^{10}$Fn3 domains.

The FBS moieties, e.g., $^{10}$Fn3 domains, in a multivalent protein may be connected by a polypeptide linker. Exemplary polypeptide linkers include polypeptides having from 1-20, 1-15, 1-10, 1-8, 1-5, 1-4, 1-3, or 1-2 amino acids. Suitable linkers for joining the $^{10}$Fn3 domains are those which allow the separate domains to fold independently of each other forming a three dimensional structure that permits high affinity binding to a target molecule. Specific examples of suitable linkers include glycine-serine based linkers, glycine-proline based linkers, proline-alanine based linkers as well as any other linkers described herein. In some embodiments, the linker is a glycine-proline based linker. These linkers comprise glycine and proline residues and may be between 3 and 30, 10 and 30, and 3 and 20 amino acids in length. Examples of such linkers include GPG, GPGPGPG (SEQ ID NO: 48) and GPGPGPGPGPG (SEQ ID NO: 49). In some embodiments, the linker is a proline-alanine based linker. These linkers comprise proline and alanine residues and may be between 3 and 30, 10 and 30, 3 and 20 and 6 and 18 amino acids in length. Examples of such linkers include PAPAPA (SEQ ID NO: 50), PAPAPAPAPAPA (SEQ ID NO: 51) and PAPAPAPAPAPAPAPA (SEQ ID NO: 52). In some embodiments, the linker is a glycine-serine based linker. These linkers comprise glycine and serine residues and may be between 8 and 50, 10 and 30, and 10 and 20 amino acids in length. Examples of such linkers include GSGSGSGSGS (($GS)_5$; SEQ ID NO: 53), GSGSGSGSGSGS (($GS)_6$; SEQ ID NO: 54), GSGSGSGSGSGSGSGSGSGS (($GS)_{10}$; SEQ ID NO: 55), GGGGSGGGGSGGGGS (($G_4S)_4$; SEQ ID NO: 56), GGGGSGGGGSGGGGSGGGGSGGGGS (($G_4S)_5$; SEQ ID NO: 57), and GGGGSGGGGSGGGSG (SEQ ID NO: 58). In exemplary embodiments, the linker does not contain any Asp-Lys (DK) pairs.

PmXn Moieties, e.g., Stabilizing Moieties

In certain embodiments, an FBS, e.g., a $^{10}$Fn3 moiety, is linked at its C-terminus to a moiety consisting of PmXn, wherein P is a proline, X is any amino acid, m is an integer that is at least 1 and n is 0 or an integer that is at least 1, and P is N-terminal to X. The PmXn moiety may be linked directly to the C-terminal amino acid of a $^{10}$Fn3 moiety, e.g., to its 94$^{th}$ amino acid (based on amino acid numbering of SEQ ID NO: 1). The PmXn moiety may be linked via a peptide bond to the 94$^{th}$ amino acid of a $^{10}$Fn3 moiety. A PmXn moiety may be linked to a $^{10}$Fn3 moiety having an amino acid sequence that is homologous to that of SEQ ID NO: 1 or comprises, consists essentially of or consists of an amino acid sequence shown in Table 1 or 2. A single proline residue at the end of SEQ ID NO: 1 is referred to as "95Pro" or "Pro95" or "P95" or "95P".

Exemplary $^{10}$Fn3 moieties linked to a PmXn moiety include the following:

(SEQ ID NO: 59)
LEVVAATPTSLLISWDAPAVTVRYYRITYGETGGNSPVQEFTVPGSKSTA

TISGLKPGVDYTITVYAVTGRGDSPASSKPISINYRTPmXn (SEQ ID NO: 60)
VSDVPRDLEVVAATPTSLLISWDAPAVTVRYYRITYGETGGNSPVQEFTV

PGSKSTATISGLKPGVDYTITVYAVTGRGDSPASSKPISINYRTPmXn

In PmXn, m may be 1, 2, 3 or more. For example, m may be 1-3 or m may be 1-2. "n" may be 0, 1, 2, 3 or more, e.g., n may be 1-3 or 1-2.

As further described herein, these $^{10}$Fn3 moieties may be modified to bind to a target (and form FBS moieties), by modifying the amino acid sequence of one or more loop and/or one or more β-strands. FBS moieties that are linked to PmXn are referred to herein as "modified FBS moieties". Accordingly, provided herein are proteins comprising a FBS moiety comprising an amino acid sequence that is at least about 50%, 60%, 70%, 80%, 90%, or 95% identical to SEQ ID NO: 59 or 60, wherein the protein comprises PmXn, and wherein the FBS binds specifically to a target (other than through the RGD domain).

In PmXn, n may be 0, in which case, the C-terminal amino acid of the protein is Pm, e.g., P. In certain embodiments, n is not 0, and may be, e.g., 1, 2, 3, 4, 5, 6, 7, 8, 9, 10 or more. For example, n may be from 0-10, 0-5, 0-3, 1-10, 1-5, 1-3 or 1-2. However, more than 10 amino acids may be linked to the proline. For example, in a tandem FBS moiety or a FBS moiety fused to another polypeptide, the C-terminal amino acid of the FBS moiety may be linked to one or more prolines, and the last proline is linked to the second FBS moiety or to the heterologous moiety. Therefore, in certain embodiments, n may be an integer ranging from 0-100, 0-200, 0-300, 0-400, 0-500 or more.

In certain embodiments, PmXn comprises a cysteine. For example, the first amino acid after the proline may be a cysteine, and the cysteine may be the last amino acid in the molecule or the cysteine may be followed by one or more amino acids. The presence of a cysteine permits the conjugation of heterologous moieties to the FBS moiety, e.g., chemical moieties, e.g., PEG. Exemplary PmXn moieties comprising a cysteine include: PmCXn, wherein C is a cysteine. Another example is $PmXn_1CXn_2$, wherein $n_1$ and $n_2$ are independently 0 or an integer that is at least 1. For example, $n_1$ may be 1 and $n_2$ may be 1, 2, 3, 4 or 5.

Exemplary PmXn moieties include those listed in Table 3.

TABLE 3

Exemplary PmXn moieties

| Moieties with 1 proline | Moieties with 2 prolines |
| --- | --- |
| P | PP |
| PI | PPI |
| PC | PPC |
| PID | PPID (SEQ ID NO: 114) |
| PIE | PPIE (SEQ ID NO: 115) |
| PIDK (SEQ ID NO: 61) | PPIDK (SEQ ID NO: 62) |
| PIEK (SEQ ID NO: 63) | PPIEK (SEQ ID NO: 64) |
| PIDKP (SEQ ID NO: 65) | PPIDKP (SEQ ID NO: 66) |
| PIEKP (SEQ ID NO: 67) | PPIEKP (SEQ ID NO: 68) |
| PIDKPS (SEQ ID NO: 69) | PPIDKPS (SEQ ID NO: 70) |
| PIEKPS (SEQ ID NO: 71) | PPIEKPS (SEQ ID NO: 72) |
| PIDKPC (SEQ ID NO: 73) | PPIDKPC (SEQ ID NO: 74) |
| PIEKPC (SEQ ID NO: 75) | PPIEKPC (SEQ ID NO: 76) |
| PIDKPSQ (SEQ ID NO: 77) | PPIDKPSQ (SEQ ID NO: 78) |
| PIEKPSQ (SEQ ID NO: 79) | PPIEKPSQ (SEQ ID NO: 80) |
| PIDKPCQ (SEQ ID NO: 81) | PPIDKPCQ (SEQ ID NO: 82) |
| PIEKPCQ (SEQ ID NO: 83) | PPIEKPCQ (SEQ ID NO: 84) |
| PHHHHHH (SEQ ID NO: 85) | PPHHHHHH (SEQ ID NO: 86) |
| PCHHHHHH (SEQ ID NO: 87) | PPCHHHHHH (SEQ ID NO: 88) |

Any of the PmXn moieties, e.g., those shown in Table 3 may be followed by a histidine tail, e.g., 6×His tag, or other tag. This does not exclude that a histidine tail may be included in PmXn.

The addition of a PmXn moiety to an FBS moiety enhances one or more characteristics of the FBS moiety. For example, as shown in the Examples, it enhances the thermostability of a $^{10}$Fn3 moiety relative to the moiety that is not linked to a PmXn moiety. The improvement of thermostability is expected to improve other desirable properties such as solubility, proper folding and expression level. For example, as shown in the Example, the presence of a PmXn moiety at the C-terminus of an FBS enhances the solubility of the FBS relative to the FBS that is not linked to a PmXn moiety.

Thus, in certain embodiments, the Tm of an FBS, e.g., a $^{10}$Fn3, moiety is enhanced by at least 1, 2, 3, 4, 5, 6, 7, 8, 9, 10, 11, 12, 13, 14, or 15° C. relative to the FBS moiety that is not linked to a PmXn moiety. For example, the Tm may be increased from 1-30, 1-25, 1-20, 1-15, 1-10, or 1-5° C. relative to the FBS moiety that is not linked to a PmXn moiety. Tm may be measured by Thermal Scanning Fluorescence (TSF), e.g., as follows. Protein samples, e.g., HTPP samples, are normalized to 0.2 mg/ml in PBS. 1 µl of SYPRO® orange dye diluted 1:40 with PBS is added to 25 µl of each sample and the plate is sealed with a clear 96-well microplate adhesive seal. Samples are scanned using a BioRad RT-PCR machine by ramping the temperature from 25° C.-95° C., at a rate of 2 degrees per minute. The data is analyzed using BioRad CFX manager 2.0 software. Tm may also be measured by Differential Scanning calorimetry (DSC) as follows. A 0.5 mg/ml solution is scanned in a VP-Capillary Differential Scanning calorimeter (GE Microcal) by ramping the temperature from 15° C. to 110° C. at a rate of 1 degree per minute under 70 p.s.i pressure. The data is analyzed versus a control run of the appropriate buffer using a best fit using Origin Software (OriginLab Corp).

In certain embodiments, the solubility of an FBS moiety is enhanced by linking it to a PmXn moiety. Such a molecule may exist at a concentration of at least 10 mg/ml, 20 mg/ml, 30 mg/ml, 40 mg/ml, 50 mg/ml, 60 mg/ml, 70 mg/ml, 80 mg/ml, 90 mg/ml or 100 mg/ml.

PKE Moieties

FBS moieties may be linked to PKE moieties to extend the half-life of the FBS moieties. Exemplary PKE moieties include human serum albumin; proteins that bind to human serum albumin (e.g., an FBS binding to HSA or ABD); Fc; or any portion or variant thereof; and PEGs. These moieties may be linked N-terminal or C-terminal to the PmXn moiety and/or the FBS.

Cysteine Conjugated Labels and Therapeutics

In certain embodiments, an FBS moiety linked to a PmXn moiety (and referred to a "modified FBS moiety"), wherein at least one or more the amino acids "X" is a cysteine, is linked through the one or more cysteines, to a heterologous moiety, such as a labeling moiety, a biologically active moiety (e.g., a therapeutic agent) or a binding moiety.

FBS moieties described herein may be conjugated through a C-terminal cysteine to a therapeutic agent to form an immunoconjugate such as an FBS-drug conjugate (FBS-DC; also "adnectin-drug conjugate").

In an FBS-DC, the FBS is conjugated to a drug, with the FBS functioning as a targeting agent for directing the FBS-DC to a target cell expressing its antigen, such as a cancer cell. Preferably, the antigen is a tumor associated antigen, i.e., one that is uniquely expressed or over-expressed by the cancer cell. Once there, the drug is released, either inside the target cell or in its vicinity, to act as a therapeutic agent. For a review on the mechanism of action and use of drug conjugates as used with antibodies, e.g., in cancer therapy, see Schrama et al., *Nature Rev. Drug Disc.*, 5:147 (2006).

Suitable therapeutic agents for use in drug conjugates include antimetabolites, alkylating agents, DNA minor groove binders, DNA intercalators, DNA crosslinkers, histone deacetylase inhibitors, nuclear export inhibitors, proteasome inhibitors, topoisomerase I or II inhibitors, heat shock protein inhibitors, tyrosine kinase inhibitors, antibiotics, and anti-mitotic agents. In an FBS-DC, the FBS and therapeutic agent preferably are conjugated via a linker cleavable such as a peptidyl, disulfide, or hydrazone linker.

More preferably, the linker is a peptidyl linker such as Val-Cit, Ala-Val, Val-Ala-Val, Lys-Lys, Pro-Val-Gly-Val-Val (SEQ ID NO: 89), Ala-Asn-Val, Val-Leu-Lys, Ala-Ala-Asn, Cit-Cit, Val-Lys, Lys, Cit, Ser, or Glu. The FBS-DCs can be prepared according to methods similar to those described in U.S. Pat. Nos. 7,087,600; 6,989,452; and 7,129,261; PCT Publication Nos. WO 02/096910; WO 07/038658; WO 07/051081; WO 07/059404; WO 08/083312; and WO 08/103693; U.S. Patent Publication Nos. 2006/0024317; 2006/0004081; and 2006/0247295; the disclosures of which are incorporated herein by reference. A linker can itself be linked, e.g., covalently linked, e.g., using maleimide chemistry, to a cysteine of the PmXn moiety, wherein at least one X is a cysteine. For example, a linker can be covalently linked to an FBS-PmXn, wherein at least one X is a cysteine. For example, a linker can be linked to an FBS-PmCn, wherein P is a proline, C is a cysteine, and m and n are integers that are at least 1, e.g., 1-3. Ligation to a cysteine can be performed as known in the art using maleimide chemistry (e.g., Imperiali, B. et al., *Protein Engineering: Nucleic Acids and Molecular Biology*, Vol. 22, pp. 65-96, Gross, H. J., ed. (2009)). For attaching a linker to a cysteine on an FBS, the linker may, e.g., comprise a maleinimido moiety, which moiety then reacts with the cysteine to form a covalent bond. In certain embodiments, the amino acids surrounding the cysteine are optimized to facilitate the chemical reaction. For example, a cysteine may be surrounded by negatively charged amino acid for a faster reaction relative to a cysteine that is surrounded by a stretch of positively charged amino acids (EP 1074563).

For cancer treatment, the drug preferably is a cytotoxic drug that causes death of the targeted cancer cell. Cytotoxic drugs that can be used in FBS-DCs include the following types of compounds and their analogs and derivatives:
(a) enediynes such as calicheamicin (see, e.g., Lee et al., *J. Am. Chem. Soc.*, 109:3464, 3466 (1987)) and uncialamycin (see, e.g., Davies et al., WO 2007/038868 A2 (2007) and Chowdari et al., U.S. Pat. No. 8,709,431 B2 (2012));
(b) tubulysins (see, e.g., Domling et al., U.S. Pat. No. 7,778,814 B2 (2010); Cheng et al., U.S. Pat. No. 8,394,922 B2 (2013); and Cong et al., U.S. Publication No. 2014/0227295 A1;
(c) CC-1065 and duocarmycin (see, e.g., Boger, U.S. Pat. No. 6,545,530 B1 (2003); Sufi et al., U.S. Pat. No. 8,461,117 B2 (2013); and Zhang et al., U.S. Publication No. 2012/0301490 A1 (2012));
(d) epothilones (see, e.g., Vite et al., U.S. Publication No. 2007/0275904 A1 (2007) and U.S. Pat. No. RE42,930 E (2011));
(e) auristatins (see, e.g., Senter et al., U.S. Pat. No. 6,844,869 B2 (2005) and Doronina et al., U.S. Pat. No. 7,498,298 B2 (2009));
(f) pyrrolobenzodiazepine (PBD) dimers (see, e.g., Howard et al., U.S. Publication Nos. 2013/0059800 A1 (2013) and 2013/0028919 A1 (2013); and WO 2013/041606 A1 (2013)); and
(g) maytansinoids such as DM1 and DM4 (see, e.g., Chari et al., U.S. Pat. No. 5,208,020 (1993) and Amphlett et al., U.S. Pat. No. 7,374,762 B2 (2008)).

In certain embodiments, an FBS-PmXn, wherein at least one X is a cysteine, is linked to a labeling or detectable moiety for use, e.g., in vitro or in vivo detection or imaging.

Detectable labels can be any of the various types used currently in the field of in vitro diagnostics, including particulate labels including metal sols such as colloidal gold, isotopes such as $I^{125}$ or $Tc^{99}$ presented for instance with a peptidic chelating agent of the $N_2S_2$, $N_3S$ or $N_4$ type, chromophores including fluorescent markers, biotin, luminescent markers, phosphorescent markers and the like, as well as enzyme labels that convert a given substrate to a detectable marker, and polynucleotide tags that are revealed following amplification such as by polymerase chain reaction. A biotinylated antibody would then be detectable by avidin or streptavidin binding. Suitable enzyme labels include horseradish peroxidase, alkaline phosphatase and the like. For instance, the label can be the enzyme alkaline phosphatase, detected by measuring the presence or formation of chemiluminescence following conversion of 1,2 dioxetane substrates such as adamantyl methoxy phosphoryloxy phenyl dioxetane (AMPPD), disodium 3-(4-(methoxyspiro {1,2-dioxetane-3,2'-(5'chloro)tricyclo{3.3.1.1 3,7}decan}-4-yl) phenyl phosphate (CSPD), as well as CDP and CDP-STAR® or other luminescent substrates well-known to those in the art, for example the chelates of suitable lanthanides such as Terbium(III) and Europium(III).

Detectable moieties that may be used include radioactive agents, such as: radioactive heavy metals such as iron chelates, radioactive chelates of gadolinium or manganese, positron emitters of oxygen, nitrogen, iron, carbon, or gallium, $^{18}F$ $^{60}Cu$, $^{61}Cu$, $^{62}Cu$, $^{64}Cu$, $^{124}I$, $^{86}Y$, $^{89}Zr$, $^{66}Ga$, $^{67}Ga$, $^{68}Ga$, $^{44}Sc$, $^{47}Sc$, $^{11}C$, $^{111}In$, $^{114m}In$, $^{114}In$, $^{125}I$, $^{124}I$, $^{131}I$, $^{123}I$, $^{131}I$, $^{123}I$, $^{32}Cl$, $^{33}Cl$, $^{34}Cl$, $^{74}Br$, $^{75}Br$, $^{76}Br$, $^{77}Br$, $^{78}Br$, $^{89}Zr$, $^{186}Re$, $^{188}Re$, $^{86}Y$, $^{90}Y$, $^{177}Lu$, $^{99}Tc$, $^{212}Bi$, $^{213}Bi$, $^{212}Pb$, $^{225}Ac$, or $^{153}Sm$.

The detection means is determined by the chosen label. Appearance of the label or its reaction products can be achieved using the naked eye, in the case where the label is particulate and accumulates at appropriate levels, or using instruments such as a spectrophotometer, a luminometer, a fluorometer, and the like, all in accordance with standard practice.

A detectable moiety may be linked to a cysteine according to methods known in the art. When the detectable moiety is a radioactive agent, e.g., those described further herein, the detectable moiety is linked to an FBS through a chelating agent that is reactive with cysteines, such as a maleimide containing chelating agent, such as maleimide-NODAGA or maleimide-DBCO. Maleimide-NODAGA or maleimide-DBCO can be reacted with a cysteine on the C-terminus of an FBS (e.g., through the PmXn moiety, wherein at least one X is a cysteine), to yield FBS-NODAGA or FBS-DBCO, respectively. Any one of the following chelating agents may be used provided that it comprises, or can be modified to comprise, a reactive moiety that reacts with cysteines: DFO, DOTA and its derivatives (CB-DO2A, 3p-C-DEPA. TCMC, Oxo-DO3A), TE2A, CB-TE2A, CB-TE1A1P, CB-TE2P, MM-TE2A, DM-TE2A, diamsar and derivatives, NODASA, NODAGA, NOTA, NETA, TACN-TM, DTPA, 1B4M-DTPA, CHX-A"-DTPA, TRAP (PRP9), NOPO, AAZTA and derivatives (DATA), $H_2$dedpa, $H_4$octapa, $H_2$azapa, $H_5$decapa, $H_6$phospa, HBED, SHBED, BPCA, CP256, PCTA, HEHA, PEPA, EDTA, TETA, and TRITA based chelating agents, and close analogs and derivatives thereof.

In certain embodiments, an FBS is labeled with a PET tracer and used as an in vivo imaging agent. For example, an FBS may be labeled with the PET tracer $^{64}Cu$. $^{64}Cu$ may be linked to an FBS with a C-terminal cysteine with a chelating agent, such as maleimide-NODAGA.

Exemplary Molecules

In certain embodiments, a protein comprises (i) an FBS moiety comprising an amino acid sequence that is at least about 50%, 60%, 70%, 75%, 80%, 85%, 90%, 95%, 97%, 98%, or 99% identical to any one of SEQ ID NOs: 1-16; and (ii) PmXn, wherein P is a proline, X is any amino acid, m is an integer of at least 1 and n is 0 or an integer of at least 1, wherein the protein binds specifically to a target (e.g., with a $K_d$ of less than 500 nM, 100 nM, 50 nM, 10 nM, 5 nM, 1 nM, 500 pM, 100 pM or less, as determined, e.g., by Surface Plasmon Resonance (SPR), such as Biacore) and wherein the PmXn moiety improves at least one property of the FBS moiety relative to a protein consisting of the unmodified FBS moiety.

In certain embodiments, an enhanced property conferred by a PmXn moiety is enhanced protein stability, e.g., an increase in melting temperature (Tm) of at least 1° C., 2° C., 3° C., 4° C., 5° C., 6° C., 7° C., 8° C., 9° C., 10° C., 11° C., 12° C., 13° C., 14° C., 15° C., 1-15° C., 2-15° C., 3-15° C., 5-15° C., 5-15° C., 1-10° C., 2-10° C., 3-10° C., 4-10° C. or 5-10° C. Tm may be determined, e.g., by Thermal Scanning Fluorescence (TSF) or Differential scanning calorimetry (DSC). "Enhanced Tm" refers to a statistically significant enhancement of the Tm.

In certain embodiments, a protein comprising an FBS moiety and a PmXn moiety is present in a composition, e.g., a pharmaceutical composition, at a concentration of at least 10 mg/ml, 20 mg/ml, 30 mg/ml, 40 mg/ml, 50 mg/ml, 60 mg/ml, 70 mg/ml, 80 mg/ml, 90 mg/ml or 100 mg/ml.

In certain embodiments, a protein comprising an FBS moiety and a PmXn moiety is present in a composition, e.g., a pharmaceutical composition, mostly as a monomer, e.g., at least 80%, 85%, 90%, 95%, 98%, or 99% of the protein in the composition is in monomeric form. Degree of monomericity of a protein solution may be determined by Size Exclusion Chromatography (SEC), e.g., by using a Superdex column (GE Healthcare) on an Agilent 1100 or 1200 HPLC system with UV detection at $A_{214}$ nm and $A_{280}$ nm and with fluorescence detection (excitation=280 nm, emission=350 nm). A buffer of 100 mM sodium sulfate, 100 mM sodium phosphate, 150 mM sodium chloride, (e.g., pH 6.8) at an appropriate flow rate of the SEC column may be employed. Gel filtration standards (Bio-Rad Laboratories, Hercules, Calif.) are used for molecular weight calibration.

In certain embodiments, a protein comprising an FBS moiety and a PmXn moiety has a biological activity that is as least as strong as that of the unmodified FBS moiety. Biological activity can be binding affinity to a target or a biological activity in an assay, e.g., the ability to destroy tumor cells. In certain embodiments, the biological activity of the protein is within 5%, 10%, 25%, 50%, 100%, 2 fold or more of the activity of the unmodified FBS moiety.

A protein comprising an FBS and a PmXn moiety may also comprise a combination of the above characteristics. For example, a protein may be soluble at concentrations of up to 50 mg/ml, be present at least 90% in monomeric form, and/or have a biological activity that is at least as potent as that of the unmodified FBS.

When referring to an enhanced property, the enhancement is a statistically significant enhancement.

Nucleic Acid-Protein Technology

One way to rapidly make and test FBS domains with specific binding properties is the nucleic acid-protein technology of Adnexus, a Bristol-Myers Squibb Company. Such in vitro expression and tagging technology, termed Profusion, that exploits nucleic acid-protein fusions (RNA- and DNA-protein fusions) may be used to identify novel polypeptides and amino acid motifs that are important for binding to proteins. Nucleic acid-protein technology is a technology that covalently couples a protein to its encoding genetic information. For a detailed description of the RNA-protein technology and fibronectin-based scaffold protein library screening methods see Szostak et al., U.S. Pat. Nos. 6,258,558; 6,261,804; 6,214,553; 6,281,344; 6,207,446; 6,518,018; PCT Publication Nos. WO 00/34784; WO 01/64942; WO 02/032925; and Roberts et al., *Proc Natl. Acad. Sci.*, 94:12297-12302 (1997), herein incorporated by reference.

Vectors and Polynucleotides Embodiments

Nucleic acids encoding any of the various proteins comprising an FBS moiety a PmXn moiety disclosed herein may be synthesized chemically, enzymatically or recombinantly. Codon usage may be selected so as to improve expression in a cell. Such codon usage will depend on the cell type selected. Specialized codon usage patterns have been developed for *E. coli* and other bacteria, as well as mammalian cells, plant cells, yeast cells and insect cells. See for example: Mayfield et al., *Proc. Natl. Acad. Sci. USA*, 100 (2):438-442 (Jan. 21, 2003); Sinclair et al., *Protein Expr. Purif.*, 26(1):96-105 (October 2002); Connell, N. D., *Curr. Opin. Biotechnol.*, 12(5):446-449 (October 2001); Makrides et al., *Microbiol. Rev.*, 60(3):512-538 (September 1996); and Sharp et al., Yeast, 7(7):657-678 (October 1991).

General techniques for nucleic acid manipulation are described for example in Sambrook et al., *Molecular Cloning: A Laboratory Manual, Second Edition*, Vols. 1-3, Cold Spring Harbor Laboratory Press (1989), or Ausubel, F. et al., *Current Protocols in Molecular Biology*, Green Publishing and Wiley-Interscience, New York (1987) and periodic updates, herein incorporated by reference. The DNA encoding the polypeptide is operably linked to suitable transcriptional or translational regulatory elements derived from mammalian, viral, or insect genes. Such regulatory elements include a transcriptional promoter, an optional operator sequence to control transcription, a sequence encoding suitable mRNA ribosomal binding sites, and sequences that control the termination of transcription and translation. The ability to replicate in a host, usually conferred by an origin of replication, and a selection gene to facilitate recognition of transformants are additionally incorporated.

The proteins described herein may be produced recombinantly not only directly, but also as a polypeptide with a heterologous polypeptide, which is preferably a signal sequence or other polypeptide having a specific cleavage site at the N-terminus of the mature protein or polypeptide. The heterologous signal sequence selected preferably is one that is recognized and processed (i.e., cleaved by a signal peptidase) by the host cell. For prokaryotic host cells that do not recognize and process a native signal sequence, the signal sequence is substituted by a prokaryotic signal sequence selected, for example, from the group of the alkaline phosphatase, penicillinase, 1pp, or heat-stable enterotoxin II leaders. For yeast secretion the native signal sequence may be substituted by, e.g., the yeast invertase leader, a factor leader (including Saccharomyces and Kluyveromyces alpha-factor leaders), or acid phosphatase leader, the *C. albicans* glucoamylase leader, or the signal described in PCT Publication No. WO 90/13646. In mammalian cell expression, mammalian signal sequences as well as viral secretory leaders, for example, the herpes simplex gD signal, are available. The DNA for such precursor regions may be ligated in reading frame to DNA encoding the protein.

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

A suitable selection gene for use in yeast is the trp1 gene present in the yeast plasmid YRp7 (Stinchcomb et al., Nature, 282:39 (1979)). The trp1 gene provides a selection marker for a mutant strain of yeast lacking the ability to grow in tryptophan, for example, ATCC® No. 44076 or PEP4-1. Jones, Genetics, 85:12 (1977). The presence of the trp1 lesion in the yeast host cell genome then provides an effective environment for detecting transformation by growth in the absence of tryptophan. Similarly, Leu2-deficient yeast strains (ATCC® 20,622 or 38,626) are complemented by known plasmids bearing the Leu2 gene.

Expression and cloning vectors usually contain a promoter that is recognized by the host organism and is operably linked to the nucleic acid encoding the protein. Promoters suitable for use with prokaryotic hosts include the phoA promoter, beta-lactamase and lactose promoter systems, alkaline phosphatase, a tryptophan (trp) promoter system, and hybrid promoters such as the tac promoter. However, other known bacterial promoters are suitable. Promoters for use in bacterial systems also will contain a Shine-Dalgarno (S.D.) sequence operably linked to the DNA encoding the protein.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT (SEQ ID NO: 109) region where N may be any nucleotide. At the 3' end of most eukaryotic genes is an AATAAA (SEQ ID NO: 110) sequence that may be the signal for addition of the poly A tail to the 3' end of the coding sequence. All of these sequences are suitably inserted into eukaryotic expression vectors.

Examples of suitable promoting sequences for use with yeast hosts include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP Patent Publication No. 73,657 and PCT Publication Nos. WO 2011/124718 and WO 2012/059486. Yeast enhancers also are advantageously used with yeast promoters.

Transcription from vectors in mammalian host cells can be controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g., the ACTIN® promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., Nature, 297:598-601 (1982) on expression of human β-interferon cDNA in mouse cells under the control of a thymidine kinase promoter from herpes simplex virus. Alternatively, the rous sarcoma virus long terminal repeat can be used as the promoter.

Transcription of a DNA encoding a protein by higher eukaryotes is often increased by inserting an enhancer sequence into the vector. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, Nature, 297:17-18 (1982) on enhancing elements for activation of eukaryotic promoters. The enhancer may be spliced into the vector at a position 5' or 3' to the polypeptide-encoding sequence, but is preferably located at a site 5' from the promoter.

Expression vectors used in eukaryotic host cells (e.g., yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding the polypeptide. One useful transcription termination component is the bovine growth hormone polyadenylation region. See WO 94/11026 and the expression vector disclosed therein.

The recombinant DNA can also include any type of protein tag sequence that may be useful for purifying the proteins. Examples of protein tags include but are not limited to a histidine tag, a FLAG® tag, a myc tag, an HA tag, or a GST tag. Appropriate cloning and expression vectors for use with bacterial, fungal, yeast, and mammalian cellular hosts can be found in Cloning Vectors: A Laboratory Manual, Elsevier, N.Y. (1985), the relevant disclosure of which is hereby incorporated by reference.

The expression construct may be introduced into the host cell using a method appropriate to the host cell, as will be apparent to one of skill in the art. A variety of methods for introducing nucleic acids into host cells are known in the art, including, but not limited to, electroporation; transfection employing calcium chloride, rubidium chloride, calcium phosphate, DEAE-dextran, or other substances; microprojectile bombardment; lipofection; and infection (where the vector is an infectious agent).

Suitable host cells include prokaryotes, yeast, mammalian cells, or bacterial cells. Suitable bacteria include gram negative or gram positive organisms, for example, *E. coli* or *Bacillus* spp. Yeast, preferably from the *Saccharomyces* species, such as *S. cerevisiae*, may also be used for production of polypeptides. Various mammalian or insect cell culture systems can also be employed to express recombinant proteins. Baculovirus systems for production of heterologous proteins in insect cells are reviewed by Luckow et al. (*Bio/Technology*, 6:47 (1988)). Examples of suitable mammalian host cell lines include endothelial cells, COS-7 monkey kidney cells, CV-1, L cells, C127, 3T3, Chinese hamster ovary (CHO), human embryonic kidney cells, HeLa, 293, 293T, and BHK cell lines. Purified proteins are prepared by culturing suitable host/vector systems to express the recombinant proteins. The FBS protein is then purified from culture media or cell extracts.

Protein Production

Host cells are transformed with the herein-described expression or cloning vectors for protein production and cultured in conventional nutrient media modified as appropriate for inducing promoters, selecting transformants, or amplifying the genes encoding the desired sequences.

The host cells used to produce the proteins may be cultured in a variety of media. Commercially available media such as Ham's F10 (Sigma), Minimal Essential Medium ((MEM), (Sigma)), RPMI-1640 (Sigma), and Dulbecco's Modified Eagle's Medium ((DMEM), (Sigma)) are suitable for culturing the host cells. In addition, any of the media described in Ham et al., Meth. Enzymol., 58:44 (1979), Barnes et al., *Anal. Biochem.*, 102:255 (1980), U.S. Pat. Nos. 4,767,704; 4,657,866; 4,927,762; 4,560,655; or 5,122,469; PCT Publication Nos. WO 90/03430; WO 87/00195; or U.S. Pat. No. RE30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as Gentamycin drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

Proteins disclosed herein can also be produced using cell-free translation systems. For such purposes the nucleic acids encoding the protein must be modified to allow in vitro transcription to produce mRNA and to allow cell-free translation of the mRNA in the particular cell-free system being utilized (eukaryotic such as a mammalian or yeast cell-free translation system or prokaryotic such as a bacterial cell-free translation system).

Proteins can also be produced by chemical synthesis (e.g., by the methods described in *Solid Phase Peptide Synthesis, Second Edition*, The Pierce Chemical Co., Rockford, Ill. (1984)). Modifications to the protein can also be produced by chemical synthesis.

The proteins disclosed herein can be purified by isolation/purification methods for proteins generally known in the field of protein chemistry. Non-limiting examples include extraction, recrystallization, salting out (e.g., with ammonium sulfate or sodium sulfate), centrifugation, dialysis, ultrafiltration, adsorption chromatography, ion exchange chromatography, hydrophobic chromatography, normal phase chromatography, reversed-phase chromatography, gel filtration, gel permeation chromatography, affinity chromatography, electrophoresis, countercurrent distribution or any combinations of these. After purification, proteins may be exchanged into different buffers and/or concentrated by any of a variety of methods known to the art, including, but not limited to, filtration and dialysis.

The purified protein is preferably at least 85% pure, more preferably at least 95% pure, and most preferably at least 98% or 99% pure. Regardless of the exact numerical value of the purity, the protein is sufficiently pure for use as a pharmaceutical product.

Exemplary Uses

Modified FBS proteins may be used for any purpose for which FBS proteins that are not modified by the addition of a PmXn moiety can be used.

In one aspect, the application provides proteins comprising a modified FBS moiety that is useful in the treatment of disorders. The diseases or disorders that may be treated will be dictated by the binding specificity of the FBS moiety. As described herein, modified FBS moieties may be designed to bind to any target of interest. Exemplary targets include, for example, TNF-alpha, VEGFR2, PCSK9, IL-23, EGFR and IGF1R. Merely as an example, modified FBS moieties that bind to TNF-alpha may be used to treat autoimmune disorders such as rheumatoid arthritis, inflammatory bowel disease, psoriasis, and asthma. Modified FBS proteins described herein may also be used for treating cancer.

In certain embodiments, a method for treating a subject having a disease, e.g., cancer, comprises administering to the subject a modified FBS-drug conjugate.

Provided herein are methods for administering proteins to a subject. In some embodiments, the subject is a human. In some embodiments, the proteins are pharmaceutically acceptable to a mammal, in particular a human. A "pharmaceutically acceptable" composition refers to a composition that is administered to an animal without significant adverse medical consequences. Examples of pharmaceutically acceptable compositions include compositions comprising FBS moieties that lack the integrin-binding domain (RGD) and compositions that are essentially endotoxin or pyrogen free or have very low endotoxin or pyrogen levels.

Other uses of the modified FBS proteins described herein include their use in in vitro or in vivo detection assays. For example, they may be used for detecting a target molecule in a sample. A method may comprise contacting the sample with a modified FBS described herein, wherein said contacting is carried out under conditions that allow FBS-target complex formation; and detecting said complex, thereby detecting said target in said sample. Detection may be carried out using any art-recognized technique, such as, e.g., radiography, immunological assay, fluorescence detection, mass spectroscopy, or surface plasmon resonance. The sample may be from a human or other mammal. For diagnostic purposes, appropriate agents are detectable labels that include radioisotopes, for whole body imaging, and radioisotopes, enzymes, fluorescent labels and other suitable antibody tags for sample testing.

In certain embodiments, the modified FBS described herein are useful in a variety of diagnostic and imaging applications. In certain embodiments, a modified FBS is labeled with a moiety that is detectable in vivo and such labeled FBS may be used as in vivo imaging agents, e.g., for whole body imaging. For example, in one embodiment, a method for detecting a tumor comprising a given antigen in a subject comprises administering to the subject a modified FBS linked to a detectable label, and following an appropriate time, detecting the label in the subject.

An FBS imaging agent may be used to diagnose a disorder or disease associated with increased levels of a given antigen, for example, a cancer in which a tumor selectively overexpresses the antigen. In a similar manner, a modified FBS that binds specifically to a given antigen can be used to monitor antigen levels in a subject being treated for a condition associated with the antigen. The modified FBS may be used with or without modification, and may be labeled by covalent or non-covalent attachment of a detectable moiety.

Formulation and Administration

The application further provides pharmaceutically acceptable compositions comprising the proteins described herein, wherein the composition is essentially endotoxin and/or pyrogen free.

Therapeutic formulations comprising proteins are prepared for storage by mixing the described proteins having the desired degree of purity with optional physiologically acceptable carriers, excipients or stabilizers (Osol, A., ed., *Remington's Pharmaceutical Sciences,* 16th Edition (1980)), in the form of aqueous solutions, lyophilized or other dried formulations. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyidimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g., Zn-protein complexes); and/or non-ionic surfactants such as Tween, PLURONIC® or polyethylene glycol (PEG).

The formulations herein may also contain more than one active compounds as necessary for the particular indication being treated, preferably those with complementary activities that do not adversely affect each other. Such molecules are suitably present in combination in amounts that are effective for the purpose intended.

The proteins may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Osol, A., ed., *Remington's Pharmaceutical Sciences,* 16th Edition (1980).

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the proteins described herein, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and y ethyl-L-glutamate, non-degradable ethylene-vinyl acetate, degradable lactic acid-glycolic acid copolymers such as the LUPRON DEPOT® (injectable microspheres composed of lactic acid-glycolic acid copolymer and leuprolide acetate), and poly-D-(–)-3-hydroxybutyric acid. While polymers such as ethylene-vinyl acetate and lactic acid-glycolic acid enable release of molecules for over 100 days, certain hydrogels release proteins for shorter time periods. When encapsulated proteins remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

While the skilled artisan will understand that the dosage of each protein will be dependent on the identity of the protein, the preferred dosages can range from about 10 mg/square meter to about 2000 mg/square meter, more preferably from about 50 mg/square meter to about 1000 mg/square meter.

For therapeutic applications, the proteins are administered to a subject, in a pharmaceutically acceptable dosage form. They can be administered intravenously as a bolus or by continuous in over a period of time, by intramuscular, subcutaneous, intra-articular, intrasynovial, intrathecal, oral, topical, or inhalation routes. The protein may also be administered by intratumoral, peritumoral, intralesional, or perilesional routes, to exert local as well as systemic therapeutic effects. Suitable pharmaceutically acceptable carriers, diluents, and excipients are well known and can be determined by those of skill in the art as the clinical situation warrants. Examples of suitable carriers, diluents and/or excipients include: (1) Dulbecco's phosphate buffered saline, pH about 7.4, containing about 1 mg/ml to 25 mg/ml human serum albumin, (2) 0.9% saline (0.9% w/v NaCl), and (3) 5% (w/v) dextrose. The methods of the present invention can be practiced in vitro, in vivo, or ex vivo.

Administration of proteins, and one or more additional therapeutic agents, whether co-administered or administered sequentially, may occur as described above for therapeutic applications. Suitable pharmaceutically acceptable carriers, diluents, and excipients for co-administration will be understood by the skilled artisan to depend on the identity of the particular therapeutic agent being co-administered.

When present in an aqueous dosage form, rather than being lyophilized, the protein typically will be formulated at a concentration of about 0.1 mg/ml to 100 mg/ml, although wide variation outside of these ranges is permitted. For the treatment of disease, the appropriate dosage of proteins will depend on the type of disease to be treated, the severity and course of the disease, whether the proteins are administered for preventive or therapeutic purposes, the course of previous therapy, the patient's clinical history and response to the fusion, and the discretion of the attending physician. The protein is suitably administered to the patient at one time or over a series of treatments.

Exemplary Embodiments

1. An isolated fibronectin based scaffold (FBS) protein that specifically binds to a target, wherein the FBS is a non-naturally occurring FBS, and wherein the FBS is linked at its C-terminus to a moiety consisting of the amino acid sequence PmXn, wherein P is proline, X is any amino acid, m is an integer that is at least 1 and n is 0 or an integer that is at least 1, and wherein the PmXn moiety provides an enhanced property to the FBS protein relative to the FBS protein that is not linked to the PmXn moiety.
2. The isolated FBS protein of embodiment 1, wherein the moiety consists of P (m is 1 and n is 0).
3. The isolated FBS protein of embodiment 1, wherein the moiety consists of PP (m is 2 and n is 0).
4. The isolated FBS protein of embodiment 1, wherein the moiety consists of PmXn, wherein n is 1-150.
5. The isolated FBS protein of embodiment 1, wherein the moiety consists of PmXn, wherein n is 1-10.
6. The isolated FBS protein of embodiment 1, wherein the moiety consists of PmXn, wherein n is 1-5.
7. The isolated FBS protein of embodiment 1, wherein the moiety consists of PI, PC, PID, PIE, PIDK (SEQ ID NO: 61), PIEK (SEQ ID NO: 63), PIDKP (SEQ ID NO: 65), PIEKP (SEQ ID NO: 67), PIDKPS (SEQ ID NO: 69), PIEKPS (SEQ ID NO: 71), PIDKPC (SEQ ID NO: 73), PIEKPC (SEQ ID NO: 75), PIDKPSQ (SEQ ID NO: 77), PIEKPSQ (SEQ ID NO: 79), PIDKPCQ (SEQ ID NO: 81), PIEKPCQ (SEQ ID NO: 83), PHHHHHH (SEQ ID NO: 87) or PCHHHHHH (SEQ ID NO: 86).
8. The isolated FBS protein of any one of embodiments 1-7, wherein the FBS protein is an Fn3 protein.
9. The isolated FBS protein of embodiment 8, wherein the Fn3 protein is a $^{10}$Fn3 protein.
10. The isolated FBS protein of embodiment 9, wherein the $^{10}$Fn3 protein is a human $^{10}$Fn3 protein.
11. The isolated FBS protein of any one of embodiments 1-10, comprising an amino acid sequence that is at least 50% identical to SEQ ID NO: 1.
12. The isolated FBS protein of any one of embodiments 1-11, comprising at least one amino acid mutation in at least one loop or one scaffold region.
13. The isolated FBS protein of any one of embodiments 1-12, comprising the amino acid sequence VSD-VPRDLEVVAA(X)$_u$LLISW(X)$_v$YRITY(X)$_w$FTV(X)$_x$ATISGL(X)$_y$YTITVY A(X)$_z$ISINYRT (SEQ ID NO: 9), wherein (X)$_u$, (X)$_v$, (X)$_w$, (X)$_x$, (X)$_y$ and (X)$_z$ consist of the wild-type amino acid sequence (SEQ ID NO: 1) or comprise at least one amino acid difference with the corresponding wild-type sequence, and the sequence optionally comprises from 1-10 scaffold, N-terminal and/or C-terminal mutations.
14. The isolated FBS protein of any one of embodiments 1-13, comprising an amino acid sequence that is at least 50% identical to SEQ ID NO: 1, and wherein the C-terminal amino acid residue of the FBS protein is fused to a moiety consisting of PmXn, wherein the FBS protein binds specifically to a target with a Kd of less than 500 nM, which target is not bound by a wild-type $^{10}$Fn3 molecule comprising SEQ ID NO: 1.
15. The isolated FBS protein of embodiment 14, comprising an amino acid sequence that is at least 70% identical to SEQ ID NO: 1.
16. The isolated FBS protein of any one of embodiments 1-15, wherein the moiety consisting of PmXn is linked to the C-terminal amino acid residue of the FBS protein through a peptide bond.
17. The isolated FBS protein of any one of embodiments 1-16, wherein PmXn is P or PC.
18. The isolated FBS protein of any one of embodiments 1-17, comprising an amino acid sequence that is at least 60% identical to SEQ ID NO: 1, and wherein the C-terminal amino acid residue of the FBS protein is linked to a proline through a peptide bond, and wherein the FBS protein binds specifically to a target with a Kd of less than 500 nM, which target is not bound by a wild-type $^{10}$Fn3 molecule comprising SEQ ID NO: 1.
19. The isolated FBS protein of any of embodiments 1-18, wherein at least one X of PmXn is a cysteine and wherein the cysteine
20. The isolated FBS protein of embodiment 19, wherein the cysteine is conjugated to a heterologous moiety.
21. The isolated FBS protein of embodiment 20, wherein the heterologous molecule is a detectable moiety.
22. The isolated FBS protein of embodiment 20 or 21, wherein the heterologous molecule is a drug moiety and the drug moiety and the FBS form an FBS-drug conjugate.
23. The isolated FBS protein of any one of embodiments 1-22, wherein the enhanced property conferred by the PmXn moiety is enhanced stability.
24. The isolated FBS protein of embodiment 23, wherein enhanced stability is an increase in Tm of at least 1° C., 2° C., 3° C., 4° C., 5° C. or more.

The following representative Examples contain important additional information, exemplification and guidance which can be adapted to the practice of this invention in its various embodiments and the equivalents thereof. These examples are intended to help illustrate the invention, and are not intended to, nor should they be construed to, limit its scope.

EXAMPLES

Example 1: Thermostability Enhancement by Adding a Proline at the C-terminus of $^{10}$Fn3 Molecules In nature, $^{10}$Fn3 is a part of a long string of fibronectin type III domains; the domain immediately downstream of $^{10}$Fn3 is named $^{11}$Fn3. The sequence below shows the wild-type sequences of the $^{10}$Fn3 (in italics) and $^{11}$Fn3 (in bold) domains and the junction between them (underlined).

(SEQ ID NO: 90)
VSDVPRDLEVVAATPTSLLISWDAPAVTVRYYRITYGETGGNSPVQEFTV

PGSKSTATISGLKPGVDYTITVYAVTGRGDSPASSKPISINYRTEIDKPS

QMQVTDVQDNSISVKWLPSSSPVTGYRVTTTPKNGPGPTKTKTAGPDQTE

MTIEGLQPTVEYVVSVYAQNPSGESQPLVQTAVT

Based on the crystal and NMR structures of ¹⁰Fn3 and of the sequence alignment between ¹⁰Fn3 and ¹¹Fn3 (Dickinson et al., "Crystal structure of the tenth type III cell adhesion module of human fibronectin", *J. Mol. Biol.*, 36:1079-1092 (1994)), the first two residues of this sequence, RT, are part of the final beta strand of ¹⁰Fn3 ("strand G"), and the remainder of the sequence, EIDKPSQ (SEQ ID NO: 113), is a flexible linker between structured tenth and eleventh fibronectin type III domains.

The C-terminus of engineered protein domains based on ¹⁰Fn3 is often modified from the wild-type sequence to facilitate its cloning, expression, and purification. During a survey of different engineered C-termini of Adnectins it was found that a mutation from RTE to RTP has led to increased thermostability of several different Adnectins. Table 4 lists different C-termini used in this study.

TABLE 4

Wild-type linker between ¹⁰Fn3 and ¹¹Fn3 and the engineered Adnectin C-terminal sequences that were compared in this study. The "short engineered C-terminus with P and His-tag" and the "short engineered C-terminus with PC" contain the RTE to RTP mutation.

| Descriptor | Sequence | Purpose | Comments |
| --- | --- | --- | --- |
| Wild-type junction between ¹⁰Fn3 and ¹¹Fn3 | RTEIDKPSQ (SEQ ID NO: 91) | natural human sequence | contains RTE |
| Long engineered C-terminus with His-tag | RTEIEKPSQH₆ (SEQ ID NO: 92) | H₆ allows purification by metal-chelate chromatography | contains RTE; DK->EK mutation reduced sensitivity to proteases |
| Short engineered C-terminus with P and His-tag | RTPH6 (SEQ ID NO: 93) | H₆ allows purification by metal-chelate chromatography | contains RTP |
| Short engineered C-terminus with EC | RTEC (SEQ ID NO: 94) | C allows site-specific modification using maleimide chemistry | contains RTE; no purification tag |
| Short engineered C-terminus with PC | RTPC (SEQ ID NO: 95) | C allows site-specific modification using maleimide chemistry | contains RTP; no purification tag |

The effect of the mutation from RTE to RTP on thermostability of Adnectins was tested by comparing several pairs of Adnectins that differed in their C-termini. Table 5 describes the pairs of Adnectins used in this study, including their names, targets, and thermodynamic properties. Adnectin 1 is an Adnectin that binds to target X. All the Adnectins listed were selected from high-complexity libraries using PROfusion (mRNA-display) technology, and had their C-termini re-engineered by site-directed mutagenesis. Full protein sequences are set forth below.

TABLE 5

Clone name, C-terminus, target, and melting temperature (as determined by differential scanning calorimetry at 0.5 mg/mL, in PBS, pH 7.4). Adnectins PRD-1414 and PRD-1417 were conjugated to 40 kDa, 2-branched PEG (NOF, Cat. #GL2-400MA01)

| Protein ID (RTE) C-terminus | Protein ID (RTP) C-terminus | Target | $T_m$ (RTE) | $T_m$ (RTP) | Increase in $T_m$ of RTP- over RTE-containing protein |
| --- | --- | --- | --- | --- | --- |
| ADX_2382_D09 RTEIEKPSQH₆ (SEQ ID NO: 92) | ADX_5484_A03 RTPH₆ (SEQ ID NO: 93) | PCSK9 | 84° C. | 87° C. | +3° C. |
| ADX_2987_H07 RTEIEKPSQH₆ (SEQ ID NO: 92) | ADX_5484_A04 RTPH₆ (SEQ ID NO: 93) | Myostatin | 56° C. | 57° C. | +1° C. |
| PRD-1414 RTEC-PEG (SEQ ID NO: 94) | PRD-1417 RTPC-PEG (SEQ ID NO: 95) | PCSK9 | 64° C. | 76° C. | +12° C. |

TABLE 5-continued

Clone name, C-terminus, target, and melting temperature (as determined by differential scanning calorimetry at 0.5 mg/mL, in PBS, pH 7.4). Adnectins PRD-1414 and PRD-1417 were conjugated to 40 kDa, 2-branched PEG (NOF, Cat. #GL2-400MA01)

| Protein ID (RTE) C-terminus | Protein ID (RTP) C-terminus | Target | $T_m$ (RTE) | $T_m$ (RTP) | Increase in $T_m$ of RTP- over RTE-containing protein |
|---|---|---|---|---|---|
| Adnectin 1 RTEIEKPSQH$_6$ (SEQ ID NO: 94) | Adnectin 1 RTPH$_6$ (SEQ ID NO: 95) | X | 61° C. | 64° C. 72° C. | +3° C., 11° C. |

Amino acid sequences of proteins used in this Example:

ADX_238_D09:
(SEQ ID NO: 96)
MGVSDVPRDLEVVAATPTSLLISWDAPAEGYGYYRITYGETGGNSPVQE

FTVPVSKGTATISGLKPGVDYTITVYAVEFDFPGAGYYHRPISINYRTE

IDKPSQHHHHHH*

ADX_5484_A03:
(SEQ ID NO: 97)
MGVSDVPRDLEVVAATPTSLLISWDAPAEGYGYYRITYGETGGNSPVQE

FTVPVSKGTATISGLKPGVDYTITVYAVEFDFPGAGYYHRPISINYRTP

HHHHHH*

ADX_2987_H07:
(SEQ ID NO: 97)
MGVSDVPRDLEVVAATPTSLLISWTLPHAGRAHYYRITYGETGGNSPVQ

EFTVPGRGVTATISGLKPGVDYTITVYAVTVTTTKVIHYKPISINYRTE

IDKPSQHHHHHH*

ADX_5484_A04:
(SEQ ID NO: 98)
MGVSDVPRDLEVVAATPTSLLISWTLPHAGRAHYYRITYGETGGNSPVQ

EFTVPGRGVTATISGLKPGVDYTITVYAVTVTTTKVIHYKPISINYRTP

HHHHHH*

PRD-1414:
(SEQ ID NO: 99)
MGVSDVPRDLEVVAATPTSLLISWDAPAEGYGYYRITYGETGGNSPVQE

FTVPVSKGTATISGLKPGVDYTITVYAVEFDFPGAGYYHRPISINYRTE

C*

PRD-1417:
(SEQ ID NO: 100)
MGVSDVPRDLEVVAATPTSLLISWDAPAEGYGYYRITYGETGGNSPVQE

FTVPVSKGTATISGLKPGVDYTITVYAVEFDFPGAGYYHRPISINYRTP

C*

The "*" in each sequence above denotes the stop codon, and the C-terminus of each Adnectin.

The N-terminal M was removed during bacterial expression of each protein. The C residues in purified PRD-1414 and PRD-1417 protein were conjugated to PEG before characterization of each protein.

As shown in Table 5, Adnectins with C-termini that contain a proline in place of the wild-type glutamic acid at the C-terminus (RTE to RTP mutation) show a higher thermostability. This increase in stability was observed for several examples when a longer C-terminus modeled on the natural linker between human $^{10}$Fn3 and $^{11}$Fn3 was replaced with a shorter engineered C-terminus containing only the proline and a hexahistidine purification tag. Enhanced thermostability was also observed in a $^{10}$Fn3 protein having a short engineered C-terminus and a polyethylene glycol (PEG) upon the addition of a C-terminal proline. The increase in stability may be attributed to the presence of a proline in this specific position.

Example 2: Stabilization of a Second PCSK9 Adnectin with a C-terminal Proline

This Example shows that the thermostability of another PCSK9 adnectin molecule is also enhanced by the addition of a C-terminal proline.

In this Example, the C-terminus of pegylated (40 kDa branched PEG) PCSK9 adnectin ADX_2013_E01 was modified from NYRTEIEKPCQ (SEQ ID NO: 101) to NYRTPC (SEQ ID NO: 102) and thermostability measured by TSF. The amino acid sequence of this adnectin is provided in WO 2011/130354. The results indicate that the pegylated adnectin with the NYRTEIEKPCQ (SEQ ID NO: 101) C-terminus has a Tm of 70° C., whereas the pegylated adnectin with the NYRTPC (SEQ ID NO: 102) C-terminus has a Tm of 76° C.

Thus, the thermostability of this PCSK9 adnectin is enhanced by 6° C. by the presence of a C-terminal proline.

Example 3: Comparison of Various C-termini on Thermostability

This Example shows a comparison of the thermostability of adnectins with or without a proline at their C-terminus as well as adnectins having 2 prolines at their C-terminus.

Two of the adnectins described in Example 1 (ADX_2392_D09 binding to PCSK9 and ADX_2987_H07 binding to myostatin) and one additional Adnectin binding to a different target (Adnectin 1, binding to target X) were modified at their C-terminus, as indicated in Table 6, and their thermostability and % monomer were determined. An Adnectin ("Adnectin 1") to a different target (X) was also modified with the same C-terminal sequences. Thermostability was determined by TSF and % Monomer was determined by SEC.

TABLE 6

Percent monomer and thermostability of adnectins with various C-termini

| Parent | C-term. | | | |
|---|---|---|---|---|
| | NYRTEIEKPSQH$_6$ (SEQ ID NO: 103) | NYRTH$_6$ (SEQ ID NO: 104) | NYRTPH$_6$ (SEQ ID NO: 105) | NYRTPPH$_6$ (SEQ ID NO: 106) |
| ADX_2392_D09 | >99% | >99% | >99% | 99% |
| PCSK9 | 84° C. | 83° C. | 87° C. | 87° C. |
| ADX_2987_H07 | 99% | >99% | >99% | >99% |
| Myostatin | 56° C. | 51° C. | 57° C. | 57° C. |
| Adnectin 1 | ~8% | >99% | >98% | >98% |
| Target X | 61° C. | 58° C. | 64° C., 72° C. | 64° C., 72° C. |

The results, which are set forth in Table 6, show that the identity of the C-terminus has no significant effect on the % monomer, however, it has an effect on the melting temperature (Tm). As described in Example 1, NYRTPH$_6$ (SEQ ID NO: 105) increases the thermostability relative to NYRTH$_6$ (SEQ ID NO: 104) for both adnectins: by 4° C. for the PCSK9 adnectin and by 6° C. for the myostatin adnectin. In addition, the presence of a second proline provides a stabilizing effect that is similar to that provided by a single proline.

Thus, the presence of one or two C-terminal prolines enhances the thermostability of adnectins relative to the same molecule without the C-terminal proline(s).

Example 4: Addition of a C-terminal Proline Enhances Solubility

This Example demonstrates that the presence of a C-terminal proline enhances the solubility of a tandem adnectin relative to the same tandem adnectin without the C-terminal proline.

A tandem adnectin, i.e., two adnectins each binding to a different target linked by a linker, and containing either an NYRTE (SEQ ID NO: 107) C-terminus or an NYRTP (SEQ ID NO: 108) C-terminus were expressed in E. coli BLR cells and fermented at 30° C. The titer of the tandem without the proline was 1.2 g/L soluble protein and 2.8 g/L of total protein, indicating that the expressed protein was 43% soluble. The titer of the tandem with the proline was 2.56 g/L soluble and 2.61 g/L total. Even after renaturing the insoluble fraction of the tandem without the proline, and obtaining a solution that was 98% pure and monomeric at 2.5 mg/mL, this protein composition did not show significant binding to its target, suggesting that it may not be properly refolded.

Thus, considering that the only difference between the two proteins was the presence of an E versus a P at the C-terminus, the results suggests that the presence of a proline provides enhanced solubility of the tandem.

The entire disclosure of each document cited (including patents, patent applications, journal articles, abstracts, laboratory manuals, books, GENBANK® Accession numbers, SWISS-PROT® Accession numbers, or other disclosures) in the Background, Detailed Description, Brief Description of the Drawings, and Examples is hereby incorporated herein by reference in their entirety.

The present invention is not to be limited in scope by the embodiments disclosed herein, which are intended as single illustrations of individual aspects of the invention, and any that are functionally equivalent are within the scope of the invention. Various modifications to the models and methods of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention.

The invention claimed is:

1. An isolated fibronectin based scaffold (FBS) protein comprising a $^{10}$Fn3 domain, wherein the $^{10}$Fn3 domain comprises an amino acid sequence that is at least 70% identical to SEQ ID NO: 1, wherein
   (i) the C-terminal amino acid at the position corresponding to position 94 of SEQ ID NO:1 is covalently linked through a peptide bond to a moiety consisting of the amino acid sequence PmXn, wherein P is proline, X is any amino acid, m is an integer that is at least 1 and n is 0 or an integer that is at least 1; and
   (ii) the PmXn moiety provides an enhanced property to the FBS protein relative to the FBS protein that is not linked to the PmXn moiety.

2. The isolated FBS protein of claim 1, wherein the moiety consists of P (m is 1 and n is 0).

3. The isolated FBS protein of claim 1, wherein the moiety consists of PP (m is 2 and n is 0).

4. The isolated FBS protein of claim 1, wherein the moiety consists of PmXn, wherein n is 1-150.

5. The isolated FBS protein of claim 1, wherein the moiety consists of PmXn, wherein n is 1-10.

6. The isolated FBS protein of claim 1, wherein the moiety consists of PmXn, wherein n is 1-5.

7. The isolated FBS protein of claim 1, wherein the PmXn moiety consists of PI, PC, PID, PIE, PIDK (SEQ ID NO: 61), PIEK (SEQ ID NO: 63), PIDKP (SEQ ID NO: 65), PIEKP (SEQ ID NO: 67), PIDKPS (SEQ ID NO: 69), PIEKPS (SEQ ID NO: 71), PIDKPC (SEQ ID NO: 73), PIEKPC (SEQ ID NO: 75), PIDKPSQ (SEQ ID NO: 77), PIEKPSQ (SEQ ID NO: 79), PIDKPCQ (SEQ ID NO: 81), PIEKPCQ (SEQ ID NO: 83), PHHHHHH (SEQ ID NO: 87) or PCHHHHHH (SEQ ID NO: 86).

8. The isolated FBS protein of any one of claim 1-7, comprising the amino acid sequence LEVVAA(X)uLLISW (X)vYRITY(X)wFTV(X)xATISGL(X)yYTITVY A(X)ZIS-INYRT (SEQ ID NO: 16), wherein (X)u, (X)v, (X)w, (X)x, (X)y and (X)z consist of the wild-type amino acid sequence (SEQ ID NO: 1) or comprise at least one amino acid difference with the corresponding wild-type sequence.

9. The isolated FBS protein of claim 1, wherein PmXn is P or PC.

10. The isolated FBS protein of claim 1, wherein at least one X of PmXn is a cysteine.

11. The isolated FBS protein of claim 10, wherein the cysteine is conjugated to a heterologous moiety.

12. The isolated FBS protein of claim 11, wherein the heterologous molecule is a detectable moiety.

13. The isolated FBS protein of claim 11 or 12, wherein the heterologous molecule is a drug moiety and the drug moiety and the FBS form an FBS-drug conjugate.

14. The isolated FBS protein of claim 1, wherein the enhanced property conferred by the PmXn moiety is enhanced stability.

15. The isolated FBS protein of claim 14, wherein enhanced stability is an increase in Tm of at least 1° C., 2° C., 3° C., 4° C., 5° C. or more.

16. The isolated FBS protein of claim 10, wherein the PmXn moiety is PmCXn or PmXn$_1$CXn$_2$, wherein C is cysteine and n$_1$ and n$_2$ are independently 0 or an integer that is at least 1.

17. The isolated FBS protein of claim 16, wherein the cysteine is conjugated to a heterologous moiety.

18. The isolated FBS protein of claim 17, wherein the heterologous molecule is a detectable moiety.

19. The isolated FBS protein of claim 9, wherein PmXn is P.

20. The isolated FBS protein of claim 9, wherein PmXn is PC.

* * * * *

UNITED STATES PATENT AND TRADEMARK OFFICE
CERTIFICATE OF CORRECTION

| | |
|---|---|
| PATENT NO. | : 10,450,363 B2 |
| APPLICATION NO. | : 15/127183 |
| DATED | : October 22, 2019 |
| INVENTOR(S) | : Dasa Lipovsek |

It is certified that error appears in the above-identified patent and that said Letters Patent is hereby corrected as shown below:

In the Claims

At Column 113, Claim number 8, Line number 66:
Immediately after "any one of" delete "claim" and insert -- claims --.

At Column 114, Claim number 8, Line number 33:
Delete "(X)vYRITY(X)wFTV(X)xATISGL(X)yYTITVY A(X)ZIS-" and insert
-- (X)vYRITY(X)wFTV(X)xATISGL(X)yYTITVYA(X)ZIS- --.

Signed and Sealed this
Third Day of November, 2020

Andrei Iancu
*Director of the United States Patent and Trademark Office*

SEQUENCE LISTING

```
<160> NUMBER OF SEQ ID NOS: 130

<210> SEQ ID NO 1
<211> LENGTH: 94
<212> TYPE: PRT
<213> ORGANISM: Homo sapiens

<400> SEQUENCE: 1

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Glu Thr Gly Gly Asn Ser Pro Val Gln Glu Phe
        35                  40                  45

Thr Val Pro Gly Ser Lys Ser Thr Ala Thr Ile Ser Gly Leu Lys Pro
    50                  55                  60

Gly Val Asp Tyr Thr Ile Thr Val Tyr Ala Val Thr Gly Arg Gly Asp
65                  70                  75                  80
```

Ser Pro Ala Ser Ser Lys Pro Ile Ser Ile Asn Tyr Arg Thr
                85                  90

<210> SEQ ID NO 2
<211> LENGTH: 93
<212> TYPE: PRT
<213> ORGANISM: Homo sapiens

<400> SEQUENCE: 2

Ser Asp Val Pro Arg Asp Leu Glu Val Val Ala Ala Thr Pro Thr Ser
1               5                   10                  15

Leu Leu Ile Ser Trp Asp Ala Pro Ala Val Thr Val Arg Tyr Tyr Arg
            20                  25                  30

Ile Thr Tyr Gly Glu Thr Gly Gly Asn Ser Pro Val Gln Glu Phe Thr
        35                  40                  45

Val Pro Gly Ser Lys Ser Thr Ala Thr Ile Ser Gly Leu Lys Pro Gly
    50                  55                  60

Val Asp Tyr Thr Ile Thr Val Tyr Ala Val Thr Gly Arg Gly Asp Ser
65                  70                  75                  80

Pro Ala Ser Ser Lys Pro Ile Ser Ile Asn Tyr Arg Thr
                85                  90

<210> SEQ ID NO 3
<211> LENGTH: 92
<212> TYPE: PRT
<213> ORGANISM: Homo sapiens

<400> SEQUENCE: 3

Asp Val Pro Arg Asp Leu Glu Val Val Ala Ala Thr Pro Thr Ser Leu
1               5                   10                  15

Leu Ile Ser Trp Asp Ala Pro Ala Val Thr Val Arg Tyr Tyr Arg Ile
            20                  25                  30

Thr Tyr Gly Glu Thr Gly Gly Asn Ser Pro Val Gln Glu Phe Thr Val
        35                  40                  45

Pro Gly Ser Lys Ser Thr Ala Thr Ile Ser Gly Leu Lys Pro Gly Val
    50                  55                  60

Asp Tyr Thr Ile Thr Val Tyr Ala Val Thr Gly Arg Gly Asp Ser Pro
65                  70                  75                  80

Ala Ser Ser Lys Pro Ile Ser Ile Asn Tyr Arg Thr
                85                  90

<210> SEQ ID NO 4
<211> LENGTH: 91
<212> TYPE: PRT
<213> ORGANISM: Homo sapiens

<400> SEQUENCE: 4

Val Pro Arg Asp Leu Glu Val Val Ala Ala Thr Pro Thr Ser Leu Leu
1               5                   10                  15

Ile Ser Trp Asp Ala Pro Ala Val Thr Val Arg Tyr Tyr Arg Ile Thr
            20                  25                  30

Tyr Gly Glu Thr Gly Gly Asn Ser Pro Val Gln Glu Phe Thr Val Pro
        35                  40                  45

Gly Ser Lys Ser Thr Ala Thr Ile Ser Gly Leu Lys Pro Gly Val Asp
    50                  55                  60

Tyr Thr Ile Thr Val Tyr Ala Val Thr Gly Arg Gly Asp Ser Pro Ala
65                  70                  75                  80

```
Ser Ser Lys Pro Ile Ser Ile Asn Tyr Arg Thr
                85                  90
```

<210> SEQ ID NO 5
<211> LENGTH: 90
<212> TYPE: PRT
<213> ORGANISM: Homo sapiens

<400> SEQUENCE: 5

```
Pro Arg Asp Leu Glu Val Val Ala Ala Thr Pro Thr Ser Leu Leu Ile
1               5                   10                  15

Ser Trp Asp Ala Pro Ala Val Thr Val Arg Tyr Tyr Arg Ile Thr Tyr
                20                  25                  30

Gly Glu Thr Gly Gly Asn Ser Pro Val Gln Glu Phe Thr Val Pro Gly
            35                  40                  45

Ser Lys Ser Thr Ala Thr Ile Ser Gly Leu Lys Pro Gly Val Asp Tyr
        50                  55                  60

Thr Ile Thr Val Tyr Ala Val Thr Gly Arg Gly Asp Ser Pro Ala Ser
65                  70                  75                  80

Ser Lys Pro Ile Ser Ile Asn Tyr Arg Thr
                85                  90
```

<210> SEQ ID NO 6
<211> LENGTH: 89
<212> TYPE: PRT
<213> ORGANISM: Homo sapiens

<400> SEQUENCE: 6

```
Arg Asp Leu Glu Val Val Ala Ala Thr Pro Thr Ser Leu Leu Ile Ser
1               5                   10                  15

Trp Asp Ala Pro Ala Val Thr Val Arg Tyr Tyr Arg Ile Thr Tyr Gly
                20                  25                  30

Glu Thr Gly Gly Asn Ser Pro Val Gln Glu Phe Thr Val Pro Gly Ser
            35                  40                  45

Lys Ser Thr Ala Thr Ile Ser Gly Leu Lys Pro Gly Val Asp Tyr Thr
        50                  55                  60

Ile Thr Val Tyr Ala Val Thr Gly Arg Gly Asp Ser Pro Ala Ser Ser
65                  70                  75                  80

Lys Pro Ile Ser Ile Asn Tyr Arg Thr
                85
```

<210> SEQ ID NO 7
<211> LENGTH: 88
<212> TYPE: PRT
<213> ORGANISM: Homo sapiens

<400> SEQUENCE: 7

```
Asp Leu Glu Val Val Ala Ala Thr Pro Thr Ser Leu Leu Ile Ser Trp
1               5                   10                  15

Asp Ala Pro Ala Val Thr Val Arg Tyr Tyr Arg Ile Thr Tyr Gly Glu
                20                  25                  30

Thr Gly Gly Asn Ser Pro Val Gln Glu Phe Thr Val Pro Gly Ser Lys
            35                  40                  45

Ser Thr Ala Thr Ile Ser Gly Leu Lys Pro Gly Val Asp Tyr Thr Ile
        50                  55                  60

Thr Val Tyr Ala Val Thr Gly Arg Gly Asp Ser Pro Ala Ser Ser Lys
65                  70                  75                  80

Pro Ile Ser Ile Asn Tyr Arg Thr
```

<210> SEQ ID NO 8
<211> LENGTH: 87
<212> TYPE: PRT
<213> ORGANISM: Homo sapiens

<400> SEQUENCE: 8

Leu Glu Val Val Ala Ala Thr Pro Thr Ser Leu Leu Ile Ser Trp Asp
1               5                   10                  15

Ala Pro Ala Val Thr Val Arg Tyr Tyr Arg Ile Thr Tyr Gly Glu Thr
            20                  25                  30

Gly Gly Asn Ser Pro Val Gln Glu Phe Thr Val Pro Gly Ser Lys Ser
        35                  40                  45

Thr Ala Thr Ile Ser Gly Leu Lys Pro Gly Val Asp Tyr Thr Ile Thr
    50                  55                  60

Val Tyr Ala Val Thr Gly Arg Gly Asp Ser Pro Ala Ser Ser Lys Pro
65                  70                  75                  80

Ile Ser Ile Asn Tyr Arg Thr
                85

<210> SEQ ID NO 9
<211> LENGTH: 166
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (14)..(33)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (39)..(58)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (64)..(83)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (87)..(106)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (113)..(132)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (140)..(159)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent

<400> SEQUENCE: 9

```
Val Ser Asp Val Pro Arg Asp Leu Glu Val Val Ala Ala Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Leu Leu Ile Ser Trp Xaa Xaa Xaa Xaa Xaa Xaa Xaa Xaa Xaa Xaa
            35                  40                  45

Xaa Xaa Xaa Xaa Xaa Xaa Xaa Xaa Xaa Tyr Arg Ile Thr Tyr Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Phe Thr Val Xaa Xaa Xaa Xaa Xaa Xaa Xaa Xaa Xaa Xaa
                85                  90                  95

Xaa Xaa Xaa Xaa Xaa Xaa Xaa Xaa Xaa Ala Thr Ile Ser Gly Leu
        100                 105                 110

Xaa Xaa Xaa Xaa Xaa Xaa Xaa Xaa Xaa Xaa Xaa Xaa Xaa Xaa Xaa Xaa
            115                 120                 125

Xaa Xaa Xaa Xaa Tyr Thr Ile Thr Val Tyr Ala Xaa Xaa Xaa Xaa
    130                 135                 140

Xaa Xaa Xaa Xaa Xaa Xaa Xaa Xaa Xaa Xaa Xaa Xaa Xaa Xaa Xaa Ile
145                 150                 155                 160

Ser Ile Asn Tyr Arg Thr
                165

<210> SEQ ID NO 10
<211> LENGTH: 165
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (13)..(32)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (38)..(57)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (63)..(82)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (86)..(105)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (112)..(131)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (139)..(158)
```

-continued

```
<223> OTHER INFORMATION: Any amino acid and this region may encompass
     2-20, 2-15, 2-10, 2-8, 5-20, 5-15, 5-10, 5-8, 6-20, 6-15, 6-10,
     6-8, 2-7, 5-7, or 6-7 residues, wherein some positions may be
     absent

<400> SEQUENCE: 10

Ser Asp Val Pro Arg Asp Leu Glu Val Val Ala Ala Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Leu Leu Ile Ser Trp Xaa Xaa Xaa Xaa Xaa Xaa Xaa Xaa Xaa Xaa Xaa
            35                  40                  45

Xaa Xaa Xaa Xaa Xaa Xaa Xaa Xaa Tyr Arg Ile Thr Tyr Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Phe Thr Val Xaa Xaa Xaa Xaa Xaa Xaa Xaa Xaa Xaa Xaa
            85                  90                  95

Xaa Xaa Xaa Xaa Xaa Xaa Xaa Xaa Ala Thr Ile Ser Gly Leu Xaa
        100                 105                 110

Xaa Xaa Xaa Xaa Xaa Xaa Xaa Xaa Xaa Xaa Xaa Xaa Xaa Xaa Xaa Xaa
            115                 120                 125

Xaa Xaa Xaa Tyr Thr Ile Thr Val Tyr Ala Xaa Xaa Xaa Xaa Xaa
130                 135                 140

Xaa Xaa Xaa Xaa Xaa Xaa Xaa Xaa Xaa Xaa Xaa Xaa Xaa Xaa Ile Ser
145                 150                 155                 160

Ile Asn Tyr Arg Thr
                165

<210> SEQ ID NO 11
<211> LENGTH: 164
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (12)..(31)
<223> OTHER INFORMATION: Any amino acid and this region may encompass
     2-20, 2-15, 2-10, 2-8, 5-20, 5-15, 5-10, 5-8, 6-20, 6-15, 6-10,
     6-8, 2-7, 5-7, or 6-7 residues, wherein some positions may be
     absent
<220> FEATURE:
<221> NAME/KEY: MOD_RES
<222> LOCATION: (37)..(56)
<223> OTHER INFORMATION: Any amino acid and this region may encompass
     2-20, 2-15, 2-10, 2-8, 5-20, 5-15, 5-10, 5-8, 6-20, 6-15, 6-10,
     6-8, 2-7, 5-7, or 6-7 residues, wherein some positions may be
     absent
<220> FEATURE:
<221> NAME/KEY: MOD_RES
<222> LOCATION: (62)..(81)
<223> OTHER INFORMATION: Any amino acid and this region may encompass
     2-20, 2-15, 2-10, 2-8, 5-20, 5-15, 5-10, 5-8, 6-20, 6-15, 6-10,
     6-8, 2-7, 5-7, or 6-7 residues, wherein some positions may be
     absent
<220> FEATURE:
<221> NAME/KEY: MOD_RES
<222> LOCATION: (85)..(104)
<223> OTHER INFORMATION: Any amino acid and this region may encompass
     2-20, 2-15, 2-10, 2-8, 5-20, 5-15, 5-10, 5-8, 6-20, 6-15, 6-10,
     6-8, 2-7, 5-7, or 6-7 residues, wherein some positions may be
     absent
<220> FEATURE:
<221> NAME/KEY: MOD_RES
<222> LOCATION: (111)..(130)
<223> OTHER INFORMATION: Any amino acid and this region may encompass
```

-continued 2-20, 2-15, 2-10, 2-8, 5-20, 5-15, 5-10, 5-8, 6-20, 6-15, 6-10, 6-8, 2-7, 5-7, or 6-7 residues, wherein some positions may be absent
<220> FEATURE:
<221> NAME/KEY: MOD_RES
<222> LOCATION: (138)..(157)
<223> OTHER INFORMATION: Any amino acid and this region may encompass
    2-20, 2-15, 2-10, 2-8, 5-20, 5-15, 5-10, 5-8, 6-20, 6-15, 6-10,
    6-8, 2-7, 5-7, or 6-7 residues, wherein some positions may be
    absent

<400> SEQUENCE: 11

Asp Val Pro Arg Asp Leu Glu Val Val Ala Ala Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Leu
            20                  25                  30

Leu Ile Ser Trp Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Tyr Arg Ile Thr Tyr Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Phe Thr Val Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Ala Thr Ile Ser Gly Leu Xaa Xaa
            100                 105                 110

Xaa Xaa Xaa Xaa Xaa Xaa Xaa Xaa Xaa Xaa Xaa Xaa Xaa Xaa Xaa Xaa
        115                 120                 125

Xaa Xaa Tyr Thr Ile Thr Val Tyr Ala Xaa Xaa Xaa Xaa Xaa Xaa Xaa
    130                 135                 140

Xaa Xaa Xaa Xaa Xaa Xaa Xaa Xaa Xaa Xaa Xaa Xaa Xaa Ile Ser Ile
145                 150                 155                 160

Asn Tyr Arg Thr

<210> SEQ ID NO 12
<211> LENGTH: 163
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (11)..(30)
<223> OTHER INFORMATION: Any amino acid and this region may encompass
    2-20, 2-15, 2-10, 2-8, 5-20, 5-15, 5-10, 5-8, 6-20, 6-15, 6-10,
    6-8, 2-7, 5-7, or 6-7 residues, wherein some positions may be
    absent
<220> FEATURE:
<221> NAME/KEY: MOD_RES
<222> LOCATION: (36)..(55)
<223> OTHER INFORMATION: Any amino acid and this region may encompass
    2-20, 2-15, 2-10, 2-8, 5-20, 5-15, 5-10, 5-8, 6-20, 6-15, 6-10,
    6-8, 2-7, 5-7, or 6-7 residues, wherein some positions may be
    absent
<220> FEATURE:
<221> NAME/KEY: MOD_RES
<222> LOCATION: (61)..(80)
<223> OTHER INFORMATION: Any amino acid and this region may encompass
    2-20, 2-15, 2-10, 2-8, 5-20, 5-15, 5-10, 5-8, 6-20, 6-15, 6-10,
    6-8, 2-7, 5-7, or 6-7 residues, wherein some positions may be
    absent
<220> FEATURE:
<221> NAME/KEY: MOD_RES
<222> LOCATION: (84)..(103)
<223> OTHER INFORMATION: Any amino acid and this region may encompass
    2-20, 2-15, 2-10, 2-8, 5-20, 5-15, 5-10, 5-8, 6-20, 6-15, 6-10,
    6-8, 2-7, 5-7, or 6-7 residues, wherein some positions may be

```
                absent
<220> FEATURE:
<221> NAME/KEY: MOD_RES
<222> LOCATION: (110)..(129)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (137)..(156)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent

<400> SEQUENCE: 12

Val Pro Arg Asp Leu Glu Val Val Ala Ala Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Leu Leu
            20                  25                  30

Ile Ser Trp Xaa Xaa Xaa Xaa Xaa Xaa Xaa Xaa Xaa Xaa Xaa Xaa Xaa
            35                  40                  45

Xaa Xaa Xaa Xaa Xaa Xaa Xaa Tyr Arg Ile Thr Tyr Xaa Xaa Xaa Xaa
50                  55                  60

Xaa Xaa Xaa Xaa Xaa Xaa Xaa Xaa Xaa Xaa Xaa Xaa Xaa Xaa Xaa Xaa
65                  70                  75                  80

Phe Thr Val Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Ala Thr Ile Ser Gly Leu Xaa Xaa Xaa
            100                 105                 110

Xaa Xaa Xaa Xaa Xaa Xaa Xaa Xaa Xaa Xaa Xaa Xaa Xaa Xaa Xaa Xaa
            115                 120                 125

Xaa Tyr Thr Ile Thr Val Tyr Ala Xaa Xaa Xaa Xaa Xaa Xaa Xaa Xaa
130                 135                 140

Xaa Xaa Xaa Xaa Xaa Xaa Xaa Xaa Xaa Xaa Xaa Ile Ser Ile Asn
145                 150                 155                 160

Tyr Arg Thr

<210> SEQ ID NO 13
<211> LENGTH: 162
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (10)..(29)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (35)..(54)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (60)..(79)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
```

<221> NAME/KEY: MOD_RES
<222> LOCATION: (83)..(102)
<223> OTHER INFORMATION: Any amino acid and this region may encompass
     2-20, 2-15, 2-10, 2-8, 5-20, 5-15, 5-10, 5-8, 6-20, 6-15, 6-10,
     6-8, 2-7, 5-7, or 6-7 residues, wherein some positions may be
     absent
<220> FEATURE:
<221> NAME/KEY: MOD_RES
<222> LOCATION: (109)..(128)
<223> OTHER INFORMATION: Any amino acid and this region may encompass
     2-20, 2-15, 2-10, 2-8, 5-20, 5-15, 5-10, 5-8, 6-20, 6-15, 6-10,
     6-8, 2-7, 5-7, or 6-7 residues, wherein some positions may be
     absent
<220> FEATURE:
<221> NAME/KEY: MOD_RES
<222> LOCATION: (136)..(155)
<223> OTHER INFORMATION: Any amino acid and this region may encompass
     2-20, 2-15, 2-10, 2-8, 5-20, 5-15, 5-10, 5-8, 6-20, 6-15, 6-10,
     6-8, 2-7, 5-7, or 6-7 residues, wherein some positions may be
     absent

<400> SEQUENCE: 13

Pro Arg Asp Leu Glu Val Val Ala Ala Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Leu Leu Ile
            20                  25                  30

Ser Trp Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Tyr Arg Ile Thr Tyr Xaa Xaa Xaa Xaa Xaa
50                  55                  60

Xaa Xaa Xaa Xaa Xaa Xaa Xaa Xaa Xaa Xaa Xaa Xaa Xaa Xaa Xaa Phe
65                  70                  75                  80

Thr Val Xaa Xaa Xaa Xaa Xaa Xaa Xaa Xaa Xaa Xaa Xaa Xaa Xaa Xaa
            85                  90                  95

Xaa Xaa Xaa Xaa Xaa Xaa Ala Thr Ile Ser Gly Leu Xaa Xaa Xaa Xaa
                100                 105                 110

Xaa Xaa Xaa Xaa Xaa Xaa Xaa Xaa Xaa Xaa Xaa Xaa Xaa Xaa Xaa Xaa
            115                 120                 125

Tyr Thr Ile Thr Val Tyr Ala Xaa Xaa Xaa Xaa Xaa Xaa Xaa Xaa Xaa
    130                 135                 140

Xaa Xaa Xaa Xaa Xaa Xaa Xaa Xaa Xaa Xaa Xaa Ile Ser Ile Asn Tyr
145                 150                 155                 160

Arg Thr

<210> SEQ ID NO 14
<211> LENGTH: 161
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (9)..(28)
<223> OTHER INFORMATION: Any amino acid and this region may encompass
     2-20, 2-15, 2-10, 2-8, 5-20, 5-15, 5-10, 5-8, 6-20, 6-15, 6-10,
     6-8, 2-7, 5-7, or 6-7 residues, wherein some positions may be
     absent
<220> FEATURE:
<221> NAME/KEY: MOD_RES
<222> LOCATION: (34)..(53)
<223> OTHER INFORMATION: Any amino acid and this region may encompass
     2-20, 2-15, 2-10, 2-8, 5-20, 5-15, 5-10, 5-8, 6-20, 6-15, 6-10,
     6-8, 2-7, 5-7, or 6-7 residues, wherein some positions may be
     absent
<220> FEATURE:
<221> NAME/KEY: MOD_RES
<222> LOCATION: (59)..(78)

<223> OTHER INFORMATION: Any amino acid and this region may encompass
     2-20, 2-15, 2-10, 2-8, 5-20, 5-15, 5-10, 5-8, 6-20, 6-15, 6-10,
     6-8, 2-7, 5-7, or 6-7 residues, wherein some positions may be
     absent
<220> FEATURE:
<221> NAME/KEY: MOD_RES
<222> LOCATION: (82)..(101)
<223> OTHER INFORMATION: Any amino acid and this region may encompass
     2-20, 2-15, 2-10, 2-8, 5-20, 5-15, 5-10, 5-8, 6-20, 6-15, 6-10,
     6-8, 2-7, 5-7, or 6-7 residues, wherein some positions may be
     absent
<220> FEATURE:
<221> NAME/KEY: MOD_RES
<222> LOCATION: (108)..(127)
<223> OTHER INFORMATION: Any amino acid and this region may encompass
     2-20, 2-15, 2-10, 2-8, 5-20, 5-15, 5-10, 5-8, 6-20, 6-15, 6-10,
     6-8, 2-7, 5-7, or 6-7 residues, wherein some positions may be
     absent
<220> FEATURE:
<221> NAME/KEY: MOD_RES
<222> LOCATION: (135)..(154)
<223> OTHER INFORMATION: Any amino acid and this region may encompass
     2-20, 2-15, 2-10, 2-8, 5-20, 5-15, 5-10, 5-8, 6-20, 6-15, 6-10,
     6-8, 2-7, 5-7, or 6-7 residues, wherein some positions may be
     absent

<400> SEQUENCE: 14

Arg Asp Leu Glu Val Val Ala Ala Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Leu Leu Ile Ser
            20                  25                  30

Trp Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Tyr Arg Ile Thr Tyr Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Phe Thr
65                  70                  75                  80

Val Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Ala Thr Ile Ser Gly Leu Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa Tyr
        115                 120                 125

Thr Ile Thr Val Tyr Ala Xaa Xaa Xaa Xaa Xaa Xaa Xaa Xaa Xaa Xaa
130                 135                 140

Xaa Xaa Xaa Xaa Xaa Xaa Xaa Xaa Xaa Xaa Ile Ser Ile Asn Tyr Arg
145                 150                 155                 160

Thr

<210> SEQ ID NO 15
<211> LENGTH: 160
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (8)..(27)
<223> OTHER INFORMATION: Any amino acid and this region may encompass
     2-20, 2-15, 2-10, 2-8, 5-20, 5-15, 5-10, 5-8, 6-20, 6-15, 6-10,
     6-8, 2-7, 5-7, or 6-7 residues, wherein some positions may be
     absent
<220> FEATURE:
<221> NAME/KEY: MOD_RES
<222> LOCATION: (33)..(52)
<223> OTHER INFORMATION: Any amino acid and this region may encompass
     2-20, 2-15, 2-10, 2-8, 5-20, 5-15, 5-10, 5-8, 6-20, 6-15, 6-10, -continued 6-8, 2-7, 5-7, or 6-7 residues, wherein some positions may be
absent
<220> FEATURE:
<221> NAME/KEY: MOD_RES
<222> LOCATION: (58)..(77)
<223> OTHER INFORMATION: Any amino acid and this region may encompass
2-20, 2-15, 2-10, 2-8, 5-20, 5-15, 5-10, 5-8, 6-20, 6-15, 6-10,
6-8, 2-7, 5-7, or 6-7 residues, wherein some positions may be
absent
<220> FEATURE:
<221> NAME/KEY: MOD_RES
<222> LOCATION: (81)..(100)
<223> OTHER INFORMATION: Any amino acid and this region may encompass
2-20, 2-15, 2-10, 2-8, 5-20, 5-15, 5-10, 5-8, 6-20, 6-15, 6-10,
6-8, 2-7, 5-7, or 6-7 residues, wherein some positions may be
absent
<220> FEATURE:
<221> NAME/KEY: MOD_RES
<222> LOCATION: (107)..(126)
<223> OTHER INFORMATION: Any amino acid and this region may encompass
2-20, 2-15, 2-10, 2-8, 5-20, 5-15, 5-10, 5-8, 6-20, 6-15, 6-10,
6-8, 2-7, 5-7, or 6-7 residues, wherein some positions may be
absent
<220> FEATURE:
<221> NAME/KEY: MOD_RES
<222> LOCATION: (134)..(153)
<223> OTHER INFORMATION: Any amino acid and this region may encompass
2-20, 2-15, 2-10, 2-8, 5-20, 5-15, 5-10, 5-8, 6-20, 6-15, 6-10,
6-8, 2-7, 5-7, or 6-7 residues, wherein some positions may be
absent

<400> SEQUENCE: 15

Asp Leu Glu Val Val Ala Ala Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Leu Leu Ile Ser Trp
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Tyr Arg Ile Thr Tyr Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Phe Thr Val
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Xaa Xaa Ala Thr Ile Ser Gly Leu Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Tyr Thr
        115                 120                 125

Ile Thr Val Tyr Ala Xaa Xaa Xaa Xaa Xaa Xaa Xaa Xaa Xaa Xaa Xaa
    130                 135                 140

Xaa Xaa Xaa Xaa Xaa Xaa Xaa Xaa Xaa Ile Ser Ile Asn Tyr Arg Thr
145                 150                 155                 160

<210> SEQ ID NO 16
<211> LENGTH: 159
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (7)..(26)
<223> OTHER INFORMATION: Any amino acid and this region may encompass
2-20, 2-15, 2-10, 2-8, 5-20, 5-15, 5-10, 5-8, 6-20, 6-15, 6-10,
6-8, 2-7, 5-7, or 6-7 residues, wherein some positions may be
absent
<220> FEATURE:
<221> NAME/KEY: MOD_RES

```
<222> LOCATION: (32)..(51)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (57)..(76)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (80)..(99)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (106)..(125)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (133)..(152)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent

<400> SEQUENCE: 16

Leu Glu Val Val Ala Ala Xaa Xaa Xaa Xaa Xaa Xaa Xaa Xaa Xaa
1               5                   10                  15

Xaa Xaa Xaa Xaa Xaa Xaa Xaa Xaa Xaa Xaa Leu Leu Ile Ser Trp Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Tyr Arg Ile Thr Tyr Xaa Xaa Xaa Xaa Xaa Xaa Xaa
    50                  55                  60

Xaa Xaa Xaa Xaa Xaa Xaa Xaa Xaa Xaa Xaa Xaa Phe Thr Val Xaa
65                  70                  75                  80

Xaa Xaa Xaa Xaa Xaa Xaa Xaa Xaa Xaa Xaa Xaa Xaa Xaa Xaa Xaa
                85                  90                  95

Xaa Xaa Xaa Ala Thr Ile Ser Gly Leu Xaa Xaa Xaa Xaa Xaa Xaa
            100                 105                 110

Xaa Xaa Xaa Xaa Xaa Xaa Xaa Xaa Xaa Xaa Xaa Xaa Tyr Thr Ile
        115                 120                 125

Thr Val Tyr Ala Xaa Xaa Xaa Xaa Xaa Xaa Xaa Xaa Xaa Xaa Xaa
    130                 135                 140

Xaa Xaa Xaa Xaa Xaa Xaa Xaa Xaa Ile Ser Ile Asn Tyr Arg Thr
145                 150                 155

<210> SEQ ID NO 17
<211> LENGTH: 87
<212> TYPE: PRT
<213> ORGANISM: Homo sapiens

<400> SEQUENCE: 17

Leu Glu Val Val Ala Ala Thr Pro Thr Ser Leu Leu Ile Ser Trp Asp
1               5                   10                  15

Ala Pro Ala Val Thr Val Arg Tyr Tyr Arg Ile Thr Tyr Gly Glu Thr
            20                  25                  30
```

Gly Gly Asn Ser Pro Val Gln Glu Phe Thr Val Pro Gly Ser Lys Ser
             35                  40                  45

Thr Ala Thr Ile Ser Gly Leu Lys Pro Gly Val Asp Tyr Thr Ile Thr
         50                  55                  60

Val Tyr Ala Val Thr Gly Arg Gly Asp Ser Pro Ala Ser Ser Lys Pro
 65                  70                  75                  80

Ile Ser Ile Asn Tyr Arg Thr
                 85

<210> SEQ ID NO 18
<211> LENGTH: 159
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (7)..(26)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (32)..(51)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (57)..(76)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (80)..(99)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (106)..(125)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent
<220> FEATURE:
<221> NAME/KEY: MOD_RES
<222> LOCATION: (133)..(152)
<223> OTHER INFORMATION: Any amino acid and this region may encompass
      2-20, 2-15, 2-10, 2-8, 5-20, 5-15, 5-10, 5-8, 6-20, 6-15, 6-10,
      6-8, 2-7, 5-7, or 6-7 residues, wherein some positions may be
      absent

<400> SEQUENCE: 18

Leu Glu Val Val Ala Ala Xaa Xaa Xaa Xaa Xaa Xaa Xaa Xaa Xaa
 1               5                  10                  15

Xaa Xaa Xaa Xaa Xaa Xaa Xaa Xaa Xaa Xaa Leu Leu Ile Ser Trp Xaa
             20                  25                  30

Xaa Xaa Xaa Xaa Xaa Xaa Xaa Xaa Xaa Xaa Xaa Xaa Xaa Xaa Xaa Xaa
         35                  40                  45

Xaa Xaa Xaa Tyr Arg Ile Thr Tyr Xaa Xaa Xaa Xaa Xaa Xaa Xaa Xaa
 50                  55                  60

Xaa Xaa Xaa Xaa Xaa Xaa Xaa Xaa Xaa Xaa Xaa Phe Thr Val Xaa
 65                  70                  75                  80

```
Xaa Xaa Xaa Xaa Xaa Xaa Xaa Xaa Xaa Xaa Xaa Xaa Xaa Xaa
                85                  90                  95

Xaa Xaa Xaa Ala Thr Ile Ser Gly Leu Xaa Xaa Xaa Xaa Xaa
            100                 105                 110

Xaa Xaa Xaa Xaa Xaa Xaa Xaa Xaa Xaa Xaa Xaa Tyr Thr Ile
        115                 120                 125

Thr Val Tyr Ala Xaa Xaa Xaa Xaa Xaa Xaa Xaa Xaa Xaa Xaa
    130                 135                 140

Xaa Xaa Xaa Xaa Xaa Xaa Xaa Xaa Ile Ser Ile Asn Tyr Arg Thr
145                 150                 155

<210> SEQ ID NO 19
<211> LENGTH: 7
<212> TYPE: PRT
<213> ORGANISM: Homo sapiens

<400> SEQUENCE: 19

Val Ser Asp Val Pro Arg Asp
1               5

<210> SEQ ID NO 20
<211> LENGTH: 6
<212> TYPE: PRT
<213> ORGANISM: Homo sapiens

<400> SEQUENCE: 20

Ser Asp Val Pro Arg Asp
1               5

<210> SEQ ID NO 21
<211> LENGTH: 5
<212> TYPE: PRT
<213> ORGANISM: Homo sapiens

<400> SEQUENCE: 21

Asp Val Pro Arg Asp
1               5

<210> SEQ ID NO 22
<211> LENGTH: 4
<212> TYPE: PRT
<213> ORGANISM: Homo sapiens

<400> SEQUENCE: 22

Val Pro Arg Asp
1

<210> SEQ ID NO 23
<211> LENGTH: 101
<212> TYPE: PRT
<213> ORGANISM: Artificial Sequence
<220> FEATURE:
<223> OTHER INFORMATION: Synthetic polypeptide

<400> SEQUENCE: 23

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Glu Thr Gly Gly Asn Ser Pro Val Gln Glu Phe
        35                  40                  45
```

```
Thr Val Pro Gly Ser Lys Ser Thr Ala Thr Ile Ser Gly Leu Lys Pro
    50                  55                  60

Gly Val Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Arg Thr Glu Ile
                85                  90                  95

Asp Lys Pro Ser Gln
            100

<210> SEQ ID NO 24
<211> LENGTH: 10
<212> TYPE: PRT
<213> ORGANISM: Artificial Sequence
<220> FEATURE:
<223> OTHER INFORMATION: Synthetic peptide

<400> SEQUENCE: 24

Met Gly Val Ser Asp Val Pro Arg Asp Leu
1               5                   10

<210> SEQ ID NO 25
<211> LENGTH: 9
<212> TYPE: PRT
<213> ORGANISM: Artificial Sequence
<220> FEATURE:
<223> OTHER INFORMATION: Synthetic peptide

<400> SEQUENCE: 25

Gly Val Ser Asp Val Pro Arg Asp Leu
1               5

<210> SEQ ID NO 26
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: /replace="Gly" or " "
<220> FEATURE:
<221> NAME/KEY: MISC_FEATURE
<222> LOCATION: (1)..(2)
<223> OTHER INFORMATION: /note="When only 1 position is present, the
      position may be Met or Gly.  When two positions are present, the
      positions are Met-Gly. See specification for further explanation."
<220> FEATURE:
<221> NAME/KEY: MISC_FEATURE
<222> LOCATION: (1)..(9)
<223> OTHER INFORMATION: /note="Variant residues given in the sequence
      have no preference with respect to those in the annotations for
      variant positions"
<220> FEATURE:
<221> NAME/KEY: VARIANT
<222> LOCATION: (2)..(2)
<223> OTHER INFORMATION: /replace="Met" or " "

<400> SEQUENCE: 26

Met Gly Ser Asp Val Pro Arg Asp Leu
1               5

<210> SEQ ID NO 27
<211> LENGTH: 8
<212> TYPE: PRT
<213> ORGANISM: Artificial Sequence
<220> FEATURE:
<223> OTHER INFORMATION: Synthetic peptide
<220> FEATURE:
```

<221> NAME/KEY: VARIANT
<222> LOCATION: (1)..(1)
<223> OTHER INFORMATION: /replace="Gly" or " "
<220> FEATURE:
<221> NAME/KEY: MISC_FEATURE
<222> LOCATION: (1)..(2)
<223> OTHER INFORMATION: /note="When only 1 position is present, the
      position may be Met or Gly.  When two positions are present, the
      positions are Met-Gly. See specification for further explanation."
<220> FEATURE:
<221> NAME/KEY: MISC_FEATURE
<222> LOCATION: (1)..(8)
<223> OTHER INFORMATION: /note="Variant residues given in the sequence
      have no preference with respect to those in the annotations for
      variant positions"
<220> FEATURE:
<221> NAME/KEY: VARIANT
<222> LOCATION: (2)..(2)
<223> OTHER INFORMATION: /replace="Met" or " "

<400> SEQUENCE: 27

Met Gly Asp Val Pro Arg Asp Leu
1               5

<210> SEQ ID NO 28
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: /replace="Gly" or " "
<220> FEATURE:
<221> NAME/KEY: MISC_FEATURE
<222> LOCATION: (1)..(2)
<223> OTHER INFORMATION: /note="When only 1 position is present, the
      position may be Met or Gly.  When two positions are present, the
      positions are Met-Gly. See specification for further explanation."
<220> FEATURE:
<221> NAME/KEY: MISC_FEATURE
<222> LOCATION: (1)..(7)
<223> OTHER INFORMATION: /note="Variant residues given in the sequence
      have no preference with respect to those in the annotations for
      variant positions"
<220> FEATURE:
<221> NAME/KEY: VARIANT
<222> LOCATION: (2)..(2)
<223> OTHER INFORMATION: /replace="Met" or " "

<400> SEQUENCE: 28

Met Gly Val Pro Arg Asp Leu
1               5

<210> SEQ ID NO 29
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: /replace="Gly" or " "
<220> FEATURE:
<221> NAME/KEY: MISC_FEATURE
<222> LOCATION: (1)..(2)
<223> OTHER INFORMATION: /note="When only 1 position is present, the
      position may be Met or Gly.  When two positions are present, the
      positions are Met-Gly. See specification for further explanation."
<220> FEATURE:
<221> NAME/KEY: MISC_FEATURE
<222> LOCATION: (1)..(6)
<223> OTHER INFORMATION: /note="Variant residues given in the sequence

```
      have no preference with respect to those in the annotations for
      variant positions"
<220> FEATURE:
<221> NAME/KEY: VARIANT
<222> LOCATION: (2)..(2)
<223> OTHER INFORMATION: /replace="Met" or " "

<400> SEQUENCE: 29

Met Gly Pro Arg Asp Leu
1               5

<210> SEQ ID NO 30
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: /replace="Gly" or " "
<220> FEATURE:
<221> NAME/KEY: MISC_FEATURE
<222> LOCATION: (1)..(2)
<223> OTHER INFORMATION: /note="When only 1 position is present, the
      position may be Met or Gly.  When two positions are present, the
      positions are Met-Gly. See specification for further explanation."
<220> FEATURE:
<221> NAME/KEY: MISC_FEATURE
<222> LOCATION: (1)..(5)
<223> OTHER INFORMATION: /note="Variant residues given in the sequence
      have no preference with respect to those in the annotations for
      variant positions"
<220> FEATURE:
<221> NAME/KEY: VARIANT
<222> LOCATION: (2)..(2)
<223> OTHER INFORMATION: /replace="Met" or " "

<400> SEQUENCE: 30

Met Gly Arg Asp Leu
1               5

<210> SEQ ID NO 31
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: /replace="Gly" or " "
<220> FEATURE:
<221> NAME/KEY: MISC_FEATURE
<222> LOCATION: (1)..(2)
<223> OTHER INFORMATION: /note="When only 1 position is present, the
      position may be Met or Gly.  When two positions are present, the
      positions are Met-Gly. See specification for further explanation."
<220> FEATURE:
<221> NAME/KEY: MISC_FEATURE
<222> LOCATION: (1)..(4)
<223> OTHER INFORMATION: /note="Variant residues given in the sequence
      have no preference with respect to those in the annotations for
      variant positions"
<220> FEATURE:
<221> NAME/KEY: VARIANT
<222> LOCATION: (2)..(2)
<223> OTHER INFORMATION: /replace="Met" or " "

<400> SEQUENCE: 31

Met Gly Asp Leu
1
```

```
<210> SEQ ID NO 32
<211> LENGTH: 6
<212> TYPE: PRT
<213> ORGANISM: Artificial Sequence
<220> FEATURE:
<223> OTHER INFORMATION: Synthetic peptide

<400> SEQUENCE: 32

Met Ala Ser Thr Ser Gly
1               5

<210> SEQ ID NO 33
<211> LENGTH: 91
<212> TYPE: PRT
<213> ORGANISM: Artificial Sequence
<220> FEATURE:
<223> OTHER INFORMATION: Synthetic polypeptide

<400> SEQUENCE: 33

Met Pro Ala Pro Thr Asp Leu Arg Phe Thr Asn Glu Thr Pro Ser Ser
1               5                   10                  15

Leu Leu Ile Ser Trp Thr Pro Pro Arg Val Gln Ile Thr Gly Tyr Ile
            20                  25                  30

Ile Arg Tyr Gly Pro Val Gly Ser Asp Gly Arg Val Lys Glu Phe Thr
            35                  40                  45

Val Pro Pro Ser Val Ser Ser Ala Thr Ile Thr Gly Leu Lys Pro Gly
        50                  55                  60

Thr Glu Tyr Thr Ile Ser Val Ile Ala Leu Lys Asp Asn Gln Glu Ser
65                  70                  75                  80

Glu Pro Leu Arg Gly Arg Val Thr Thr Gly Gly
                85                  90

<210> SEQ ID NO 34
<211> LENGTH: 4
<212> TYPE: PRT
<213> ORGANISM: Artificial Sequence
<220> FEATURE:
<223> OTHER INFORMATION: Synthetic peptide

<400> SEQUENCE: 34

Thr Pro Ser Ser
1

<210> SEQ ID NO 35
<211> LENGTH: 7
<212> TYPE: PRT
<213> ORGANISM: Artificial Sequence
<220> FEATURE:
<223> OTHER INFORMATION: Synthetic peptide

<400> SEQUENCE: 35

Thr Pro Pro Arg Val Gln Ile
1               5

<210> SEQ ID NO 36
<211> LENGTH: 6
<212> TYPE: PRT
<213> ORGANISM: Artificial Sequence
<220> FEATURE:
<223> OTHER INFORMATION: Synthetic peptide

<400> SEQUENCE: 36

Val Gly Ser Asp Gly Arg
1               5
```

<210> SEQ ID NO 37
<211> LENGTH: 4
<212> TYPE: PRT
<213> ORGANISM: Artificial Sequence
<220> FEATURE:
<223> OTHER INFORMATION: Synthetic peptide

<400> SEQUENCE: 37

Pro Ser Val Ser
1

<210> SEQ ID NO 38
<211> LENGTH: 5
<212> TYPE: PRT
<213> ORGANISM: Artificial Sequence
<220> FEATURE:
<223> OTHER INFORMATION: Synthetic peptide

<400> SEQUENCE: 38

Gly Leu Lys Pro Gly
1               5

<210> SEQ ID NO 39
<211> LENGTH: 8
<212> TYPE: PRT
<213> ORGANISM: Artificial Sequence
<220> FEATURE:
<223> OTHER INFORMATION: Synthetic peptide

<400> SEQUENCE: 39

Lys Asp Asn Gln Glu Ser Glu Pro
1               5

<210> SEQ ID NO 40
<211> LENGTH: 89
<212> TYPE: PRT
<213> ORGANISM: Artificial Sequence
<220> FEATURE:
<223> OTHER INFORMATION: Synthetic polypeptide

<400> SEQUENCE: 40

Leu Asp Ala Pro Thr Asp Leu Gln Val Thr Asn Val Thr Asp Thr Ser
1               5                   10                  15

Ile Thr Val Ser Trp Thr Pro Pro Ser Ala Thr Ile Thr Gly Tyr Arg
            20                  25                  30

Ile Thr Tyr Thr Pro Ser Asn Gly Pro Gly Glu Pro Lys Glu Leu Thr
        35                  40                  45

Val Pro Pro Ser Ser Thr Ser Val Thr Ile Thr Gly Ile Thr Pro Gly
    50                  55                  60

Val Glu Tyr Val Val Ser Val Tyr Ala Leu Lys Asp Asn Gln Glu Ser
65                  70                  75                  80

Pro Pro Leu Val Gly Thr Cys Thr Thr
                85

<210> SEQ ID NO 41
<211> LENGTH: 89
<212> TYPE: PRT
<213> ORGANISM: Artificial Sequence
<220> FEATURE:
<223> OTHER INFORMATION: Synthetic polypeptide

<400> SEQUENCE: 41

Leu Pro Ala Pro Lys Asn Leu Val Val Ser Glu Val Thr Glu Asp Ser
1               5                   10                  15

Leu Arg Leu Ser Trp Thr Ala Pro Asp Ala Ala Phe Asp Ser Phe Leu
            20                  25                  30

Ile Gln Tyr Gln Glu Ser Glu Lys Val Gly Glu Ala Ile Asn Leu Thr
        35                  40                  45

Val Pro Gly Ser Glu Arg Ser Tyr Asp Leu Thr Gly Leu Lys Pro Gly
 50                  55                  60

Thr Glu Tyr Thr Val Ser Ile Tyr Gly Val Lys Gly His Arg Ser
 65                  70                  75                  80

Asn Pro Leu Ser Ala Glu Phe Thr Thr
                85

<210> SEQ ID NO 42
<211> LENGTH: 4
<212> TYPE: PRT
<213> ORGANISM: Artificial Sequence
<220> FEATURE:
<223> OTHER INFORMATION: Synthetic peptide

<400> SEQUENCE: 42

Thr Glu Asp Ser
1

<210> SEQ ID NO 43
<211> LENGTH: 7
<212> TYPE: PRT
<213> ORGANISM: Artificial Sequence
<220> FEATURE:
<223> OTHER INFORMATION: Synthetic peptide

<400> SEQUENCE: 43

Thr Ala Pro Asp Ala Ala Phe
1               5

<210> SEQ ID NO 44
<211> LENGTH: 6
<212> TYPE: PRT
<213> ORGANISM: Artificial Sequence
<220> FEATURE:
<223> OTHER INFORMATION: Synthetic peptide

<400> SEQUENCE: 44

Ser Glu Lys Val Gly Glu
1               5

<210> SEQ ID NO 45
<211> LENGTH: 4
<212> TYPE: PRT
<213> ORGANISM: Artificial Sequence
<220> FEATURE:
<223> OTHER INFORMATION: Synthetic peptide

<400> SEQUENCE: 45

Gly Ser Glu Arg
1

<210> SEQ ID NO 46
<211> LENGTH: 5
<212> TYPE: PRT
<213> ORGANISM: Artificial Sequence
<220> FEATURE:
<223> OTHER INFORMATION: Synthetic peptide

<400> SEQUENCE: 46

Gly Leu Lys Pro Gly

```
1               5
```

<210> SEQ ID NO 47
<211> LENGTH: 7
<212> TYPE: PRT
<213> ORGANISM: Artificial Sequence
<220> FEATURE:
<223> OTHER INFORMATION: Synthetic peptide

<400> SEQUENCE: 47

```
Lys Gly Gly His Arg Ser Asn
1               5
```

<210> SEQ ID NO 48
<211> LENGTH: 7
<212> TYPE: PRT
<213> ORGANISM: Artificial Sequence
<220> FEATURE:
<223> OTHER INFORMATION: Synthetic peptide

<400> SEQUENCE: 48

```
Gly Pro Gly Pro Gly Pro Gly
1               5
```

<210> SEQ ID NO 49
<211> LENGTH: 11
<212> TYPE: PRT
<213> ORGANISM: Artificial Sequence
<220> FEATURE:
<223> OTHER INFORMATION: Synthetic peptide

<400> SEQUENCE: 49

```
Gly Pro Gly Pro Gly Pro Gly Pro Gly Pro Gly
1               5                   10
```

<210> SEQ ID NO 50
<211> LENGTH: 6
<212> TYPE: PRT
<213> ORGANISM: Artificial Sequence
<220> FEATURE:
<223> OTHER INFORMATION: Synthetic peptide

<400> SEQUENCE: 50

```
Pro Ala Pro Ala Pro Ala
1               5
```

<210> SEQ ID NO 51
<211> LENGTH: 12
<212> TYPE: PRT
<213> ORGANISM: Artificial Sequence
<220> FEATURE:
<223> OTHER INFORMATION: Synthetic peptide

<400> SEQUENCE: 51

```
Pro Ala Pro Ala Pro Ala Pro Ala Pro Ala Pro Ala
1               5                   10
```

<210> SEQ ID NO 52
<211> LENGTH: 18
<212> TYPE: PRT
<213> ORGANISM: Artificial Sequence
<220> FEATURE:
<223> OTHER INFORMATION: Synthetic peptide

<400> SEQUENCE: 52

```
Pro Ala Pro Ala Pro Ala Pro Ala Pro Ala Pro Ala Pro Ala Pro Ala
1               5                   10                  15
```

Pro Ala

<210> SEQ ID NO 53
<211> LENGTH: 10
<212> TYPE: PRT
<213> ORGANISM: Artificial Sequence
<220> FEATURE:
<223> OTHER INFORMATION: Synthetic peptide

<400> SEQUENCE: 53

Gly Ser Gly Ser Gly Ser Gly Ser Gly Ser
1               5                   10

<210> SEQ ID NO 54
<211> LENGTH: 12
<212> TYPE: PRT
<213> ORGANISM: Artificial Sequence
<220> FEATURE:
<223> OTHER INFORMATION: Synthetic peptide

<400> SEQUENCE: 54

Gly Ser Gly Ser Gly Ser Gly Ser Gly Ser Gly Ser
1               5                   10

<210> SEQ ID NO 55
<211> LENGTH: 20
<212> TYPE: PRT
<213> ORGANISM: Artificial Sequence
<220> FEATURE:
<223> OTHER INFORMATION: Synthetic peptide

<400> SEQUENCE: 55

Gly Ser Gly Ser Gly Ser Gly Ser Gly Ser Gly Ser Gly Ser Gly Ser
1               5                   10                  15

Gly Ser Gly Ser
            20

<210> SEQ ID NO 56
<211> LENGTH: 20
<212> TYPE: PRT
<213> ORGANISM: Artificial Sequence
<220> FEATURE:
<223> OTHER INFORMATION: Synthetic peptide

<400> SEQUENCE: 56

Gly Gly Gly Gly Ser Gly Gly Gly Ser Gly Gly Gly Gly Ser Gly
1               5                   10                  15

Gly Gly Gly Ser
            20

<210> SEQ ID NO 57
<211> LENGTH: 25
<212> TYPE: PRT
<213> ORGANISM: Artificial Sequence
<220> FEATURE:
<223> OTHER INFORMATION: Synthetic peptide

<400> SEQUENCE: 57

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 58

```
<211> LENGTH: 15
<212> TYPE: PRT
<213> ORGANISM: Artificial Sequence
<220> FEATURE:
<223> OTHER INFORMATION: Synthetic peptide

<400> SEQUENCE: 58

Gly Gly Gly Gly Ser Gly Gly Gly Gly Ser Gly Gly Gly Gly Ser Gly
1               5                   10                  15

<210> SEQ ID NO 59
<211> LENGTH: 93
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (88)..(90)
<223> OTHER INFORMATION: /note="This region may encompass 1-3 "Pro"
      residues"
<220> FEATURE:
<221> NAME/KEY: MISC_FEATURE
<222> LOCATION: (88)..(93)
<223> OTHER INFORMATION: /note="See specification as filed for detailed
      description of substitutions and preferred embodiments"
<220> FEATURE:
<221> NAME/KEY: MOD_RES
<222> LOCATION: (91)..(93)
<223> OTHER INFORMATION: Any amino acid
<220> FEATURE:
<221> NAME/KEY: MISC_FEATURE
<222> LOCATION: (91)..(93)
<223> OTHER INFORMATION: /note="This region may encompass 1-3 residues"

<400> SEQUENCE: 59

Leu Glu Val Val Ala Ala Thr Pro Thr Ser Leu Leu Ile Ser Trp Asp
1               5                   10                  15

Ala Pro Ala Val Thr Val Arg Tyr Tyr Arg Ile Thr Tyr Gly Glu Thr
                20                  25                  30

Gly Gly Asn Ser Pro Val Gln Glu Phe Thr Val Pro Gly Ser Lys Ser
            35                  40                  45

Thr Ala Thr Ile Ser Gly Leu Lys Pro Gly Val Asp Tyr Thr Ile Thr
    50                  55                  60

Val Tyr Ala Val Thr Gly Arg Gly Asp Ser Pro Ala Ser Ser Lys Pro
65                  70                  75                  80

Ile Ser Ile Asn Tyr Arg Thr Pro Pro Pro Xaa Xaa Xaa
                85                  90

<210> SEQ ID NO 60
<211> LENGTH: 100
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (95)..(97)
<223> OTHER INFORMATION: /note="This region may encompass 1-3 "Pro"
      residues"
<220> FEATURE:
<221> NAME/KEY: MISC_FEATURE
<222> LOCATION: (95)..(100)
<223> OTHER INFORMATION: /note="See specification as filed for detailed
      description of substitutions and preferred embodiments"
<220> FEATURE:
<221> NAME/KEY: MOD_RES
<222> LOCATION: (98)..(100)
<223> OTHER INFORMATION: Any amino acid
<220> FEATURE:
```

```
<221> NAME/KEY: MISC_FEATURE
<222> LOCATION: (98)..(100)
<223> OTHER INFORMATION: /note="This region may encompass 1-3 residues"

<400> SEQUENCE: 60
```

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Glu Thr Gly Gly Asn Ser Pro Val Gln Glu Phe
        35                  40                  45

Thr Val Pro Gly Ser Lys Ser Thr Ala Thr Ile Ser Gly Leu Lys Pro
50                  55                  60

Gly Val Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Arg Thr Pro Pro
                85                  90                  95

Pro Xaa Xaa Xaa
        100

```
<210> SEQ ID NO 61
<211> LENGTH: 4
<212> TYPE: PRT
<213> ORGANISM: Artificial Sequence
<220> FEATURE:
<223> OTHER INFORMATION: Synthetic peptide

<400> SEQUENCE: 61
```

Pro Ile Asp Lys
1

```
<210> SEQ ID NO 62
<211> LENGTH: 5
<212> TYPE: PRT
<213> ORGANISM: Artificial Sequence
<220> FEATURE:
<223> OTHER INFORMATION: Synthetic peptide

<400> SEQUENCE: 62
```

Pro Pro Ile Asp Lys
1               5

```
<210> SEQ ID NO 63
<211> LENGTH: 4
<212> TYPE: PRT
<213> ORGANISM: Artificial Sequence
<220> FEATURE:
<223> OTHER INFORMATION: Synthetic peptide

<400> SEQUENCE: 63
```

Pro Ile Glu Lys
1

```
<210> SEQ ID NO 64
<211> LENGTH: 5
<212> TYPE: PRT
<213> ORGANISM: Artificial Sequence
<220> FEATURE:
<223> OTHER INFORMATION: Synthetic peptide

<400> SEQUENCE: 64
```

Pro Pro Ile Glu Lys
1               5

```
<210> SEQ ID NO 65
<211> LENGTH: 5
<212> TYPE: PRT
<213> ORGANISM: Artificial Sequence
<220> FEATURE:
<223> OTHER INFORMATION: Synthetic peptide

<400> SEQUENCE: 65

Pro Ile Asp Lys Pro
1               5

<210> SEQ ID NO 66
<211> LENGTH: 6
<212> TYPE: PRT
<213> ORGANISM: Artificial Sequence
<220> FEATURE:
<223> OTHER INFORMATION: Synthetic peptide

<400> SEQUENCE: 66

Pro Pro Ile Asp Lys Pro
1               5

<210> SEQ ID NO 67
<211> LENGTH: 5
<212> TYPE: PRT
<213> ORGANISM: Artificial Sequence
<220> FEATURE:
<223> OTHER INFORMATION: Synthetic peptide

<400> SEQUENCE: 67

Pro Ile Glu Lys Pro
1               5

<210> SEQ ID NO 68
<211> LENGTH: 6
<212> TYPE: PRT
<213> ORGANISM: Artificial Sequence
<220> FEATURE:
<223> OTHER INFORMATION: Synthetic peptide

<400> SEQUENCE: 68

Pro Pro Ile Glu Lys Pro
1               5

<210> SEQ ID NO 69
<211> LENGTH: 6
<212> TYPE: PRT
<213> ORGANISM: Artificial Sequence
<220> FEATURE:
<223> OTHER INFORMATION: Synthetic peptide

<400> SEQUENCE: 69

Pro Ile Asp Lys Pro Ser
1               5

<210> SEQ ID NO 70
<211> LENGTH: 7
<212> TYPE: PRT
<213> ORGANISM: Artificial Sequence
<220> FEATURE:
<223> OTHER INFORMATION: Synthetic peptide

<400> SEQUENCE: 70

Pro Pro Ile Asp Lys Pro Ser
1               5
```

```
<210> SEQ ID NO 71
<211> LENGTH: 6
<212> TYPE: PRT
<213> ORGANISM: Artificial Sequence
<220> FEATURE:
<223> OTHER INFORMATION: Synthetic peptide

<400> SEQUENCE: 71

Pro Ile Glu Lys Pro Ser
1               5

<210> SEQ ID NO 72
<211> LENGTH: 7
<212> TYPE: PRT
<213> ORGANISM: Artificial Sequence
<220> FEATURE:
<223> OTHER INFORMATION: Synthetic peptide

<400> SEQUENCE: 72

Pro Pro Ile Glu Lys Pro Ser
1               5

<210> SEQ ID NO 73
<211> LENGTH: 6
<212> TYPE: PRT
<213> ORGANISM: Artificial Sequence
<220> FEATURE:
<223> OTHER INFORMATION: Synthetic peptide

<400> SEQUENCE: 73

Pro Ile Asp Lys Pro Cys
1               5

<210> SEQ ID NO 74
<211> LENGTH: 7
<212> TYPE: PRT
<213> ORGANISM: Artificial Sequence
<220> FEATURE:
<223> OTHER INFORMATION: Synthetic peptide

<400> SEQUENCE: 74

Pro Pro Ile Asp Lys Pro Cys
1               5

<210> SEQ ID NO 75
<211> LENGTH: 6
<212> TYPE: PRT
<213> ORGANISM: Artificial Sequence
<220> FEATURE:
<223> OTHER INFORMATION: Synthetic peptide

<400> SEQUENCE: 75

Pro Ile Glu Lys Pro Cys
1               5

<210> SEQ ID NO 76
<211> LENGTH: 7
<212> TYPE: PRT
<213> ORGANISM: Artificial Sequence
<220> FEATURE:
<223> OTHER INFORMATION: Synthetic peptide

<400> SEQUENCE: 76

Pro Pro Ile Glu Lys Pro Cys
1               5

<210> SEQ ID NO 77
```

```
<211> LENGTH: 7
<212> TYPE: PRT
<213> ORGANISM: Artificial Sequence
<220> FEATURE:
<223> OTHER INFORMATION: Synthetic peptide

<400> SEQUENCE: 77

Pro Ile Asp Lys Pro Ser Gln
1               5

<210> SEQ ID NO 78
<211> LENGTH: 8
<212> TYPE: PRT
<213> ORGANISM: Artificial Sequence
<220> FEATURE:
<223> OTHER INFORMATION: Synthetic peptide

<400> SEQUENCE: 78

Pro Pro Ile Asp Lys Pro Ser Gln
1               5

<210> SEQ ID NO 79
<211> LENGTH: 7
<212> TYPE: PRT
<213> ORGANISM: Artificial Sequence
<220> FEATURE:
<223> OTHER INFORMATION: Synthetic peptide

<400> SEQUENCE: 79

Pro Ile Glu Lys Pro Ser Gln
1               5

<210> SEQ ID NO 80
<211> LENGTH: 8
<212> TYPE: PRT
<213> ORGANISM: Artificial Sequence
<220> FEATURE:
<223> OTHER INFORMATION: Synthetic peptide

<400> SEQUENCE: 80

Pro Pro Ile Glu Lys Pro Ser Gln
1               5

<210> SEQ ID NO 81
<211> LENGTH: 7
<212> TYPE: PRT
<213> ORGANISM: Artificial Sequence
<220> FEATURE:
<223> OTHER INFORMATION: Synthetic peptide

<400> SEQUENCE: 81

Pro Ile Asp Lys Pro Cys Gln
1               5

<210> SEQ ID NO 82
<211> LENGTH: 8
<212> TYPE: PRT
<213> ORGANISM: Artificial Sequence
<220> FEATURE:
<223> OTHER INFORMATION: Synthetic peptide

<400> SEQUENCE: 82

Pro Pro Ile Asp Lys Pro Cys Gln
1               5

<210> SEQ ID NO 83
<211> LENGTH: 7
```

```
<212> TYPE: PRT
<213> ORGANISM: Artificial Sequence
<220> FEATURE:
<223> OTHER INFORMATION: Synthetic peptide

<400> SEQUENCE: 83

Pro Ile Glu Lys Pro Cys Gln
1               5

<210> SEQ ID NO 84
<211> LENGTH: 8
<212> TYPE: PRT
<213> ORGANISM: Artificial Sequence
<220> FEATURE:
<223> OTHER INFORMATION: Synthetic peptide

<400> SEQUENCE: 84

Pro Pro Ile Glu Lys Pro Cys Gln
1               5

<210> SEQ ID NO 85
<211> LENGTH: 7
<212> TYPE: PRT
<213> ORGANISM: Artificial Sequence
<220> FEATURE:
<223> OTHER INFORMATION: Synthetic peptide

<400> SEQUENCE: 85

Pro His His His His His His
1               5

<210> SEQ ID NO 86
<211> LENGTH: 8
<212> TYPE: PRT
<213> ORGANISM: Artificial Sequence
<220> FEATURE:
<223> OTHER INFORMATION: Synthetic peptide

<400> SEQUENCE: 86

Pro Pro His His His His His His
1               5

<210> SEQ ID NO 87
<211> LENGTH: 8
<212> TYPE: PRT
<213> ORGANISM: Artificial Sequence
<220> FEATURE:
<223> OTHER INFORMATION: Synthetic peptide

<400> SEQUENCE: 87

Pro Cys His His His His His His
1               5

<210> SEQ ID NO 88
<211> LENGTH: 9
<212> TYPE: PRT
<213> ORGANISM: Artificial Sequence
<220> FEATURE:
<223> OTHER INFORMATION: Synthetic peptide

<400> SEQUENCE: 88

Pro Pro Cys His His His His His His
1               5

<210> SEQ ID NO 89
<211> LENGTH: 5
<212> TYPE: PRT
```

```
<213> ORGANISM: Artificial Sequence
<220> FEATURE:
<223> OTHER INFORMATION: Synthetic peptide

<400> SEQUENCE: 89

Pro Val Gly Val Val
1               5

<210> SEQ ID NO 90
<211> LENGTH: 184
<212> TYPE: PRT
<213> ORGANISM: Homo sapiens

<400> SEQUENCE: 90

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
                20                  25                  30

Arg Ile Thr Tyr Gly Glu Thr Gly Gly Asn Ser Pro Val Gln Glu Phe
            35                  40                  45

Thr Val Pro Gly Ser Lys Ser Thr Ala Thr Ile Ser Gly Leu Lys Pro
        50                  55                  60

Gly Val Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Arg Thr Glu Ile
                85                  90                  95

Asp Lys Pro Ser Gln Met Gln Val Thr Asp Val Gln Asp Asn Ser Ile
            100                 105                 110

Ser Val Lys Trp Leu Pro Ser Ser Pro Val Thr Gly Tyr Arg Val
        115                 120                 125

Thr Thr Thr Pro Lys Asn Gly Pro Gly Pro Thr Lys Thr Lys Thr Ala
        130                 135                 140

Gly Pro Asp Gln Thr Glu Met Thr Ile Glu Gly Leu Gln Pro Thr Val
145                 150                 155                 160

Glu Tyr Val Val Ser Val Tyr Ala Gln Asn Pro Ser Gly Glu Ser Gln
                165                 170                 175

Pro Leu Val Gln Thr Ala Val Thr
            180

<210> SEQ ID NO 91
<211> LENGTH: 9
<212> TYPE: PRT
<213> ORGANISM: Homo sapiens

<400> SEQUENCE: 91

Arg Thr Glu Ile Asp Lys Pro Ser Gln
1               5

<210> SEQ ID NO 92
<211> LENGTH: 15
<212> TYPE: PRT
<213> ORGANISM: Artificial Sequence
<220> FEATURE:
<223> OTHER INFORMATION: Synthetic peptide

<400> SEQUENCE: 92

Arg Thr Glu Ile Glu Lys Pro Ser Gln His His His His His
1               5                   10                  15

<210> SEQ ID NO 93
```

```
<211> LENGTH: 9
<212> TYPE: PRT
<213> ORGANISM: Artificial Sequence
<220> FEATURE:
<223> OTHER INFORMATION: Synthetic peptide

<400> SEQUENCE: 93

Arg Thr Pro His His His His His His
1               5

<210> SEQ ID NO 94
<211> LENGTH: 4
<212> TYPE: PRT
<213> ORGANISM: Artificial Sequence
<220> FEATURE:
<223> OTHER INFORMATION: Synthetic peptide

<400> SEQUENCE: 94

Arg Thr Glu Cys
1

<210> SEQ ID NO 95
<211> LENGTH: 4
<212> TYPE: PRT
<213> ORGANISM: Artificial Sequence
<220> FEATURE:
<223> OTHER INFORMATION: Synthetic peptide

<400> SEQUENCE: 95

Arg Thr Pro Cys
1

<210> SEQ ID NO 96
<211> LENGTH: 110
<212> TYPE: PRT
<213> ORGANISM: Artificial Sequence
<220> FEATURE:
<223> OTHER INFORMATION: Synthetic polypeptide

<400> SEQUENCE: 96

Met Gly Val Ser Asp Val Pro Arg Asp Leu Glu Val Val Ala Ala Thr
1               5                   10                  15

Pro Thr Ser Leu Leu Ile Ser Trp Asp Ala Pro Ala Glu Gly Tyr Gly
            20                  25                  30

Tyr Tyr Arg Ile Thr Tyr Gly Glu Thr Gly Gly Asn Ser Pro Val Gln
        35                  40                  45

Glu Phe Thr Val Pro Val Ser Lys Gly Thr Ala Thr Ile Ser Gly Leu
    50                  55                  60

Lys Pro Gly Val Asp Tyr Thr Ile Thr Val Tyr Ala Val Glu Phe Asp
65                  70                  75                  80

Phe Pro Gly Ala Gly Tyr Tyr His Arg Pro Ile Ser Ile Asn Tyr Arg
                85                  90                  95

Thr Glu Ile Asp Lys Pro Ser Gln His His His His His
                100                 105                 110

<210> SEQ ID NO 97
<211> LENGTH: 104
<212> TYPE: PRT
<213> ORGANISM: Artificial Sequence
<220> FEATURE:
<223> OTHER INFORMATION: Synthetic polypeptide

<400> SEQUENCE: 97

Met Gly Val Ser Asp Val Pro Arg Asp Leu Glu Val Val Ala Ala Thr
```

```
            1               5                  10                 15
          Pro Thr Ser Leu Leu Ile Ser Trp Asp Ala Pro Ala Glu Gly Tyr Gly
                          20                 25                 30

Tyr Tyr Arg Ile Thr Tyr Gly Glu Thr Gly Gly Asn Ser Pro Val Gln
                      35                 40                 45

Glu Phe Thr Val Pro Val Ser Lys Gly Thr Ala Thr Ile Ser Gly Leu
                  50                 55                 60

Lys Pro Gly Val Asp Tyr Thr Ile Thr Val Tyr Ala Val Glu Phe Asp
          65                 70                 75                 80

Phe Pro Gly Ala Gly Tyr Tyr His Arg Pro Ile Ser Ile Asn Tyr Arg
                          85                 90                 95

Thr Pro His His His His His His
                          100

<210> SEQ ID NO 98
<211> LENGTH: 104
<212> TYPE: PRT
<213> ORGANISM: Artificial Sequence
<220> FEATURE:
<223> OTHER INFORMATION: Synthetic polypeptide

<400> SEQUENCE: 98

Met Gly Val Ser Asp Val Pro Arg Asp Leu Glu Val Val Ala Ala Thr
1               5                  10                 15

Pro Thr Ser Leu Leu Ile Ser Trp Thr Leu Pro His Ala Gly Arg Ala
                20                 25                 30

His Tyr Tyr Arg Ile Thr Tyr Gly Glu Thr Gly Gly Asn Ser Pro Val
            35                 40                 45

Gln Glu Phe Thr Val Pro Gly Arg Gly Val Thr Ala Thr Ile Ser Gly
        50                 55                 60

Leu Lys Pro Gly Val Asp Tyr Thr Ile Thr Val Tyr Ala Val Thr Val
65                 70                 75                 80

Thr Thr Thr Lys Val Ile His Tyr Lys Pro Ile Ser Ile Asn Tyr Arg
                85                 90                 95

Thr Pro His His His His His His
                100

<210> SEQ ID NO 99
<211> LENGTH: 99
<212> TYPE: PRT
<213> ORGANISM: Artificial Sequence
<220> FEATURE:
<223> OTHER INFORMATION: Synthetic polypeptide

<400> SEQUENCE: 99

Met Gly Val Ser Asp Val Pro Arg Asp Leu Glu Val Val Ala Ala Thr
1               5                  10                 15

Pro Thr Ser Leu Leu Ile Ser Trp Asp Ala Pro Ala Glu Gly Tyr Gly
                20                 25                 30

Tyr Tyr Arg Ile Thr Tyr Gly Glu Thr Gly Gly Asn Ser Pro Val Gln
            35                 40                 45

Glu Phe Thr Val Pro Val Ser Lys Gly Thr Ala Thr Ile Ser Gly Leu
        50                 55                 60

Lys Pro Gly Val Asp Tyr Thr Ile Thr Val Tyr Ala Val Glu Phe Asp
65                 70                 75                 80

Phe Pro Gly Ala Gly Tyr Tyr His Arg Pro Ile Ser Ile Asn Tyr Arg
                85                 90                 95
```

Thr Glu Cys

<210> SEQ ID NO 100
<211> LENGTH: 99
<212> TYPE: PRT
<213> ORGANISM: Artificial Sequence
<220> FEATURE:
<223> OTHER INFORMATION: Synthetic polypeptide

<400> SEQUENCE: 100

Met Gly Val Ser Asp Val Pro Arg Asp Leu Glu Val Val Ala Ala Thr
1               5                   10                  15

Pro Thr Ser Leu Leu Ile Ser Trp Asp Ala Pro Ala Glu Gly Tyr Gly
            20                  25                  30

Tyr Tyr Arg Ile Thr Tyr Gly Glu Thr Gly Gly Asn Ser Pro Val Gln
        35                  40                  45

Glu Phe Thr Val Pro Val Ser Lys Gly Thr Ala Thr Ile Ser Gly Leu
    50                  55                  60

Lys Pro Gly Val Asp Tyr Thr Ile Thr Val Tyr Ala Val Glu Phe Asp
65                  70                  75                  80

Phe Pro Gly Ala Gly Tyr Tyr His Arg Pro Ile Ser Ile Asn Tyr Arg
                85                  90                  95

Thr Pro Cys

<210> SEQ ID NO 101
<211> LENGTH: 11
<212> TYPE: PRT
<213> ORGANISM: Artificial Sequence
<220> FEATURE:
<223> OTHER INFORMATION: Synthetic peptide

<400> SEQUENCE: 101

Asn Tyr Arg Thr Glu Ile Glu Lys Pro Cys Gln
1               5                   10

<210> SEQ ID NO 102
<211> LENGTH: 6
<212> TYPE: PRT
<213> ORGANISM: Artificial Sequence
<220> FEATURE:
<223> OTHER INFORMATION: Synthetic peptide

<400> SEQUENCE: 102

Asn Tyr Arg Thr Pro Cys
1               5

<210> SEQ ID NO 103
<211> LENGTH: 17
<212> TYPE: PRT
<213> ORGANISM: Artificial Sequence
<220> FEATURE:
<223> OTHER INFORMATION: Synthetic peptide

<400> SEQUENCE: 103

Asn Tyr Arg Thr Glu Ile Glu Lys Pro Ser Gln His His His His His
1               5                   10                  15

His

<210> SEQ ID NO 104
<211> LENGTH: 10
<212> TYPE: PRT
<213> ORGANISM: Artificial Sequence
<220> FEATURE:

```
<223> OTHER INFORMATION: Synthetic peptide

<400> SEQUENCE: 104

Asn Tyr Arg Thr His His His His His His
1               5                   10

<210> SEQ ID NO 105
<211> LENGTH: 11
<212> TYPE: PRT
<213> ORGANISM: Artificial Sequence
<220> FEATURE:
<223> OTHER INFORMATION: Synthetic peptide

<400> SEQUENCE: 105

Asn Tyr Arg Thr Pro His His His His His His
1               5                   10

<210> SEQ ID NO 106
<211> LENGTH: 12
<212> TYPE: PRT
<213> ORGANISM: Artificial Sequence
<220> FEATURE:
<223> OTHER INFORMATION: Synthetic peptide

<400> SEQUENCE: 106

Asn Tyr Arg Thr Pro Pro His His His His His His
1               5                   10

<210> SEQ ID NO 107
<211> LENGTH: 5
<212> TYPE: PRT
<213> ORGANISM: Artificial Sequence
<220> FEATURE:
<223> OTHER INFORMATION: Synthetic peptide

<400> SEQUENCE: 107

Asn Tyr Arg Thr Glu
1               5

<210> SEQ ID NO 108
<211> LENGTH: 5
<212> TYPE: PRT
<213> ORGANISM: Artificial Sequence
<220> FEATURE:
<223> OTHER INFORMATION: Synthetic peptide

<400> SEQUENCE: 108

Asn Tyr Arg Thr Pro
1               5

<210> SEQ ID NO 109
<211> LENGTH: 6
<212> TYPE: DNA
<213> ORGANISM: Homo sapiens
<220> FEATURE:
<221> NAME/KEY: modified_base
<222> LOCATION: (2)..(2)
<223> OTHER INFORMATION: a, c, t, g, unknown or other
<220> FEATURE:
<221> NAME/KEY: misc_feature
<222> LOCATION: (2)..(2)
<223> OTHER INFORMATION: n is a, c, g, or t

<400> SEQUENCE: 109 cncaat                                                              6

<210> SEQ ID NO 110
```

```
<211> LENGTH: 6
<212> TYPE: DNA
<213> ORGANISM: Homo sapiens

<400> SEQUENCE: 110 aataaa                                                                      6

<210> SEQ ID NO 111
<211> LENGTH: 15
<212> TYPE: PRT
<213> ORGANISM: Artificial Sequence
<220> FEATURE:
<223> OTHER INFORMATION: Synthetic peptide

<400> SEQUENCE: 111

Gly Gly Gly Gly Ser Gly Gly Gly Ser Gly Gly Gly Ser
1               5                   10                  15

<210> SEQ ID NO 112
<211> LENGTH: 110
<212> TYPE: PRT
<213> ORGANISM: Artificial Sequence
<220> FEATURE:
<223> OTHER INFORMATION: Synthetic polypeptide

<400> SEQUENCE: 112

Met Gly Val Ser Asp Val Pro Arg Asp Leu Glu Val Val Ala Ala Thr
1               5                   10                  15

Pro Thr Ser Leu Leu Ile Ser Trp Thr Leu Pro His Ala Gly Arg Ala
                20                  25                  30

His Tyr Tyr Arg Ile Thr Tyr Gly Glu Thr Gly Gly Asn Ser Pro Val
            35                  40                  45

Gln Glu Phe Thr Val Pro Gly Arg Gly Val Thr Ala Thr Ile Ser Gly
        50                  55                  60

Leu Lys Pro Gly Val Asp Tyr Thr Ile Thr Val Tyr Ala Val Thr Val
65                  70                  75                  80

Thr Thr Thr Lys Val Ile His Tyr Lys Pro Ile Ser Ile Asn Tyr Arg
                85                  90                  95

Thr Glu Ile Asp Lys Pro Ser Gln His His His His His
            100                 105                 110

<210> SEQ ID NO 113
<211> LENGTH: 7
<212> TYPE: PRT
<213> ORGANISM: Artificial Sequence
<220> FEATURE:
<223> OTHER INFORMATION: Synthetic peptide

<400> SEQUENCE: 113

Glu Ile Asp Lys Pro Ser Gln
1               5

<210> SEQ ID NO 114
<211> LENGTH: 4
<212> TYPE: PRT
<213> ORGANISM: Artificial Sequence
<220> FEATURE:
<223> OTHER INFORMATION: Synthetic peptide

<400> SEQUENCE: 114

Pro Pro Ile Asp
1
```

```
<210> SEQ ID NO 115
<211> LENGTH: 4
<212> TYPE: PRT
<213> ORGANISM: Artificial Sequence
<220> FEATURE:
<223> OTHER INFORMATION: Synthetic peptide

<400> SEQUENCE: 115

Pro Pro Ile Glu
1

<210> SEQ ID NO 116
<211> LENGTH: 6
<212> TYPE: PRT
<213> ORGANISM: Artificial Sequence
<220> FEATURE:
<223> OTHER INFORMATION: Synthetic 6xHis tag"

<400> SEQUENCE: 116

His His His His His His
1               5

<210> SEQ ID NO 117
<211> LENGTH: 2
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(2)
<223> OTHER INFORMATION: /note="See specification as filed for detailed
      description of substitutions and preferred embodiments"
<220> FEATURE:
<221> NAME/KEY: MOD_RES
<222> LOCATION: (2)..(2)
<223> OTHER INFORMATION: Any amino acid

<400> SEQUENCE: 117

Pro Xaa
1

<210> SEQ ID NO 118
<211> LENGTH: 1
<212> TYPE: PRT
<213> ORGANISM: Artificial Sequence
<220> FEATURE:
<223> OTHER INFORMATION: Synthetic peptide

<400> SEQUENCE: 118

Pro
1

<210> SEQ ID NO 119
<211> LENGTH: 2
<212> TYPE: PRT
<213> ORGANISM: Artificial Sequence
<220> FEATURE:
<223> OTHER INFORMATION: Synthetic peptide

<400> SEQUENCE: 119

Pro Pro
1

<210> SEQ ID NO 120
<211> LENGTH: 151
<212> TYPE: PRT
<213> ORGANISM: Artificial Sequence
<220> FEATURE:
```

<223> OTHER INFORMATION: Synthetic polypeptide
<220> FEATURE:
<221> NAME/KEY: MISC_FEATURE
<222> LOCATION: (1)..(151)
<223> OTHER INFORMATION: /note="See specification as filed for detailed
    description of substitutions and preferred embodiments"
<220> FEATURE:
<221> NAME/KEY: MOD_RES
<222> LOCATION: (2)..(151)
<223> OTHER INFORMATION: Any amino acid
<220> FEATURE:
<221> NAME/KEY: VARIANT
<222> LOCATION: (2)..(151)
<223> OTHER INFORMATION: /replace=" "
<220> FEATURE:
<221> NAME/KEY: MISC_FEATURE
<222> LOCATION: (2)..(151)
<223> OTHER INFORMATION: /note="This region may encompass 1-150
    residues"

<400> SEQUENCE: 120

Pro Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa
65              70                  75                  80

Xaa Xaa Xaa Xaa Xaa Xaa Xaa Xaa Xaa Xaa Xaa Xaa Xaa Xaa Xaa
            85                  90                  95

Xaa Xaa Xaa Xaa Xaa Xaa Xaa Xaa Xaa Xaa Xaa Xaa Xaa Xaa Xaa
        100                 105                 110

Xaa Xaa Xaa Xaa Xaa Xaa Xaa Xaa Xaa Xaa Xaa Xaa Xaa Xaa Xaa
    115                 120                 125

Xaa Xaa Xaa Xaa Xaa Xaa Xaa Xaa Xaa Xaa Xaa Xaa Xaa Xaa Xaa
130                 135                 140

Xaa Xaa Xaa Xaa Xaa Xaa Xaa
145                 150

<210> SEQ ID NO 121
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(11)
<223> OTHER INFORMATION: /note="See specification as filed for detailed
    description of substitutions and preferred embodiments"
<220> FEATURE:
<221> NAME/KEY: MOD_RES
<222> LOCATION: (2)..(11)
<223> OTHER INFORMATION: Any amino acid
<220> FEATURE:
<221> NAME/KEY: VARIANT
<222> LOCATION: (2)..(11)
<223> OTHER INFORMATION: /replace=" "
<220> FEATURE:
<221> NAME/KEY: MISC_FEATURE
<222> LOCATION: (2)..(11)
<223> OTHER INFORMATION: /note="This region may encompass 1-10 residues"

<400> SEQUENCE: 121

```
Pro Xaa Xaa Xaa Xaa Xaa Xaa Xaa Xaa Xaa
1               5                  10
```

<210> SEQ ID NO 122
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(6)
<223> OTHER INFORMATION: /note="See specification as filed for detailed
      description of substitutions and preferred embodiments"
<220> FEATURE:
<221> NAME/KEY: MOD_RES
<222> LOCATION: (2)..(6)
<223> OTHER INFORMATION: Any amino acid
<220> FEATURE:
<221> NAME/KEY: VARIANT
<222> LOCATION: (2)..(6)
<223> OTHER INFORMATION: /replace=" "
<220> FEATURE:
<221> NAME/KEY: MISC_FEATURE
<222> LOCATION: (2)..(6)
<223> OTHER INFORMATION: /note="This region may encompass 1-5 residues"

<400> SEQUENCE: 122

```
Pro Xaa Xaa Xaa Xaa Xaa
1               5
```

<210> SEQ ID NO 123
<211> LENGTH: 2
<212> TYPE: PRT
<213> ORGANISM: Artificial Sequence
<220> FEATURE:
<223> OTHER INFORMATION: Synthetic peptide

<400> SEQUENCE: 123

```
Pro Ile
1
```

<210> SEQ ID NO 124
<211> LENGTH: 2
<212> TYPE: PRT
<213> ORGANISM: Artificial Sequence
<220> FEATURE:
<223> OTHER INFORMATION: Synthetic peptide

<400> SEQUENCE: 124

```
Pro Cys
1
```

<210> SEQ ID NO 125
<211> LENGTH: 3
<212> TYPE: PRT
<213> ORGANISM: Artificial Sequence
<220> FEATURE:
<223> OTHER INFORMATION: Synthetic peptide

<400> SEQUENCE: 125

```
Pro Ile Asp
1
```

<210> SEQ ID NO 126
<211> LENGTH: 3
<212> TYPE: PRT
<213> ORGANISM: Artificial Sequence
<220> FEATURE:
<223> OTHER INFORMATION: Synthetic peptide

```
<400> SEQUENCE: 126

Pro Ile Glu
1

<210> SEQ ID NO 127
<211> LENGTH: 2
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(2)
<223> OTHER INFORMATION: /note="See specification as filed for detailed
      description of substitutions and preferred embodiments"
<220> FEATURE:
<221> NAME/KEY: MOD_RES
<222> LOCATION: (2)..(2)
<223> OTHER INFORMATION: Any amino acid

<400> SEQUENCE: 127

Pro Xaa
1

<210> SEQ ID NO 128
<211> LENGTH: 91
<212> TYPE: PRT
<213> ORGANISM: Homo sapiens

<400> SEQUENCE: 128

Arg Asp Leu Glu Val Val Ala Ala Thr Pro Thr Ser Leu Leu Ile Ser
1               5                   10                  15

Trp Asp Ala Pro Ala Val Thr Val Arg Tyr Tyr Arg Ile Thr Tyr Gly
                20                  25                  30

Glu Thr Gly Gly Asn Ser Pro Val Gln Glu Phe Thr Val Pro Gly Ser
            35                  40                  45

Lys Ser Thr Ala Thr Ile Ser Gly Leu Lys Pro Gly Val Asp Tyr Thr
    50                  55                  60

Ile Thr Val Tyr Ala Val Thr Gly Arg Gly Asp Ser Pro Ala Ser Ser
65                  70                  75                  80

Lys Pro Ile Ser Ile Asn Tyr Arg Thr Glu Ile
                85                  90

<210> SEQ ID NO 129
<211> LENGTH: 3
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: /replace="Gly" or " "
<220> FEATURE:
<221> NAME/KEY: MISC_FEATURE
<222> LOCATION: (1)..(2)
<223> OTHER INFORMATION: /note="When only 1 position is present, the
      position may be Met or Gly.  When two positions are present, the
      positions are Met-Gly. See specification for further explanation."
<220> FEATURE:
<221> NAME/KEY: MISC_FEATURE
<222> LOCATION: (1)..(3)
<223> OTHER INFORMATION: /note="Variant residues given in the sequence
      have no preference with respect to those in the annotations for
      variant positions"
<220> FEATURE:
<221> NAME/KEY: VARIANT
```

```
<222> LOCATION: (2)..(2)
<223> OTHER INFORMATION: /replace="Met" or " "

<400> SEQUENCE: 129

Met Gly Leu
1

<210> SEQ ID NO 130
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(6)
<223> OTHER INFORMATION: /note="Variant residues given in the sequence
      have no preference with respect to those in the annotations for
      variant positions"
<220> FEATURE:
<221> NAME/KEY: VARIANT
<222> LOCATION: (2)..(3)
<223> OTHER INFORMATION: /replace=" "
<220> FEATURE:
<221> NAME/KEY: VARIANT
<222> LOCATION: (5)..(6)
<223> OTHER INFORMATION: /replace=" "

<400> SEQUENCE: 130

Pro Pro Pro Cys Cys Cys
1               5
```